(12) United States Patent
Martinell et al.

(10) Patent No.: US 12,022,787 B2
(45) Date of Patent: Jul. 2, 2024

(54) EFFICIENT MONOCOT EMBRYO EXTRACTION AND PRESERVATION METHODS AND NOVEL USES THEREOF

(71) Applicant: Wisconsin Alumni Research Foundation, Madison, WI (US)

(72) Inventors: Brian Joseph Martinell, Mount Horeb, WI (US); Michael William Petersen, Merrimac, WI (US); Edward James Williams, Madison, WI (US); Frank Lloyd McFarland, Madison, WI (US); Nathaniel Schleif, Madison, WI (US); Shawn Michael Kaeppler, Oregon, WI (US); Heidi Flewelling Kaeppler, Oregon, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/905,594

(22) Filed: Jun. 18, 2020

(65) Prior Publication Data

US 2020/0396918 A1    Dec. 24, 2020

Related U.S. Application Data

(60) Provisional application No. 62/863,687, filed on Jun. 19, 2019.

(51) Int. Cl.
*A01H 4/00* (2006.01)
*C12N 15/82* (2006.01)

(52) U.S. Cl.
CPC ......... *A01H 4/005* (2013.01); *C12N 15/8205* (2013.01); *C12N 15/8207* (2013.01)

(58) Field of Classification Search
CPC . A01H 4/005; C12N 15/8205; C12N 15/8207
USPC ....................................................... 800/293
See application file for complete search history.

(56) References Cited

U.S. PATENT DOCUMENTS

| | | | |
|---|---|---|---|
| 7,939,325 B2 | 5/2011 | Adams | |
| 8,362,317 B2 * | 1/2013 | Calabotta et al. ....... | A01H 1/00 800/278 |
| 2019/0208723 A1 | 7/2019 | Petersen | |
| 2021/0071186 A1 | 3/2021 | Petersen | |
| 2022/0340916 A1 | 10/2022 | Duncan et al. | |
| 2022/0340925 A1 | 10/2022 | Chen et al. | |

OTHER PUBLICATIONS

Compton et al. 1992. In Vitro Cell. Dev. Biol. 28P: 197-201.*
Garrocho-Villegas et al. 2012. Plant Cell Culture Protocols, vol. 877, Chapter 14, pp. 173-182.*
Herter et al. Can. J. Plant Sci. 69: 763-774 (Year: 1989).*
Compton et al. In Vitro Cell. Dev. Biol.28P: 197-201 (Year: 1992).*
Garrocho-Villegas et al. Plant Cell Culture Protocols, Methods in Molecular Biology, vol. 877: 173-182 (Year: 2012).*
Anand, A., et al. (2018) An improved ternary vector system for Agrobacterium-mediated rapid maize transformation. Plant Molecular Biology (97) 187-200.
Bartlett, J., et al. (2008) High-throughput Agrobacterium-mediated barley transformation. Plant Methods (4) 22, 1-12.
Bregitzer P (1992) Plant regeneration and callus type in barley: effects of genotype and culture medium. Crop Sci 32:1108-1112.
Bregitzer P, et al. (1998) Somaclonal variation in the progeny of transgenic barley. Theor Appl Genet 96:421-425.
Bregitzer P, Poulson M (1995) Agronomic performance of barley lines derived from tissue culture. Crop Sci 35:1144-1148.
Bregitzer P, et al. (1995) Malting quality of barley lines derived from tissue culture. Cereal Chem 72:433-435.
Bregitzer P, et al (2002). Reduced somaclonal variation in barley is associated with culturing highly differentiated, meristematic tissues. Crop Sci 42:1303-1308.
Christou P (1992) Genetic transformation of crop plants using microprojectile bombardment. The Plant Journal 2(3);275-281.
Cobb RD. 2,3,5-Triphenyl tetrazolium chloride as a viability indicator of seeds fumigated with methyl bromide. Proc Association Off Seed Anal Soc Commer Seed Technol. 1956; 46:62-6.
Dahleen LS, et al (2002) An improved media system for high regeneration rates from barley immature embryo-derived callus cultures of commercial cultivars. Crop Sci42:934-938.
Duke SO, et al. Effects of glyphosate on metabolism of phenolic compounds I. Induction of phenylalanine ammonia-lyase activity in dark-grown maize roots. Plant Sci Lett. 1978;11:185-90.
Duke SO, et al. Effects of light on phenylalanine ammonia-lyase activity in dark-grown *Zea mays* (L.) seedlings. Plant Sci Lett. 1974;2:289-93.
Frame et al. "Genetic transformation using maize immature zygotic embryos," 2010, Plant Embryo Culture, pp. 327-341.
Frame, B. R., et al. "Maize (*Zea mays* L.)." Agrobacterium protocols (2006): 185-200.
Gordon-Kamm, B., et al. (2019) Using morphogenic genes to improve recovery and regeneration of transgenic plants. Plants (8) 38, 1-18.
Greenspan "Humidity Fixed Points of binary saturated aqueous solutions," 1977, Journal of Research of the National Bureau of Standards, 81A(1):89-96.
Hiei et al. "Improved frequency of transformation in rice and maize by treatment of immature embryos with centrifugation and heat prior to infection with Agrobacterium tumefaciens," Plant Cell, Tissue, and Organ Culture, 2006, 87(3):233-243.
Hoagland RE. Effects of glyphosate on metabolism of phenolic compounds: VI. Effects of glyphosine and glyphosate metabolites on phenylalanine ammonia-lyase activity, growth, and protein, chlorophyll, and anthocyanin levels in soybean (*Glycine max*) seedlings. Weed Sci. 1980;28:393-400.

(Continued)

*Primary Examiner* — Keith O. Robinson
(74) *Attorney, Agent, or Firm* — Quarles & Brady, LLP

(57) ABSTRACT

Disclosed herein are methods for sterile extraction, drying, storage, and transformation of immature and mature maize and monocot embryos. The present disclosure also describes a dried, storable, freezable value added maize and monocot explants.

23 Claims, 52 Drawing Sheets
(52 of 52 Drawing Sheet(s) Filed in Color)

(56) References Cited

OTHER PUBLICATIONS

John Innes Centre. Crop Transformation (BRACT). Webpage. Version dated Apr. 22, 2020 accessed online at: http://web.archive.org/web/20200422013148/https://www.jic.ac.uk/research-impact/technology-platforms/genomic-services/crop-transformation/.
Ishida, Y., et al. (2007) Agrobacterium-mediated transformation of maize, Nature Protocols (2) 1614-1621.
Ishida, Y., et al. (1996) High effiency transformation of maize (*Zea mays* L.) mediated by Agrobacterium tumefaciens. Nature Biotechnology (14) 745-750.
Kapila et al. "An Agrobacterium-mediated transient gene expression system for intact leaves," Plant Science, 1997, 122(1):101-108.
Khanna, et al. "Centrifugation assisted Agrobacterium tumefaciens-mediated transformation (CAAT) of embryogenic cell suspensions of banana (*Musa* spp. Cavendish AAA and Lady finger AAA)," Molecular Breeding, 2004, 14:239-252.
Komari T, et al. (2006) Binary vectors and super-binary vectors. In: KanWang (ed.), and Methods in Molecular Biology, vol. 343: Agrobacterium Protocols, vol. 1, Second Edition. Humana Press Inc., Totowa, NJ, pp. 15-41.
Kronzucker, H.J., et al. (1999) Inhibition of nitrate uptake by ammonium in barley. Analysis of component fluxes. Plant Physiol. (120) 1: 283-292.
Lemaux PG, et al. (1999) Transgenic cereals: *Hordeum vulgare* L. (barley). In: Vasil IK (ed) Molecular Improvement of Cereal Crops, pp. 255-316, Kluwer, Great Britain.
Lowe, K., et. al., (2016) Morphogenic Regulators Baby boom and Wuschel Improve Monocot Transformation. The Plant Cell (28) 1998-2015.
Mann, D.G.J., et al. (2012) Gateway-compatible vectors for high-throughput gene functional analysis in switchgrass (*Panicum virgatum* L.) and other *monocot* species. Plant Biotechnology Journal (10) 226-236.
Manoharan M, et al. (2002) Genetic transformation of the commercial barley (*Hordeum vulgare* L.) cultivar Conlon by particle bombardment of callus. Plant Cell Rep 21:76-80.
McCabe D, et al. (1993) Transformation of Elite Cotton Cultivars via Particle Bombardment of Meristems. Bio/Technology 11:596-598.
McCabe D, et al. (1988) Stable transformation of soybean (*Glycine max*) by particle acceleration. Bio/Technology 6:923-926.
Nakano, T., et al., (2018) FPX is a Novel Chemical Inducer that Promotes Callus Formation and Shoot Regeneration in Plants. Plant Cell Physiol. 59 (8) 1555-1567.
Rostami, H., et al. (2013) Optimization of multiple shoot induction and plant regeneration in Indian barley (*Hordeum vulgare*) cultivars using mature embryo. Saudi Journal of Biological Sciences (20) 251-255.
Schrammeijer B, et al. (1990). Meristem transformation of sunflower via Agrobacterium. Plant Cell Reports 9(2):55-60.
Sharma, V., et al. (2004) A highly efficient plant regeneration system through multiple shoot differentiation from commercial cultivars of barley (*Hordeum vulgare* L.) using meristematic shoot segments excised from germinated mature embryos. Plant Cell Rep (23) 9-16.
Sticklen, M.B., et al. (2005) Shoot apical meristem: a sustainable explant for generic transformation of cereal crops. In Vitro Cell. Dev. Biol.—Plant (41) 187-200.
Trick et al. "SAAT: sonication-assisted Agrobacterium-mediated transformation," Transgenic Research, 1997, 6(5):329-336.
Wexler et al. "Relative humidity-temperature relationships of some saturated salt solutions in the temperature range 0° C. to 50° C.," 1954, Journal of Research of the National Bureau of Standards, 53(1), Research Paper 2512.
Young et al. "Humidity control in the laboratory using salt solutions—a review," 1967, Journal of Chemical Technology and Biotechnology, 17(9):241-245.
Zaprometov MN, et al. Phenylalanine-ammonia lyase and synthesis of phenol compounds in maize seedlings. Sov Plant Physiol. 1972.
Zhang et al. "Transformation of recalcitrant maize elite inbreds using in vitro shoot meristematic cultures induced from germinated seedlings," Plant Cell Reports, 2002, 21(3):263-270.
Zhong, H., et al. (1992) In-vitro morphogenesis of corn (*Zea mays* L.). Planta (187) 483-489.
Zhong, H., et al. (1996) The competence of maize shoot meristems for integrative transformation and inherited expression of transgenes. Plant Physiol. (110) 1097-1107.

\* cited by examiner

Corn B73 iVAE experiment:
Imaged (after 4 day co-culture on filter paper with 1.75 ml iNO with 60 ppm Cleary's, 50 ppm nystatin, 10 ppm TBZ)

1) ES024 stored in PEG 1 wk 4C, exposed to 30s PEG/EtOH, 7277g (57% dead)
2) ES024 stored in "MS PEG" 1 week 4C, exposed to 30s PEG/EtOH, 7277g (9% dead)

FIG. 13
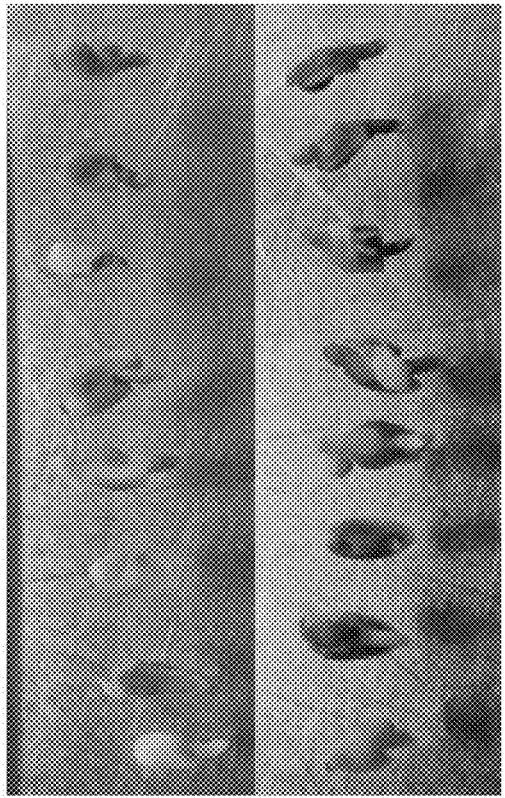
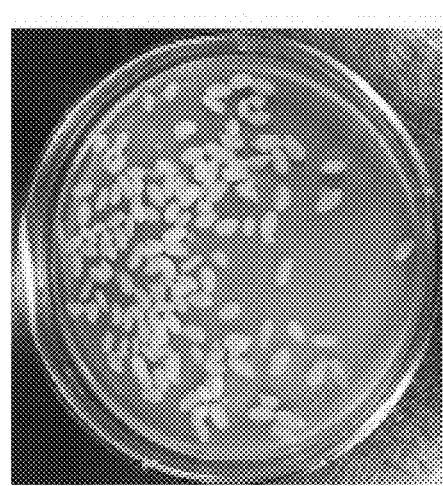

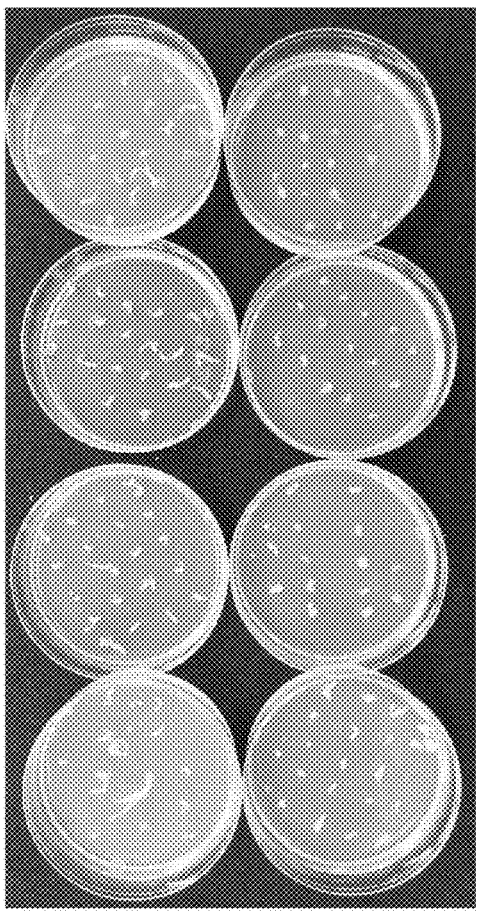
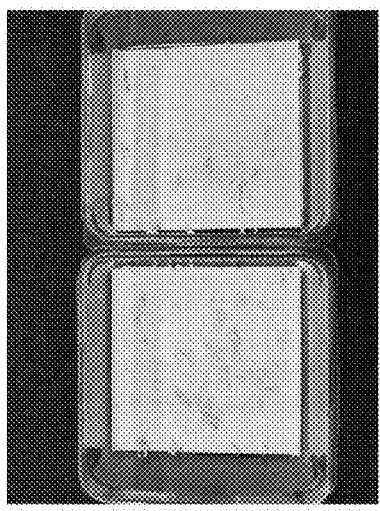
FIG. 16

FIG. 21

Imaged after 1.5 weeks post co-culture (MS salts + B5 vitamins)
- Explants derived from 12% moisture
- Induction on 3.5g/L phytagel with increased copper concentration Explants healthy on phytagel with increased copper; Transfer to 60 mg/L G418 media this week

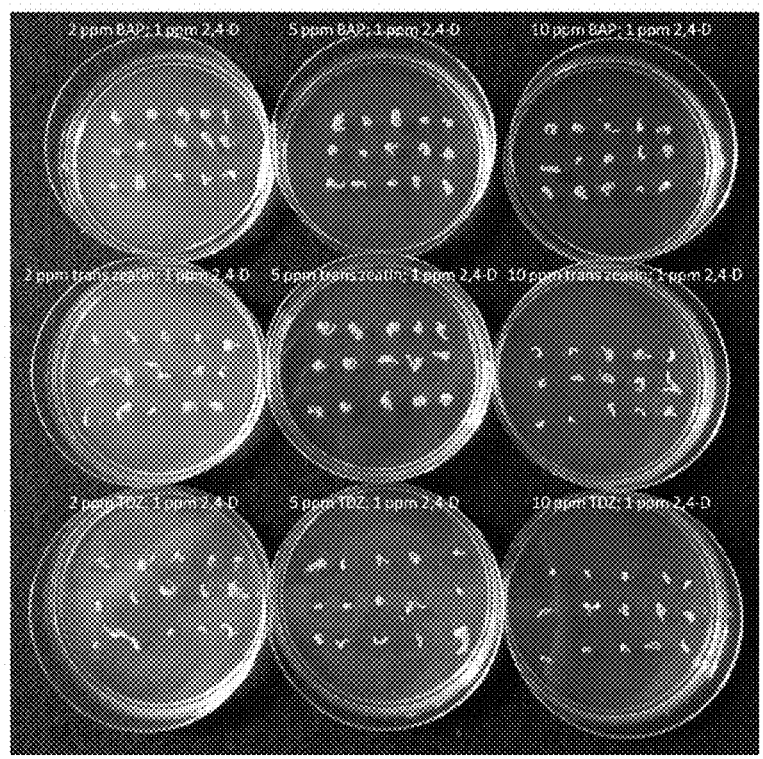

Callus response Media 3a
2 mg/L BAP; 0.5 mg/L 2,4-D

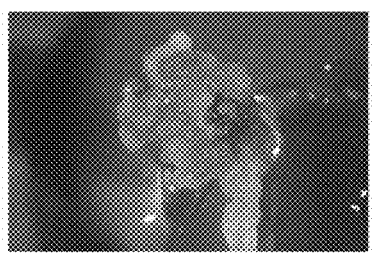

Budding response Media 3d
2 mg/L BAP; 1 mg/L 2,4-D

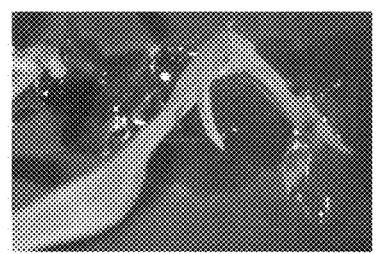

Germination response Media 3null
No PGRs

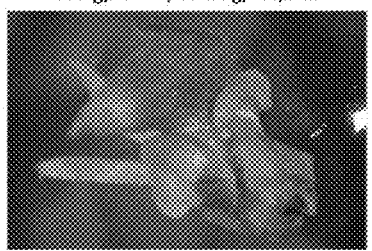

Multiple shooting response Media 3f
10 mg/L BAP; 1 mg/L 2,4-D

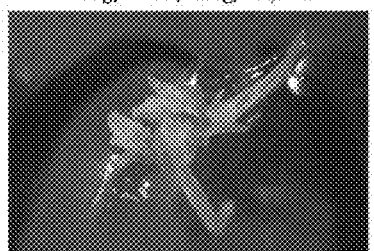

Multiple shooting response Media 3o
10 mg/L TDZ; 0.5 mg/L 2,4-D

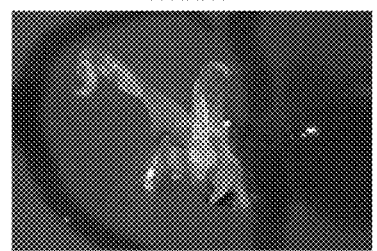

Multiple shooting response Media 3p
2 mg/L TDZ; 1 mg/L 2,4-D

FIG. 22
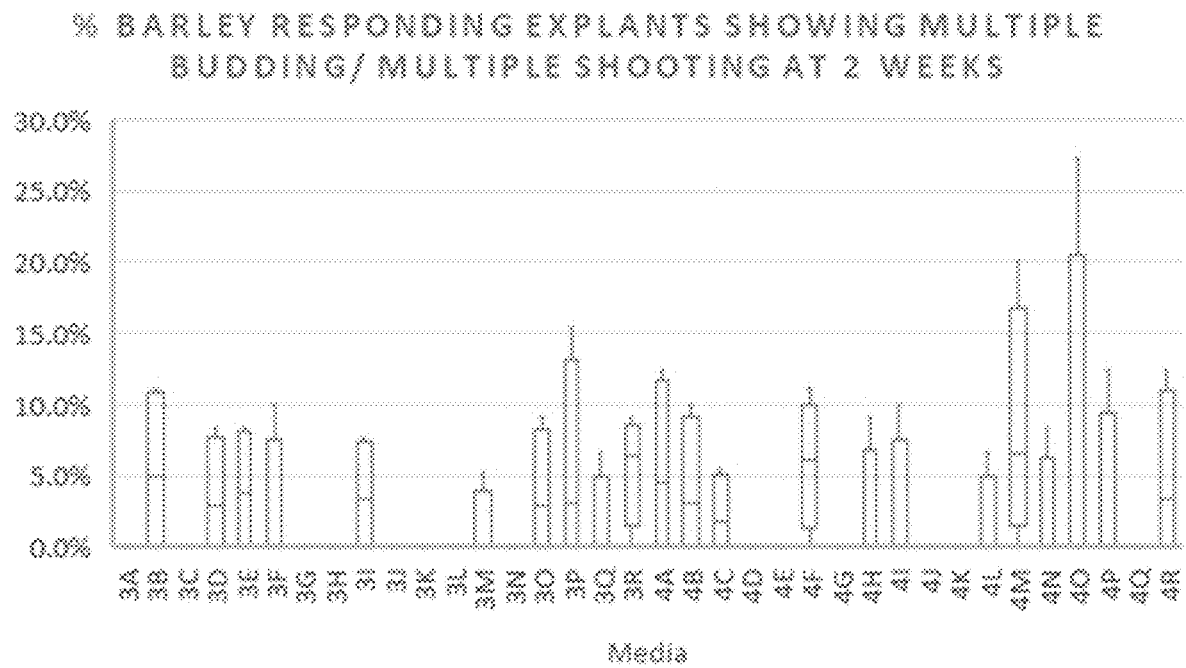
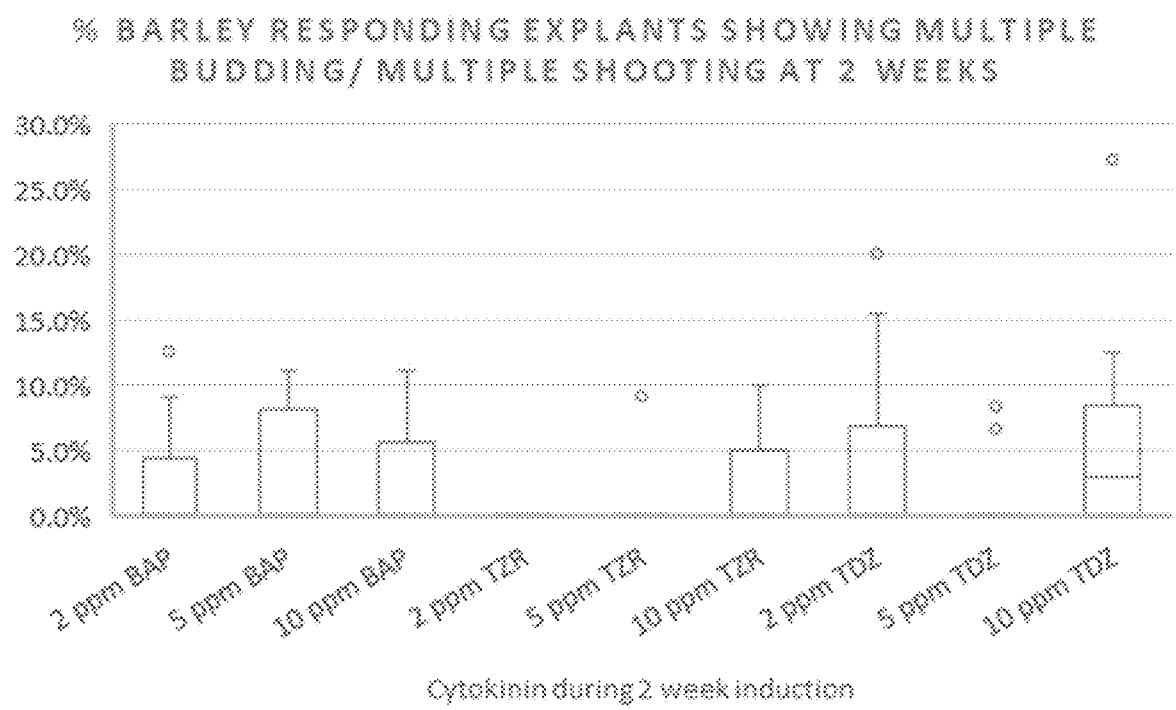

FIG. 23
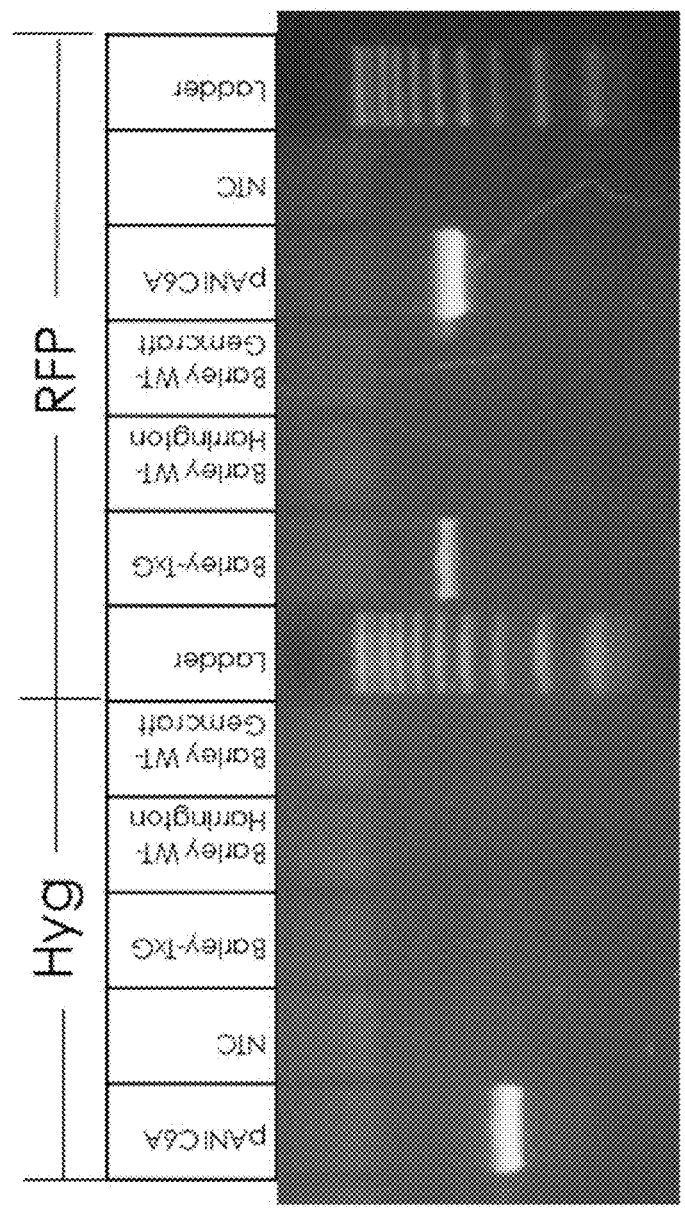

Fragment of RCGG1138 MONOCOT TEST 21 (RC3130) rc
9554 bp (molecule 13660 bp)

L 1 = 100 bp ladder
L 2 = blank
L 3 = 50:50 reagent negative control
L 4 = blank
L 5-16 = T0 Barley leaves 1-12 WP412-3
L 17 = blank
L 18-29 = T0 Barley leaves 13-24 WP412-3
L 30-33 = blank
L 34 = Barley leaf negative control
L 35 = blank
L 36 = 100 bp ladder FIG. 35
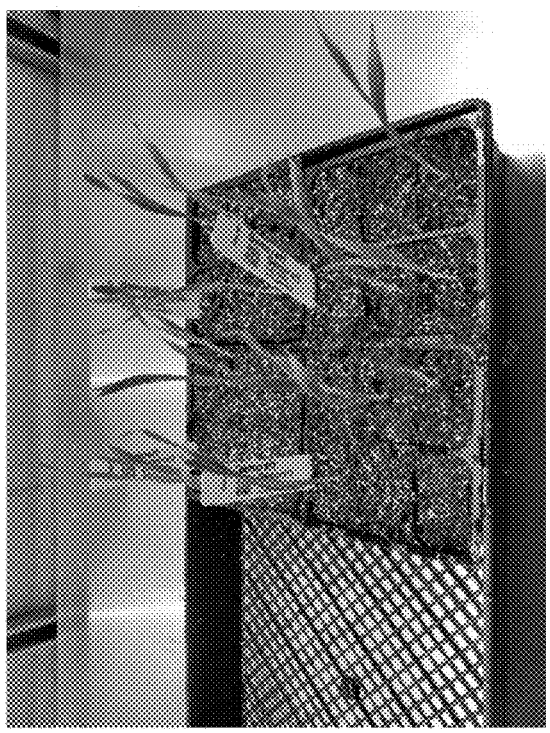
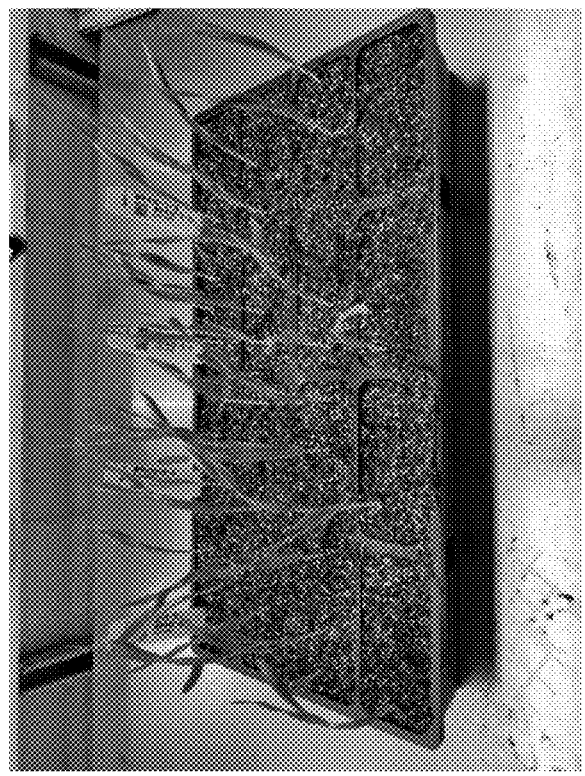
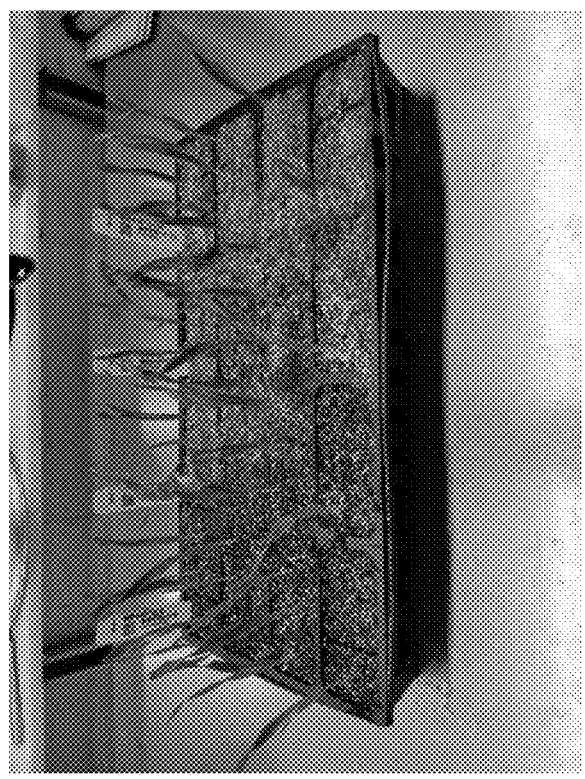

Ln 1 = 100 bp ladder
Ln 2 = blank
Ln 3 = 50:50 reagent negative control
Ln 4 = Barley leaf negative control
Ln 5 = blank
Ln 6 = T1 WP412-1 spike 1, plant 1
Ln 7 = T1 WP412-1 spike 1, plant 2
Ln 8 = T1 WP412-1 spike 1, plant 3
Ln 9 = T1 WP412-1 spike 1, plant 4
Ln 10 = T1 WP412-1 spike 1, plant 5
Ln 11 = T1 WP412-1 spike 1, plant 6
Ln 12 = T1 WP412-1 spike 1, plant 7
Ln 13 = T1 WP412-1 spike 1, plant 8
Ln 14 = T1 WP412-1 spike 1, plant 9
Ln 15 = T1 WP412-1 spike 1, plant 10
Ln 16 = blank
Ln 17 = 100 bp ladder Ln 1 = 100 bp ladder
Ln 2 = blank
Ln 3 = 50:50 reagent negative control
Ln 4 = Barley leaf negative control
Ln 5 = blank
Ln 6 = T1 WP412-4 spike 5, plant 1
Ln 7 = T1 WP412-4 spike 5, plant 2
Ln 8 = T1 WP412-4 spike 5, plant 3
Ln 9 = T1 WP412-4 spike 5, plant 4
Ln 10 = T1 WP412-4 spike 5, plant 5
Ln 11 = T1 WP412-4 spike 5, plant 6
Ln 12 = T1 WP412-4 spike 5, plant 7
Ln 13 = T1 WP412-4 spike 5, plant 8
Ln 14 = T1 WP412-4 spike 5, plant 9
Ln 15 = T1 WP412-4 spike 5, plant 10
Ln 16 = T1 WP412-4 spike 5, plant 11
Ln 17 = blank
Ln 18 = 100 bp ladder FIG. 48
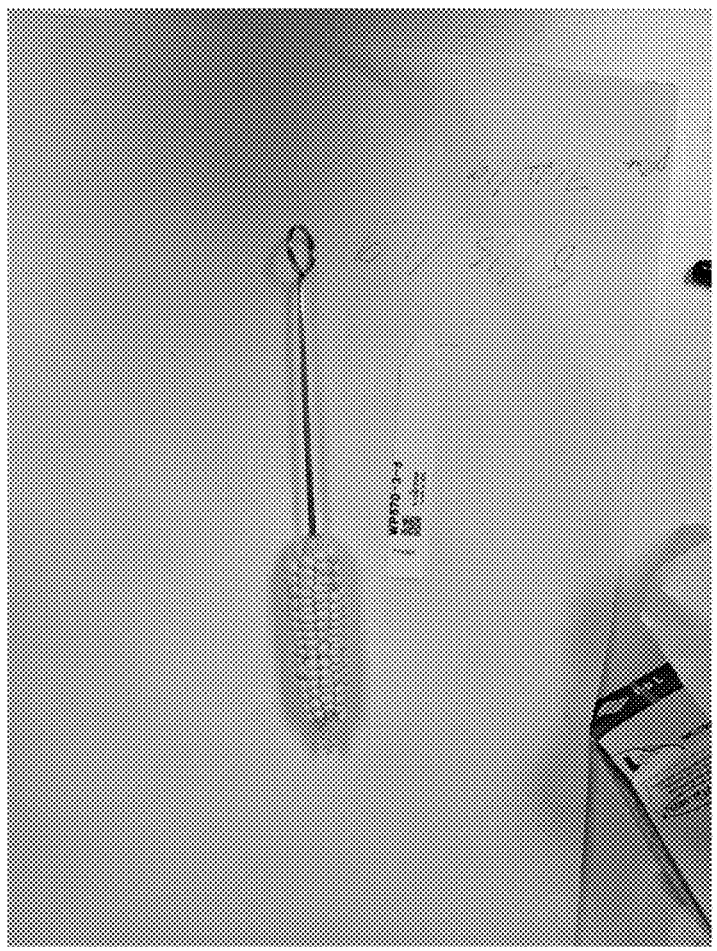
24 DAP segregating transgenic T0 ear Hi2 outcrossed with native B73 pollen
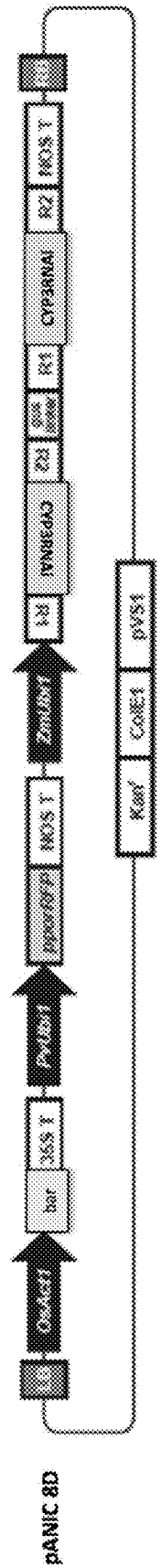

FIG. 49
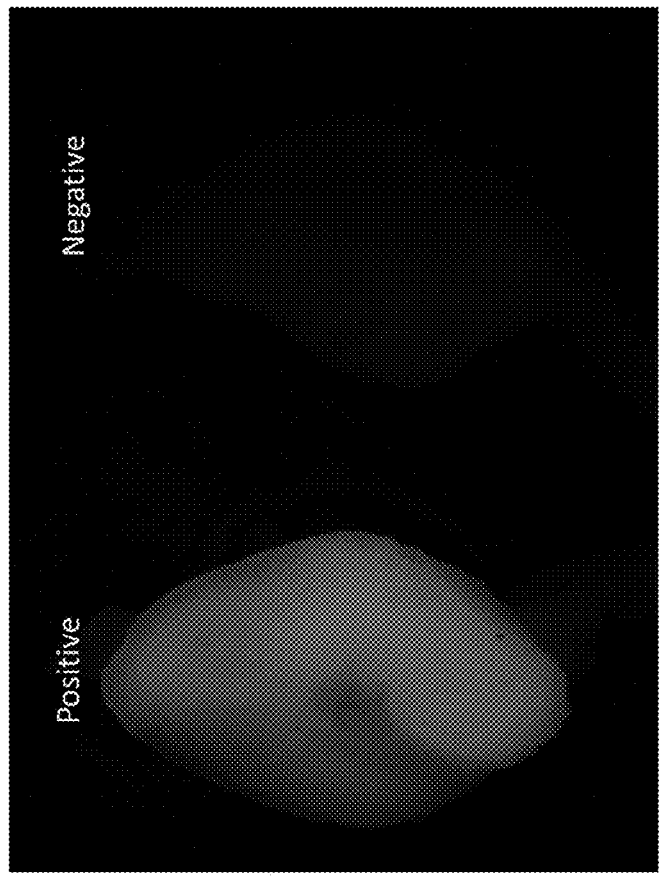
Fluorescent Protein (+ on left, negative on right)
Under Excitation Lighting and Filters
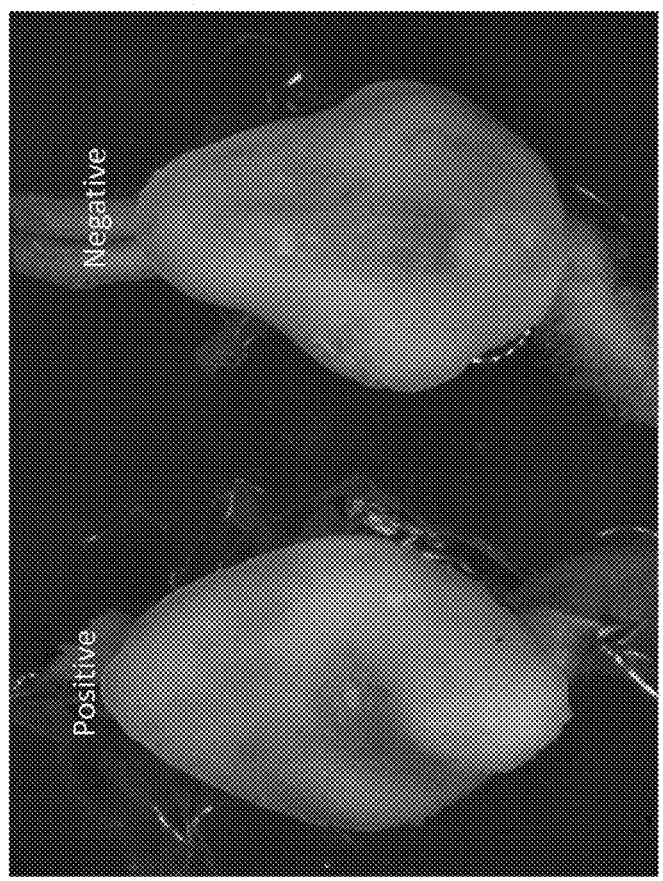
Fluorescent Protein (+ on left, negative on right)
Under White Light

EFFICIENT MONOCOT EMBRYO EXTRACTION AND PRESERVATION METHODS AND NOVEL USES THEREOF

CROSS-REFERENCE TO RELATED APPLICATIONS

This application claims priority to U.S. Provisional Application No. 62/863,687, filed Jun. 19, 2019, which is incorporated herein by reference in its entirety.

STATEMENT REGARDING FEDERALLY SPONSORED RESEARCH

Not applicable.

REFERENCE TO A SEQUENCE LISTING SUBMITTED VIA EFS-WEB

Not applicable.

BACKGROUND

Plant genetic transformation and gene editing are critically important methods for the field of agronomic research as well as advancing new traits of agronomic importance. Increased yield, nitrogen utilization, disease resistance, insect resistance, drought and heat tolerance, and nutritional improvement are just a few of the traits that are targets of these genome modifying techniques. Most methods of plant transformation and editing procedures are reliant on older "transformation competent" germplasm and are prone to tissue culture-induced mutations, creating unknown variables in the plant, complicating phenotypic selection. Additionally, current methods rely on preparation of competent germplasm tissues immediately prior to transformation due to the inability to store such tissues.

Therefore, a need exists for the development of storable germplasm tissues which are competent for a variety of transformation methods. Such a supply of storable tissues will create the potential for more rapid transformation of heterologous DNA of interest, as well as potentially increasing transformation efficiency.

SUMMARY OF THE INVENTION

In a first aspect, provided herein is a method for preparing a dried maize explant, the method comprising the step of: drying a maize embryo on a substrate at a temperature between about 4° C. and about 30° C. and at a relative humidity between about 20% and 60% until the maize embryo has an internal moisture content between about 2% and about 20%.

In some embodiments, the substrate it selected from the group consisting of filter paper, a solid gel, clay, perlite, or vermiculite. In some embodiments, the embryos is dried in the presence of desiccation medium comprising water, a tissue culture medium, or a sugar solution. In some embodiments, the sugar solution comprises sucrose, trehalose or raffinose. In some embodiments, the desiccation medium comprises plant growth regulators.

In some embodiments, the maize embryo is dried in the presence of a saturated salt solution to control relative humidity.

In some embodiments, the maize embryo is dried for between about 1 day and about 8 days. In some embodiments, the method additionally comprises the step of freezing the embryo at −20° C. In some embodiments, the method additionally comprises the step of rehydrating and germinating the dried embryo, whereby in a population of dried, rehydrated, and germinated embryos at least 65% of the embryos germinate.

In some embodiments, the maize embryo is sliced before drying.

In a second aspect, provided herein is a dried maize explant generated by the methods described herein.

In some aspects of the disclosure, the maize embryo is obtained from a maize ear by a method comprising the steps of: rinsing the maize ear with ethanol; surface sterilizing the maize ear in a bleach solution; dipping the surface sterilized maize ear in a Vitamin C solution to remove residual bleach; removing the outer facing seed coat from kernels on the maize ear; removing the kernels from the maize ear; separating the maize embryos from cell exudate and contaminates associated with the removed kernels. In some embodiments, the maize ear is covered by a husk and prior to rinsing the maize ear, the outer surface of the husk is disinfected with ethanol and removed from the maize ear. In some embodiments, the maize ear is surface sterilized in a bleach solution for between about 1 minute and about 45 minutes. In some embodiments, the kernels are removed from the maize ear using a field corn sheller or a popcorn sheller. In some embodiments, the method additionally comprises the step of grinding the removed kernels prior to separating the maize embryos from the cell exudate and contaminates.

In a third aspect, provided herein is a method of transforming a maize explant, the method comprising the steps of: rehydrating a dried maize explant generated by the methods described herein in a tissue culture medium; transforming leaf base tissue in the explant using force treatment and *Agrobacterium*-mediated transformation; inducing bud formation in the presence of a selectable marker; and regenerating shoots from the transgenic buds positive for the selectable marker. In some embodiments, the force treatment is selected from the group consisting of centrifugation, increased pressure, sonication, vacuum infiltration, desiccation, and nanoparticle exposure. In some embodiments, the selectable marker is glyphosate, bialaphos, basta, glufosinate, imazapyr, or G418 (geneticin). In some embodiments, bud formation is induced using a culture medium with a high cytokinin to auxin ratio.

In a fourth aspect, provided herein is a method for preparing a dried monocot explant, the method comprising the step of: drying a monocot embryo on a substrate at a temperature between about 4° C. and about 30° C. and at a relative humidity between about 20% and 60% until the monocot embryo has an internal moisture content between about 2% and about 20%.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 13 shows testing of mechanically extracted maize embryos. Top: mechanically extracted maize embryos dried in MgNO3. Bottom left: Defrost and rehydrated mechanically extracted maize embryo. Bottom right: maize embryo viability test with tetrazolium.

FIG. 16 shows barley shoot tip health derived from seed at either 12% or 10% internal moisture after co-culture (top left); after 1 week on delay media without PGRs (top right); and after 2 weeks on delay media with and without PGRs (bottom).

FIG. 21 shows barley shoot tips on delay media with varying cytokinin:auxin species and ratios.

FIG. 22 shows boxplots of percent responding barley shoot tips showing multiple bud/shooting phenotype at 2 weeks and cytokinin species and concentration (with either 0.5 or 1 ppm 2,4-D).

FIG. 23 shows a Gemcraft transgenic shoot derived from shoot tip inoculated with AGL1/pANIC 6A (induction on 2 mg/L BAP+1 mg/L 2,4-D; 4 g/L agarose I, 20 mg/L hygromycin).

FIG. 35 shows wild-type Gemcraft Barley (top); T1 Seedlings of Barley event WP412-1 (spikes 9-12, bottom left) and T1 Seedlings of Barley event WP412-3 (spikes 5-8, bottom right) 8 days post-planting.

FIG. 48 shows 24 DAP segregated transgenic T0 ear Hi2 outcrossed with native B73 pollen.

FIG. 49 shows imaging of embryos containing a marker.

INCORPORATION BY REFERENCE

Figure 1:
FIG. 1 shows germination of maize embryos plated on sterile tissue culture medium. Drying the immature embryos at 53% relative humidity (RH) yielded 68% germination (bottom) of dried, frozen, immature embryos while this germination rate dropped to 4% (top) when dried faster in a 25° C. dryer set at approximately 5% RH.

All publications, patents, and patent applications mentioned in this specification are herein incorporated by reference to the same extent as if each individual publication, patent, and patent application was specifically and individually indicated to be incorporated by reference.

DETAILED DESCRIPTION OF THE DISCLOSURE

The present disclosure describes methods for sterile extraction, drying, storage, and transformation of immature maize embryos. The present disclosure also describes a dried, storable, freezable immature value added maize explant.

Provided herein are methods for preparing a maize explant suitable for transformation from a maize seed, typically from the ear of the maize plant, or other monocot seed (e.g., *Sorghum*, rice, barley, and wheat). The maize explants (or other monocot explants) generated by the methods described herein have the capacity to be stored for longer periods of time than is currently possible using existing methods.

Currently, access to maize embryos and explants for use in transformation methods is limited to preparation of maize explants from seed tissues immediately prior to transformation. The methods described herein allow for high scale production of storable maize explants for more effect transformation methods. Additionally, the sterile embryo extraction methods described herein offer the unexpected benefit of being substantially free of residual fungal, bacterial, and viral pathogens, such as those that cause corn smut. Pathogen transfer is a problem experienced with currently practiced embryo extraction methods. Using the methods described herein, maize embryos can be extracted and transformed with a greatly reduced risk of transferring fungal, bacterial, and viral pathogens to the transformed plant from the plant from which the embryo was extracted. As described in further details below, the protocols described herein allow for targeted pretreatment of maize embryos and explants at various stages and with various factors to improve explant storage and transformation efficiency.

As used herein, "embryo" refers to part of a seed, consisting of precursor tissues (meristematic tissues) for the leaves, stem, and root, as well as one or more cotyledons. Once the embryo begins to grow (germinate), it becomes a seedling plant.

As used herein, "meristem" or "meristematic tissue" refers to the portion of a seed that consists of undifferentiated cells, the meristematic cells, which differentiate to produce multiple plant structures including stem, roots, leaves, germline tissues and seeds. The meristematic cells are the targets for transformation to obtain transgenic plants.

As used herein, "explant" refers to the target material for transformation.

As used herein, "germline transformation" refers to the transformation of a gene of interest into cells that give rise to pollen or ovule thus into seed.

In one aspect, provided herein is a method for the sterile extraction of a maize embryo.

The method for sterile extraction of a maize embryo generally includes the steps of disinfecting the outer surface of the husk of a maize ear with ethanol, removing the husk, silks, and poor quality kernels from the maize ear, disinfecting the maize ear with ethanol, surface sterilizing the maize ear with bleach, dipping the sterilized maize ear in a solution of Vitamin C, removing the outer facing seed coat from the kernels on the maize cob, separating the kernels, including the embryos, from the cob of the maize ear in the presence of a collection medium, and separating the embryos from the remaining kernels, starches, waste particles, cell exudate and contaminates. In some embodiments, following separation of the kernels from the cob and before separating the embryos, the kernels are ground.

A maize ear is provided which includes a central cob, kernels, silks, and an outer husk. The outer husk may be disinfected with ethanol allowed to dry prior to removal from the ear. In some embodiments, the husk is disinfected with between about 60% and about 100% ethanol (e.g., 60%, 70%, 80%, 90%, or 100%). In some embodiments, the husk is disinfected with between about 60% and about 100% isopropanol (e.g., 60%, 70%, 80%, 90%, or 100%). In some embodiments, the husk is disinfected with an aqueous surfactant detergent solution. After the disinfected husk is removed, the silks are also removed from the maize ear. The maize ear with both the husk and the silks removed is then washed with sterile water and poor quality kernels are removed.

The maize ear used in the methods described herein is obtained from a maize plant about 8 days to about 35 days after pollination (DAP) (e.g., 8, 9, 10, 11, 12, 13, 14, 15, 16, 17, 18, 19, 20, 21, 22, 23, 24, 25, 26, 27, 28, 29, 30, 31, 32, 33, 34, or 35 days after pollination) based on growth of the plant in a greenhouse. In some embodiments, the DAP may be longer for field grown maize based on the growing conditions. In some embodiments, the maize in field grown and the maize ear is from a maize plant about 8 to about 50 DAP, about 8 to about 60 DAP, or about 8 to about 70 DAP. The maize embryos should be extracted from the maize ear before the maize embryos mature. The maize ear are used while still in a hydrated state before the kernels and ears are dried. When the maize ears are in a hydrated state, the embryos are immature. Without being bound to any particular theory, it may be possible to quick dry the maize ears without maturing the embryos. In some embodiments, the maize ear is from maize genotypes B73, B103, LH244, PHR03, PHJ89, or PH207.

After removal of the husks and silks, the maize ear, including the surface of the kernels, is disinfected with ethanol then rinsed with water. In some embodiments, the ethanol is 70% ethanol. In some embodiments, the water is sterile water. In some embodiments, the water is sterile reverse osmosis deionized water (RO/DI water). In some embodiments, the maize ear is disinfected for about 1 minute.

After disinfection, the maize ear is surface sterilized with bleach then rinsed with water. In some embodiments, the maize ear is surface sterilized for between about 10 minutes and about 30 minutes. In some embodiments, the maize ear is surface sterilized for about 20 minutes. In some embodiments, the bleach is 10% Clorox™ bleach. The maize ear is then dipped in a Vitamin C solution to remove residual chlorine bleach. In some embodiments, the Vitamin C solution includes between about 10 ppm and about 2000 ppm Vitamin C in water (e.g., 10, 20, 50, 75, 100, 150, 200, 500, 750, 1000, 1500, or 2000). In some embodiments, the Vitamin C solution includes about 50 ppm Vitamin C in water. In some embodiment, the maize ear is dipped for about 1 minute in the Vitamin C solution.

The outer facing seed coat is removed from the kernels on the surface sterilized maize ear. The maximum amount of process debris is removed by cutting as deeply as possible into the kernel without damaging the embryo. The outer facing seed coat may be removed by any suitable means or with any suitable tool known in the art. In some embodiments, the outer facing seed coat is removed using a blade such as a razor blade, a scalpel, or a vegetable peeler. After the outer facing seed coat is removed, the remaining portion of the kernels and cob are rinsed with sterile water.

The kernels and embryos are removed from the cob into a collection medium. The kernels and embryos may be removed by shelling. The process of shelling includes separating the kernels, including the embryos, from the cob of the ear by popping each of the kernels off the cob. The shelling process may be done using a tool such as a field corn sheller or a popcorn sheller, which is twisted down the length of the cob to separate the kernels, including the embryos, from the cob. In some embodiments, the cob is shelled above the collection medium and the embryos and debris fall into the collection medium. In some embodiments, the cob is submerged in the collection medium during removal of the kernels and embryos. Shelling of the ear while submerged provides the advantages of immediately separating the embryos from debris, preventing the embryos and debris from attaching to the sheller and impeding the shelling process, and providing the embryos and debris in a liquid phase such that the embryos can be easily separated from starches and large debris.

The collection medium may be any sterile medium that supports the survival of the embryos. In some embodiments, the collection medium may include one or more agents to inhibit germination of the embryos. In some embodiments, the collection medium is sterile water. In some embodiments, the collection medium is a tissue culture medium. In some embodiments, the collection medium is high sugar maize infection medium. The collection medium may include factors including, but not limited to a germination inhibitor (e.g., abscisic acid, paclobutrazol, metolachlor, and other gibberellic acid inhibitors), sucrose, raffinose, trehalose, mineral salts (e.g., murashige and skoog (MS) salts and Gamborg's B5 (GB5) nutrients), glycine-betaine, amino acids, amino acid derivatives, fungicides, antibiotics, ethylene inhibitors (e.g., silver nitrate silver thiosulfate, ethephone, 1-methylcyclopropene, and aminoethoxyvinylglycine), a factor specific to a selectable marker (e.g., glyphosate), mutagens (e.g., ethyl methanesulfonate), and haploid doubling agents (e.g, colchicine and other polyploidy induction chemicals).

In some embodiments, the mixture of material removed from the cob in the collection medium, which includes kernels and embryos as well as other seed materials, is ground to rupture wet kernels. Suitable grinders include grinders that allow for some separation of the grinding surfaces and can be easily cleaned and sanitized. In some embodiments, the mixture in the collection medium is ground using a mechanical grinder, such as a QCG4E Electric Disk Grinding Mill. In some embodiments, the mechanical grinder is a blender. In some embodiments, the grinding may be done by physical manipulation of the material such as by grinding, crushing, mashing, pressing, or squeezing the material by hand.

The embryos are then separated from the remaining kernels, starches, waste particles, cell exudate and contaminates. The kernels and embryos in the collection medium may be washed with sterile medium or sterile water to first remove starches and other small waste products. The first washing step may be carried out over a fine mesh filter such as a fine mesh fish net to allow small waste production to fall through. In some embodiments, the embryos are washed for about 30 to 40 seconds. The embryos are then poured over a series of sieves (e.g., #5, #6, #7, #8, #10, and #12 mesh sieves) to capture and separate the embryo based on size. In some embodiments, a #6 mesh sieve is used to capture 20-30 DAP embryos. In some embodiments, a #8 mesh sieve is used to capture about 15 DAP embryos. In some embodiments, a larger mesh sieve, such as a #4, #5, or #6 mesh sieve is used to remove larger kernel debris. It is envisioned that a skilled artisan will be able to select the appropriate size mesh sieve or series of mesh sieves to separate the immature embryos. Mesh sieve sizing is standard in the art. The final resulting embryos may be washed in sterile water or sterile medium to remove any remaining cell exudate and contaminates.

Embryos extracted by the methods described herein may be immediately used in a maize transformation method, may be stored at 4° C. for up to one week, or may be further processed for long term storage.

Immature embryo extraction from other monocot species will be similar to maize. Cleaning and washing steps will be the same as those described above for maize. The storage process will also be the same. For rice (*Oryza sativa* L.), oat (*Avena sativa* L.), rye (*Secale cereale* L.), Sorghum (*Sor-

*ghum bicolor* L.), barley (*Hordeum vulgare* L.), and wheat (*Triticum aestivum* L.), embryos are separated from the seed head and screened based on size as described above. The seed head, seeds, and removed materials are washed, surface sterilized, rinsed and ruptured in a grinder or mill as described above. A skilled artisan will be able to determine a suitable grinding gap for a mechanical grinder based on the size of the seeds and embryos of each species. Recovery of the embryos from the ground or milled materials will follow the same process described for maize.

The maize embryos or monocot embryos extracted by the methods described herein may be described as immature value added explants (iVAE). The value added explants are characterized as such because the tissue is metabolically active upon extraction and can immediately be used for transformation, dried down, used for embryo rescues, etc. These maize iVAE and monocot iVAE are also very clean after extraction, which, unlike embryos extracted from dry or imbibed mature caryopses, means these iVAE can be used for axenic cultures with significantly reduced risk of contamination.

In some embodiments, at any stage of the extraction, drying, or transformation methods described herein, the embryos may be imaged and/or sorted. For example, a visual marker gene is commonly used during haploid production in maize so that diploid embryos may be distinguished from haploid embryos. In this case, the haploid inducer parent carries a gene which makes the embryo, the endosperm, and the aleurone of diploid progeny purple. When haploid is successfully induced, the embryo will be colorless but the endosperm and the aleurone will be purple. Identification of the haploid embryos is generally done with a technician sorting them by hand. By removing the embryo from the kernel using the extraction methods described herein, it would be less ambiguous if one were to sort clear haploid embryos from purple diploid embryos.

In some embodiments, provided herein is a method for preparation of a mature monocot embryo explant. In general, a monocot seed is surface sterilized using bleach (e.g., 20% bleach for about 5 minutes) and the embryonic axis of the monocot seed is excised from the seed using any suitable means known in the art. For example, the embryonic axis may be removed by machine or by hand. The radical of the embryo may be removed from the shoot tip, and the mature embryo tissue of the shoot tip is used for mature monocot embryo explant generation. In some embodiments, prior to embryo extraction form the seed, the internal moisture content of the seed is between about 1% and about 14%, preferably between about 7% and about 10%. In some embodiments, prior to embryo extraction the monocot seed may be dried under a laminar flow wood prior to surface sterilization to achieve 8-14% internal moisture content. In some embodiments, prior to embryo extraction the monocot see may be dried using a desiccation method as described herein to achieve about 8% to about 14% internal moisture content.

Provided herein is a method of controlled desiccation of a maize embryo (or other monocot embryo) to prepare a dried immature maize embryo. Moisture removal from the maize embryo is carried out at a controlled temperature and a controlled moisture rate loss. Without wishing to be bound by any particular theory, removing moisture too rapidly results in killing the embryo while moisture removal too slowly results in germination of the embryo. The temperature of the controlled desiccation is between about 0° C. and about 30° C. (e.g., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., or 30° C.). Control of moisture rate loss may be accomplished in a number of ways including, but not limited to, desiccating the embryos under controlled relative humidity, desiccating the embryos on a moisture controlled substrate, desiccating the embryos in the presence of a desiccation medium, desiccating the embryos in a rapidly flowing stream of air (e.g., in a sterile tissue culture hood or flow hood), desiccating the embryos in a drying oven, or combinations thereof. In some embodiments, the relative humidity is controlled using saturated salt solutions. In some embodiment, during desiccation, the relative humidity (RH) is controlled between about 0% and about 80% (e.g., 0%, 5%, 10%, 15%, 20%, 25%, 30%, 35%, 40%, 45%, 50%, 55%, 60%, 65%, 70%, 75%, or 80%). The embryos are typically dried until the moisture content is about 10% (e.g., 5%, 6%, 7%, 8%, 9%, 10%, 11%, 12%, 13%, 14% or 15%). In some embodiments, the embryos are dried until the internal moisture content is less than 20%, less than 15%, less than 12% or less than 10%. In some embodiments, the internal moisture content is between about 2% and about 20%. In some embodiments, the embryos are dried for between about 1 day and about 8 days, between about 2 days and about 7 days, or between about 3 days and about 5 days.

Provided herein is a method of controlled desiccation of a monocot mature or immature embryo explant to prepare a dried mature or immature monocot explant. Moisture removal from the mature monocot embryo is carried out at a controlled temperature and a controlled moisture rate loss. The moisture removal may be carried out using any desiccation method as described herein, for example, the methods generally described above for maize embryo desiccation.

The use of saturated salt solutions to control relative humidity is known and described in the art. See, for example, Wexler et al. ("Relative humidity-temperature relationships of some saturated salt solutions in the temperature range 0° C. to 50° C.," 1954, Journal of Research of the National Bureau of Standards, 53(1), Research Paper 2512), Greenspan ("Humidity Fixed Points of binary saturated aqueous solutions," 1977, Journal of Research of the National Bureau of Standards, 81A(1):89-96), and Young et al. ("Humidity control in the laboratory using salt solutions—a review," 1967, Journal of Chemical Technology and Biotechnology, 17(9):241-245). In some embodiments, the saturated salt solution may include, but is not limited to, magnesium nitrate or potassium acetate.

In some embodiments, the embryos are desiccated on a substrate. The substrate may be, but is not limited to, filter paper, a solid gel, or a solid matrix (i.e., plastic beads, plastic particles, diatomaceous earth, clay, perlite, ground organic substrates (such as cellulose, nutshells, or vermiculite).

In some embodiments, the embryos are desiccated in the presence of a desiccation medium. The medium may include, but is not limited to, water, a tissue culture medium, a sugar solution, or combinations thereof. The sugar solution may include trehalose, raffinose, or combinations thereof. In some embodiments, the desiccation medium may include plant growth regulators.

In some embodiments, the embryos are sliced prior to drying. In some embodiments, the embryos are sliced manually using a razor blade or scalpel. In some embodiments, the embryos are machine sliced. In some embodiments, microholes are added to the embryo with a laser, nanoparticles, or fine needles. In some embodiments, the surface abrasion is used on the embryo using particles, cold plasma, or chemical.

In some embodiments, the embryos are provided on filter paper moistened by a desiccation medium. In some embodiments, the embryos are desiccated at 23° C. and 23% relative humidity controlled using a saturated solution of potassium acetate. In some embodiments, the embryos are desiccated at 23° C. and 53% relative humidity controlled using a saturated solution of magnesium nitrate.

In some embodiments, embryos are provided on a solid gel, such as a solid plant tissue culture medium. The solid gel or solid tissue culture medium may include sugars or plant growth regulators as described herein. The embryos on the solid gel are desiccated under a rapidly flowing stream of air, such as in a sterile tissue culture hood (e.g., Class 1 Clean Air Cabinet), at a controlled relative humidity between about 0% and about 80% depending on seasonal influences and building intake air and at a temperature between about 20° C. and about 25° C. Without wishing to be bound by any particular theory, it is believed that the solid gel acts as a ballast to slow the loss of moisture from the embryos.

In some embodiments, the embryos are provided with a solid matrix such as clay, perlite, or vermiculite suspended in a desiccation medium. The solid matrix is added to embryos suspended in a desiccation medium and the resulting mixture is spread out on a dish and allowed to dry in a sterile tissue culture hood. The embryos provided with a solid matrix may be dried as previously described. The embryos may be dried in a laminar flow hood at a temperature between about 20° C. and about 25° C. at a controlled relative humidity between about 0% and about 80% depending on seasonal influences.

After the embryos are dried, they may be frozen and stored between about −10° C. and about −80° C. In some embodiments, the dried, frozen embryos are stored at about −20° C. The dried, frozen embryos may be stored for at least a day, at least 2 days, at least 4 days, at least 7 days, at least 14 days, at least 21 days, or at least one month. In some embodiments, the dried, frozen embryos may be stored for at least one year.

Dried, frozen embryos may be rehydrated and germinated. In some embodiments, rehydration of the dried, frozen embryos using tissue culture medium resulted in a germination rate of at least about 50%, at least about 60%, at least about 65%, at least about 70%, at least about 80%, at least about 90%, or at least about 95%. In some embodiments, the germination medium is Gamborg's B5 medium or a variant thereof. Other convention tissue culture media known in the art for seed germination may also be used.

Provided herein is a method to transform maize or monocot embryos. Maize or monocot embryos to be transformed may be embryos freshly excised from maize/monocot ears and seeds, hydrated embryos that have been stored after excision, or embryos that have been dried as described herein. Maize or monocot embryos can be transformed with a heterologous gene or nucleic acid of interest by any means known in the art. Various methods have been developed for transferring genes or nucleic acids into plant tissue including particle bombardment, high velocity microprojection, microinjection, electroporation, direct DNA uptake, and bacterially-mediated transformation. Bacteria known to mediate plant cell transformation include a number of species of the Rhizobiaceae, including, but not limited to, *Agrobacterium* spp., *Sinorhizobium* spp., *Mesorhizobium* spp., *Rhizobium* spp., and *Bradyrhizobium* spp. In some embodiments, the maize embryo is transformed using *Agrobacterium* spp. In some embodiments, the embryo is transformed using particle bombardment using gold microcarriers. Suitable methods of plant transformation are described in the art, such as, for example, by Frame et al. (Frame, Bronwyn R. et al., "Maize (*Zea mays* L.)," chapter in *Agrobacterium* Protocols, Volume 1, Methods in Molecular Biology, pages 185-200), Frame et al. ("Genetic transformation using maize immature zygotic embryos," 2010, Plant Embryo Culture, pages 327-341), and Zhang et al. ("Transformation of recalcitrant maize elite inbreds using in vitro shoot meristematic cultures induced from germinated seedlings," Plant Cell Reports, 2002, 21(3):263-270).

The heterologous gene or nucleic acid of interest may be any gene or nucleic acid which may confer a particular desirable trait or phenotype in the transformed plant. Examples of suitable genes of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including starch production, modified oils production, high oil production, modified fatty acid content, high protein production, fruit ripening, enhanced animal and human nutrition, and biopolymers production. Also environmental stress resistance, pharmaceutical peptides and secretable peptides, improved processing traits, improved digestibility, low raffinose, industrial enzyme production, improved flavor, nitrogen fixation, hybrid seed production, fiber production and biofuel production. Any of these or other genetic elements, methods, and transgenes may be used with the invention as will be appreciated by those of skill in the art in view of the instant disclosure. The heterologous gene or nucleic acid of interest may also be a sequence which can affect a phenotype of interest by encoding an RNA molecule that cases the targeted inhibition of expression on an endogenous gene via gene silencing technologies.

The heterologous gene or nucleic acid of interest may be transformed in the form of a vector. Any suitable vector design known in the art may be used with the explants of the present invention. In some embodiments, the vector will additionally include one or more selectable or screenable markers. The selectable or screenable marker may confer upon the plant tissue resistance to an otherwise toxic compound. A number of screenable or selectable markers are known in the art and can be used in the present invention. The screenable marker may be fluorescent (e.g., RFP) or non-fluorescent (e.g., GUS). More than 20 selectable marker genes have been reported in the transformation of higher plants (Komari T, Takakura Y, Ueki J, Kato N, Ishida Y, Hiei Y (2006) Binary vectors and super-binary vectors. In: Kan Wang (ed.), and *Methods in Molecular Biology, vol. 343: Agrobacterium Protocols*, Vol. 1, Second Edition. Humana Press Inc., Totowa, NJ, pp. 15-41).

The vector may also include a suitable promoter. Suitable promoters are described in the art and known to a skilled artisan. Suitable promoters for expression in plants include, without limitation, the 35S promoter of the cauliflower mosaic virus, ubiquitin, tCUP cryptic constitutive promoter, the Rsyn7 promoter, pathogen-inducible promoters, the maize In2-2 promoter, the tobacco PR-1a promoter, glucocorticoid-inducible promoters, estrogen-inducible promoters and tetracycline-inducible and tetracycline-repressible promoters. Other promoters include the T3, T7 and SP6 promoter sequences, which are often used for in vitro transcription of RNA, U3, U6, Actin, figwort mosaic virus (FMV), sugarcane bacilliform virus (SCBV), banana streak virus (BSV), and commelina yellow mottle virus (CYMV) promoters.

Prior to inoculation, dried embryos to be transformed may be rehydrated using suitable tissue culture medium. In some embodiments, the rehydration medium is Soy INO medium, VAE rehydration medium, or a solid medium such as Basal MS or Gamborg's B5 medium. In some embodiments, the rehydration step includes incubation of the dried embryo in a sugar solution or a salt solution. In some embodiments, the dried embryo is rehydrated by exposure to high humidity. In some embodiments, the rehydration step is combined with the pretreatment step described below.

Embryos may be pretreated prior to inoculation and transformation. In some embodiments, the embryos are pretreated with a polyethylene glycol (PEG) ethanol solution. In some embodiments, the PEG-ethanol solution includes about 20% PEG4000 in about 70% ethanol. In some embodiments, the embryos are pretreated in the PEG-ethanol solution for between about 10 seconds and about 10 minutes (e.g. 10 s, 20 s, 30 s, 45 s, 1 min., 1.5 min, 2 min, 5 min, 8 min, or 10 minutes). In some embodiments, salts may be added to the PEG-ethanol solution. In some embodiments the PEG-ethanol solution includes Murashige and Skoog (MS) salts. In some embodiments, the pretreatment step includes sonication, vortexing, centrifugation, heat-shock, exposure to high pressure, or addition of chemicals (e.g., TDZ, glyphosate, or metolachlor).

In some aspects, maize embryos are transformed by a method including the steps of transforming leaf base meristematic tissue on the embryo, inducing bud formation in the presence of a selectable marker, and regenerating shoots from the transgenic buds positive for the selectable marker.

In some embodiments, leaf base tissue in the embryo is transformed using force treatments. Force treatments may include, but are not limited to, centrifugation, increased pressure, sonication, vortexing, abrasion of the embryo surface (e.g., vortexing with silicon carbide fibers to pierce tissue), vacuum infiltration, desiccation, alternating between vacuum and high pressure, or combinations thereof. In some embodiments utilizing Agrobacterium mediated transformation, the force treatment may be done prior to or in the presence of the Agrobacterium. In some embodiments, the force treatment is centrifugation at a speed between about 5000×g and about 8000×g. In some embodiments, the force treatment is carried out in the presence of INO medium. Force treatment transformation methods are described in the art. See, for example, Khanna, et al. ("Centrifugation assisted Agrobacterium tumefaciens-mediated transformation (CAAT) of embryogenic cell suspensions of banana (Musa spp. Cavendish AAA and Lady finger AAA)," Molecular Breeding, 2004, 14:239-252), Kapila et al. ("An Agrobacterium-mediated transient gene expression system for intact leaves," Plant Science, 1997, 122(1):101-108), Trick et al. ("SAAT: sonication-assisted Agrobacterium-mediated transformation," Transgenic Research, 1997, 6(5): 329-336), Hiei et al. ("Improved frequency of transformation in rice and maize by treatment of immature embryos with centrifugation and heat prior to infection with Agrobacterium tumefaciens," Plant Cell, Tissue, and Organ Culture, 2006, 87(3):233-243). In some embodiments, the embryos are force treated prior to transformation and are rested for at least about 5 minutes, 10 minutes, 15 minutes, 20 minutes, 30 minutes, or 45 minutes prior to transformation.

TABLE 1

| WCIC INO medium: | |
|---|---|
| Ingredients and Notes | Amount to add per liter (grams) |
| Gamborg B5 Phytotechnology Laboratories G398 | 1.284 |
| Glucose | 30 |
| MES | 2.8 |
| pH to 5.4 with 1N KOH and autoclave | |

Bud formation is generally induced using medium with a high cytokinin to auxin ratio. A high cytokinin to auxin ratio in the medium is based on the concentration of plant growth regulators present (PGR) or the relative activity of the plant growth regulators on the explant. For example, a medium including 2-10 mg/L 6-benzylaminopurine (BAP) and 1 mg/L 2,4-dichlorophenoxyacetic acid (2,4-D) would have a high cytokinin to auxin ration. In another example, the medium can include 1-2 mg/L thidiazuron and 1 mg/L 2,4-D. In some embodiments, the BAP is provided in the medium at a concentration of at least 13 µM. In some embodiments, the BAP is provided at a concentration of 0.2 µM for maintenance of the culture. In some embodiments, the culture is completely free of auxin. In some embodiments, $Cu^{2+}$ and $Zn^{2+}$ are added to improve shoot proliferation. In some embodiments, maltose is added to improve growth, particularly in grasses. Additional techniques to induce bud formation include, but are not limited to, treatment with herbicidal compounds such as thidiazuron (TDZ) or glyphosate, chemical conditioning with ethanol, polyethylene glycol, potassium hydroxide or combinations thereof, treatment with compounds such as paclobutrazol (PBZ) (e.g., sold under the trade names Paczol or Bonzi) to inhibit GA3 synthesis, treatment with compounds such as NPA to disrupt auxin transport, or combinations thereof.

In some embodiments, maize embryos are transformed using the expression of the morphogenic regulating Baby boom (Bbm) and wuschel2 (Wus2) genes, which, when expressed in immature embryos increase the transformation efficiency due to an increase in embryogenic tissue growth. In some embodiments, Bbm and Wus2 are expressed from a separate vector than the nucleotide of interest. In some embodiments, Bbm and Wus2 are part of the same vector including the nucleotide of interest. In either case, Bbm and Wus2 mediate formation of somatic embryos from the transformed cells. Somatic embryos can then be regenerated and selected for based on the selectable marker specific to the nucleotide of interest. The target tissue may be intact embryos, embryos that are diced to expose the meristematic and leaf whorl tissues, or embryos with the scutellum removed.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

Unless defined otherwise, all technical and scientific terms used herein have the same meaning as commonly understood by one of ordinary skill in the art to which the invention pertains.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates the wet extraction of immature maize embryos. Specifically, this embodiment demonstrates wet extraction of 2.5 mm plus (20 to 30 DAP) immature embryos of B73, and other maize genotypes, for collection of storable immature embryos.

Hand Shell Method—
1. Disinfect the husk of the maize with 70% ethanol and allow to dry prior to removal. This step helps prevent contamination of the kernels during the de-husking process. After husk removal, clean off silks, wash and remove poor quality kernels from ears.
2. Spray the cob with 70% ethanol, allow to sanitize for 1 minute. Rinse with sterile RO/DI water.
3. Surface sterilize cobs of 15 to 30 DAP B73, or other genotypes, for 20 minutes in 10% household Clorox bleach. Rinse well in sterile water. Dip in sterile water containing 50 ppm Vitamin C for 1 minute (this step removes residual toxic chlorine bleach). Drain.
4. Fill a deep sterile pan with sterile water. A different collection medium may be selected if desired, for instance a type of modified tissue culture medium.
5. Working on sterile paper, remove the outer facing seed coat from the kernels on the cob using a sanitized potato peeler. A scalpel may also be used to accomplish this task. To remove maximum process debris, cut as deeply as possible without damaging the embryos. Toss all debris and rinse prepared cobs enter a strong flow of sterile water before adding them to the pan of sterile water for shelling.
6. Using long (full coverage of wrists) sterile gloves (spray new, clean disposable nitrile gloves with 70% ethanol if sterile gloves are not available), "shell" the cobs under sterile water using a sterile "field corn sheller" or "popcorn sheller" based on the diameter of the cobs. Continue shelling each additional ear. Wash the shelled cobs in the sterile collection fluid to remove all embryos prior to discarding the empty cobs.
7. Pour the extracted cobs into a sterile fine mesh fish net and wash the material for 30 to 40 seconds under a strong flow of sterile water. This step removes starches and other waste particles small enough to pass through the fish net.
8. Pour extract through a sterile #6 sieve. Captured all material that passed through the #6 on a sterile #8 or #10 sieve. Select as appropriate. Discard the material retained on the number 6 sieve.
9. Wash the retained embryos on the #8 or #10 sieve in sterile RO/DI water. This step removes small particles that were originally retained in the fish net.
10. Transfer to a sterile fish net for final washing for 30 to 40 seconds under a strong flow of sterile process water. This step removes additional cell exudate and contaminates. Additionally, the fish net allows easy transfer of the collected product to collection vessels or drying steps. Embryo yield have been measured in the range of 70% to 90%.

Example 2

The embodiment described here demonstrates the wet extraction of immature maize embryos. Specifically, this embodiment demonstrates wet extraction of 2.5 mm plus (20 to 30 DAP) immature embryos of B104, and other maize genotypes, for collection of storable immature embryos.

Hand Shell and QCG4E Grain Mill Method—
1. Disinfect the husk of the maize with 70% ethanol and allow to dry prior to removal. This step helps prevent contamination of the kernels during the de-husking process. After husk removal, clean off silks, wash and remove poor quality kernels from ears.
2. Spray the cob with 70% ethanol, allow to sanitize for 1 minute. Rinse with sterile RO/DI water.
3. Surface sterilize cobs of 15 to 30 DAP B104, or other genotypes, for 20 minutes in 10% household Clorox bleach. Rinse well in sterile water. Dip in sterile water containing 50 ppm Vitamin C for 1 minute (this step removes residual toxic chlorine bleach). Drain.
4. Fill a deep sterile pan with sterile water.
5. Using long (full coverage of wrists) sterile gloves (spray gloves with 70% ethanol if sterile gloves are not available), "shell" the cobs under sterile water using a sterile "field corn sheller" or "popcorn sheller" based on the diameter of the cobs. Continue shelling each additional ear. Rinse each ear in the collection pan before discarding the shelled cob.
6. Extracted material was ground wet, with a small stream of sterile water to serve as a lubricant, in a QCG4E Electric Disk Grinding Mill (Quaker City Grinding Systems, LLC). The mill had the coarsest disk set and the "dry grain" feed auger installed. This auger was selected to slow passage of viable grain through mill. The dry product feed auger has slightly squared blades, as opposed to the wet product feed auger with smooth, rounded blades. Calibration of disk gap was adjusted to just engage product enough to rupture wet corn kernels.
7. Ground product was wet sieved in sterile water through a #8 sterile sieve. Product passing through #8 was collected on a #10 sieve and retained after being washed in large quantities of sterile water. Material retained on the #8 sieve was discarded. Actual embryo size may require alternative sieves for collection.
8. Transfer to a sterile fish net for final washing for 30 to 40 seconds under a strong flow of sterile process water. This step removes additional cell exudate and contaminates. Additionally, the fish net allows easy transfer of the collected product to collection vessels or drying steps. Embryo yield have been measured in the range of 70% to 90%.

Example 3

The embodiment describe herein demonstrates moisture removal and storage of axenic immature embryos.

Drained embryos prepared as in Examples 1 and 2 may be used immediately or may be stored in a 4-degree Celsius refrigerator, hydrated, for up to a week prior to use. However, long term storage has been achieved via controlled desiccation of the embryos. Several methods have been developed but all employ a similar approach, moisture removal needs to be accomplished at a controlled temperature and at a controlled moisture loss rate. Successful temperatures are in the range of 4° C. to 30° C. Three exemplary methods are described for controlling the rate of moisture loss from the immature embryos.

Embryos are spread evenly on moist filter paper. The moisture used for the filter paper and to temporally disperse the embryos may be optimized for conditions and may be sterile water, a tissue culture medium, a solution of stabilizing sugars such as but not limited to trehalose or raffinose. Plant growth regulators (PGRs) have been used for successful batches, as well. Embryos thusly distributed on moist filter paper can then be dried slowly at room temperature in closed, sterile environments at either 53% relative humidity (RH) or 23% RH using saturated salt solutions calibrated for those conditions. We have used potassium acetate for 23% RH and magnesium nitrate for 53% RH. When embryos are completely dried, we can freeze the embryos at minus 20 Celsius and the embryos will revive and germinate when plated on sterile tissue culture media at conditions appropriate for maize germination. In one test, drying the immature embryos at 53% RH yielded 68% germination of dried, frozen, immature embryos while this germination rate dropped to 4% when dried faster in a 25 C dryer set at approximately 5% RH. (FIG. 1) The preliminary data suggests that the conditions of drying are critical for long term storage of immature embryos.

TABLE 2 iVAE Drying Medium - in addition to the medium outlined below, the drying medium may have increased concentrations of sucrose; the drying medium may include abscisic acid; sucrose may be replaced with trehalose; the sucrose may be replaced with raffinose; or combinations or the listed options.

| Reagent | 1 Liter Amount | Units |
| --- | --- | --- |
| MS Salts with vitamins | 4.43 | g |
| Sucrose | 30 | g |
| Cleary's Fungicide | 60 | mg |
| Agarose 1 | 8 | g |
| Casein Hydrolysate | 0.5 | g |
| pH | 5.7 | |
| After Autoclaving | | |
| Carbenicillian | 250 | mg |
| Cefotaxime | 125 | mg |

An alternative to filter drying is controlled drying on a solid gel. Embryos may be spread evenly on moist filter paper, but then transferred to a sterile gel, such as solid plant tissue culture medium. The medium may be formulated with stabilizing sugars and PGRs as described above. Plates thusly prepared have been successfully dried in a rapidly flowing stream of air (such as in a sterile tissue culture hood). The gel serves as a "ballast" to slow the loss of moisture from the embryos. Complete drying often occurs in 2 to 7 days. Fully dried embryos may be frozen and rehydrated successfully as described above.

An alternative to filter and gel drying is drying in a solid matrix such as clays or other inert materials. Once dried the embryos may be separated from the matrix by simple sieving. Embryos have been successfully dried in a matrix of sieved cryogenic perlite (CS-30 Dicapearl from Dicalite Management Group). Embryos have been dried by adding about 20 milliliters of prepared immature embryos to a sterile 120 ml sample cup. Add 30 ml of appropriate tissue culture media or sterile water. Swirl to mix. Add about 100 ml of sterile Dicapearl. The resulting matrix is mixed well and then spread on a dish and allow to dry slowly in a sterile tissue culture hood. Drying is usually completed in 7 days. Dried embryos can be frozen and then thawed and germinated as described above.

Example 4

The embodiment described herein demonstrates moisture removal and storage of axenic pre-sliced immature embryos. Example 3 demonstrates the drying process using non-modified immature embryos. Example 4 demonstrates a method for modification of the immature embryos prior to desiccation and storage. Embryos may be sliced, either manually with a scalpel or razor or by machine. The advantage of slicing at this point is that controlled micro slices will cause less damage to cells as dry embryos and seeds tend to be brittle, which can lead to shattering and imprecise sectioning. There may be an advantage to drying the embryos slightly to have achieve even more control of cell damage. Once slicing is accomplished, the embryo slices may be dried as described in Example 3.

Example 5

The embodiment described herein demonstrates wet extraction of immature maize embryos. Specifically, this embodiment demonstrates wet extraction of 0.9 to 3.0 mm (9 to 14 DAP) immature embryos of B73 and other maize genotypes for collection of storable immature embryos.

Hand Shell Method—

1. Disinfect the husk of the maize with 70% ethanol and allow to dry prior to removal. This step helps prevent contamination of the kernels during the de-husking process. After husk removal, clean off silks, wash and remove poor quality kernels from ears.

2. Spray the cob with 70% ethanol, allow to sanitize for 1 minute. Rinse with sterile RO/DI water.

3. Surface sterilize cobs of 9 to 12 to 14 DAP B73, or other genotypes, for 20 minutes in 10% household Clorox bleach. Rinse well in sterile water. Dip in sterile water containing 50 ppm Vitamin C for 1 minute (this step removes residual toxic chlorine bleach). Drain.

4. On sterile paper—cut off kernel seed coat with a sterile vegetable peeler (as if you were doing hand excision). Toss debris.

5. Rinse off the prepared cobs with sterile RO/DI water to remove maximal debris. This is the last water step.

6. Fill a deep sterile pan with approximately 5 liters of sterile Maize tissue culture media (high sugar infection media listed below, or a solution of 7% sucrose and 3.5% glucose).

7. Using long (full coverage of wrists) sterile gloves (spray gloves with 70% ethanol if sterile gloves are not available), "shell" the cobs under sterile extraction medium using a sterile "field corn sheller" or "popcorn sheller" based on the diameter of the cobs. Continue shelling each additional ear. Rinse each ear in the collection pan before discarding the shelled cob.

8. Pour extract through a sterile #14 sieve. Toss debris retained on the sieve. If there is too much debris you can break this up into two steps: first pass through a number 10 sieve and then the number 14 sieve. In both cases toss material retained on the sieves.

9. Captured all material that passed through the #14 sieve in a sterile 3-inch, fine mesh fish net. Embryos can be used immediately or stored in liquid tissue culture media in the refrigerator for at least about 1 to 3 days.

10. The yield of embryos should be in the 70% to 90% range.

11. Total media used to capture and wash, store embryos from 10 cobs should be 7 liters.

TABLE 3

High sugar infection medium:

| Ingredients added before autoclaving: | Amount Per Liter (grams) Unless otherwise noted |
|---|---|
| MS Salts WITH vitamins (Phyto Technology Labs #M519) | 4.41 |
| Sucrose (Fisher BP220-10) | 68.4 |
| Glucose | 36.0 |
| L-Proline (Caisson Labs #P015-100GM) | 1.36 |
| Cleary's Fungicide | 0.060 |
| Casein hydrolysate (SIGMA #22090-500G) | 0.10 |
| Total Volume (Liters) | 1.0 |
| Ingredients After autoclaving: | |
| Cefotaxime | 0.1 |
| Carbenicillin | 0.20 |
| 2,4-D (Milligrams) | 2.0 |

Example 6

The embodiment described herein demonstrates storage and transformation of immature value added explants (iVAEs).

Figure 2:
FIG. 2 shows germination of freshly machine-excised B73 immature value added maize explants (iVAE). Freshly machine-excised maize iVAE can be used immediately for transformation, dried down, or used for embryo rescue. Additionally, unlike embryos extracted from dry or imbibed mature caryopses, the maize iVAE can be used for axenic cultures with significantly reduced risk of contamination.
Figure 3:
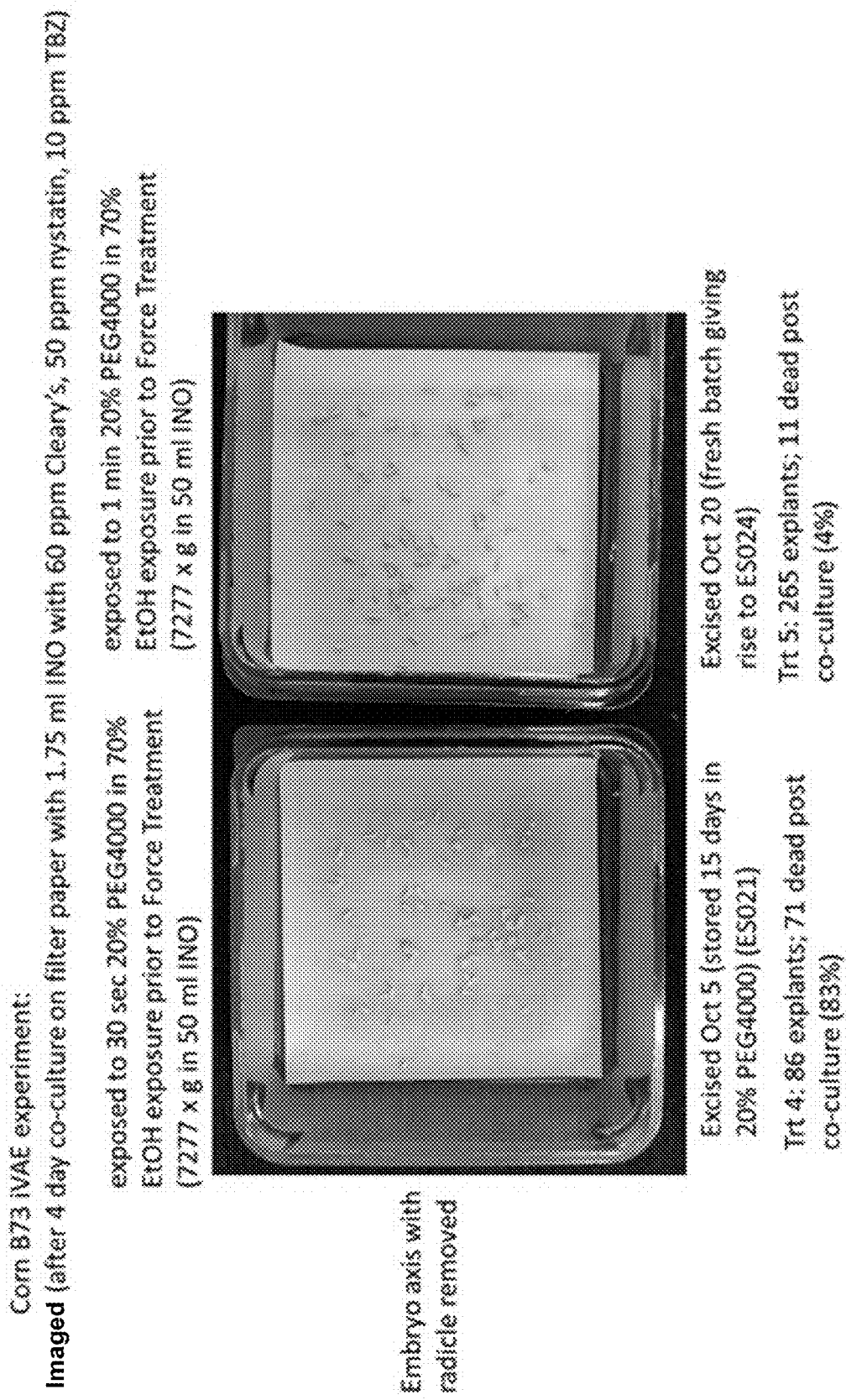
FIG. 3 shows images of maize embryos 4 days after force treatment transformation. Following force treatment transformation, embryos were co-cultured on filter paper with 1.75 ml WCIC Soy inoculation (INO) medium with 60 ppm Cleary's 3336 WP fungicide (also referred to as T-Methyl 50), 50 ppm nystatin, and 10 ppm triabendazole (TBZ). The image on the left shows maize embryos, which had previously been stored for 15 days in 20% PEG4000, that were exposed to a solution of 20% PEG4000 in 70% ethanol for 30 seconds prior to force treatment transformation (centrifugation at 7277×g in 50 ml INO medium). The image on the right shows freshly excised maize embryos that were exposed to a solution of 20% PEG4000 in 70% ethanol for 1 minute prior to force treatment transformation (centrifugation at 7277×g in 50 ml INO medium).
Figure 4:
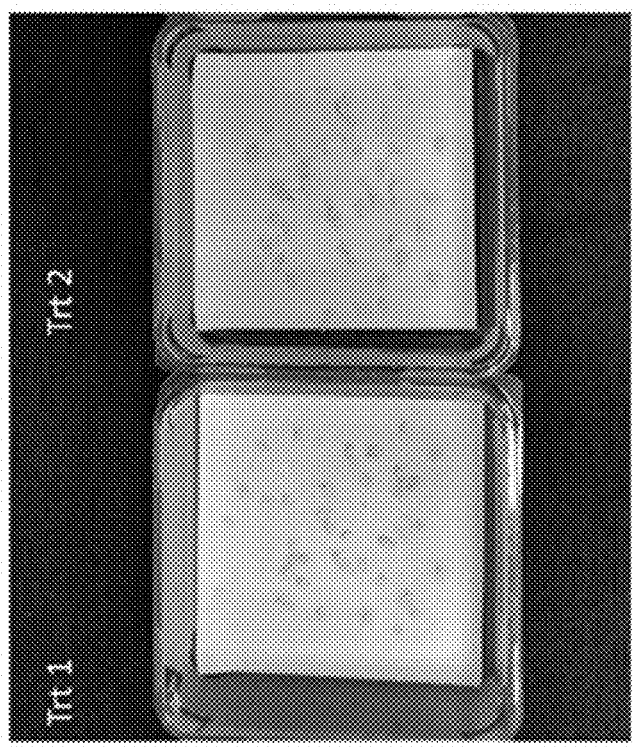
FIG. 4 shows images of maize embryos subject to *Agrobacterium* strain GV3101 mediated transformation with the binary plasmid VS224 (GV3101/VS224) after 4 days of co-culture on filter paper with 1.75 ml INO medium with 60 ppm Cleary's, 50 ppm nystatin, and 10 ppm TBZ. Transformation of cells occurs during infection and co-cultivation. The image on the left shows embryos that were stored for 1 week in a 20% PEG4000 solution and exposed to a solution of 20% PEG4000 in 70% ethanol for 30 seconds prior to co-culture. In the image on the right shows embryos that were stored for 1 week in a 20% PEG4000 solution with MS salts and exposed to a solution of 20% PEG4000 in 70% ethanol for 30 seconds prior to co-culture.
Figure 5:
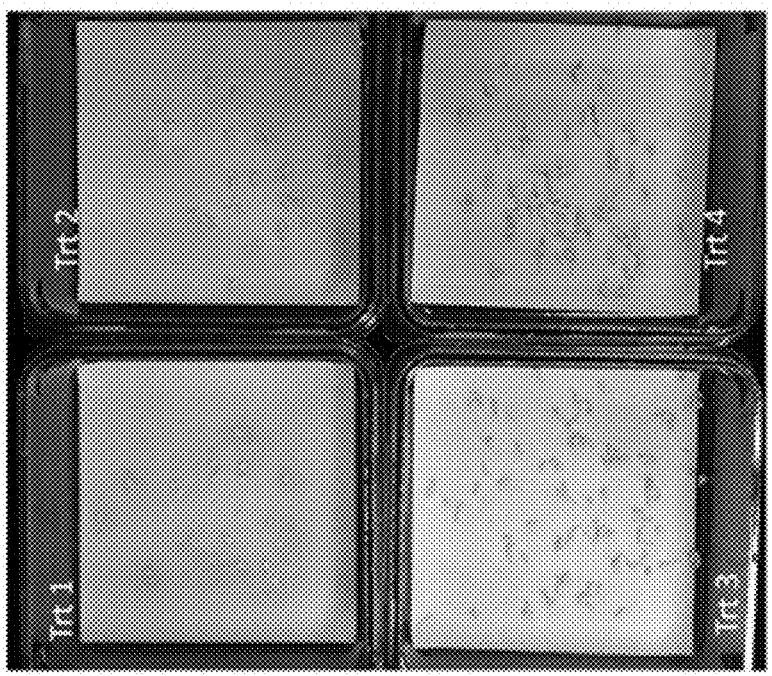
FIG. 5 shows images of maize embryos subject to *Agrobacterium* strain GV3101 mediated transformation with the binary plasmid VS224 (GV3101/VS224) after 4 days of co-culture on filter paper with 1.75 ml INO medium with 60 ppm Cleary's, 50 ppm nystatin, and 10 ppm TBZ. Transformation of cells occurs during infection and co-cultivation.

Freshly machine excised B73 iVAE explants were plated on B5 medium and imaged 4 days later (we observed 100% germination in this pilot test) (FIG. 2). The regenerative capacity of stored iVAEs can be improved by optimizing media components. For example, we exposed embryo axes derived from iVAEs to a solution of PEG4000 in 70% EtOH, then exposed them to a force treatment before inoculation with Agrobacterium (described below). We found storage of iVAEs in a 20% PEG4000 solution alone resulted in a large percentage of non-responding explants relative to freshly excised iVAEs (FIG. 3). However, addition of MS salts into the PEG storage medium could dramatically increase the percentage of responding explants (FIG. 4). The B5 medium includes Gamborg's B5 basal medium (salts & vitamins) (2.14 g), sucrose (20 g), Cleary's 3336 (50WP), and calcium gluconate (1.29 g) set to pH 5.8 than phytagel (3.5 g) is added and the mixture is autoclaved, then the antibiotics timentin (150 ppm) and cefotaxime (200 ppm) are added.

Agrobacterium-mediated transformation of monocots has generally relied on the immature embryo system whereby scutellar tissue of immature embryos is transformed, the transformed tissue is de-differentiated into embryogenic callus tissue using a tissue culture medium with relatively high auxin to cytokinin ratio, and then regenerating embryos and transformed plants from this callus. (Ishida, Y., Saito, H., Ohta, S., Hiei, Y., Komari, T., and Kumashiro, T. (1996) High efficiency transformation of maize (Zea mays L.) mediated by Agrobacterium tumefaciens. Nature Biotechnology (14) 745-750.) This system had been highly successful in monocot transformation but is severely genotype dependent in terms of germplasms that are capable of forming embryogenic callus. This system is also labor intensive and inefficient in terms of timing between inoculation and plants to soil. The immature embryos used in this system range from 8-15 DAP. (Ishida, Y., Hiei, Y., and Komari, T. (2007) Agrobacterium-mediated transformation of maize, Nature Protocols (2) 1614-1621.)

An alternate method of transforming monocot iVAEs avoids the use of callus generation and should therefore be less genotype dependent, is more rapid, and more amendable to automation. Our mature monocot embryo transformation strategy involves the following steps: (1) transform meristematic "leaf base" tissue; (2) induce multiple buds from these regions (breaking apical dominance) in presence of selection (with possibly a delay step); and (3) regenerate shoots from transgenic buds in presence of selection.

Transformation of leaf base tissue generally involves the use of force treatments (e.g., sonication) either before or during inoculation. Use of force in terms of transfection improvement has been shown in the monocot immature embryo system and in banana. (Khanna, H., Becker, D., Kleidon, J., and Dale, J. (2004) Centrifugation assisted Agrobacterium tumefaciens-mediated transformation (CAAT) of embryogenic cell suspensions of banana (Musa spp. Cavendish AAA and Lady finger AAB). Molecular Breeding (14) 239-252). Use of force is part of a more general strategy of accessing and improving the competence of leaf base meristematic cells in the monocot mature embryo. Several techniques can be tested to improve meristem competency: (1) centrifugation and/or pressure in the presence of Agrobacterium or prior to Agrobacterium exposure; (2) sonication, vacuum infiltration, desiccation; and (3) nanoparticles (including silica carbide fibers).

Figure 6:
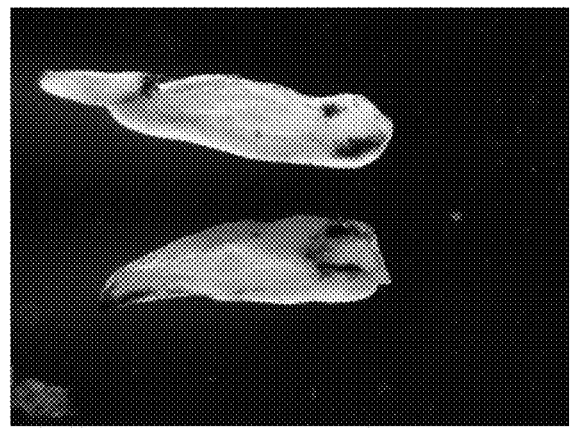
FIG. 6 shows transformation of leaf base meristematic tissue in immature maize embryos prepared and transformed by the methods described herein. Meristematic tissue was subject to *Agrobacterium* strain GV3101 mediated transformation with the binary plasmid VS224 (GV3101/VS224). The selectable marker is glyphosate resistance. The iVAE shown in FIG. 6 is from stored batch ES016. The embryo axis was removed from the scutellum and the radical portion removed. The explant was then subjected to 30 min 7277×g force in 50 ml INO medium, then incubated with GV3101/VS224 (scorable marker GUS, selectable marker maize optimized CP4) that was not induced with added acetosyringone. Explant was then co-cultured in 1.75 ml INO for 4 days at 23° C. 16/8 photoperiod.
Figure 7:
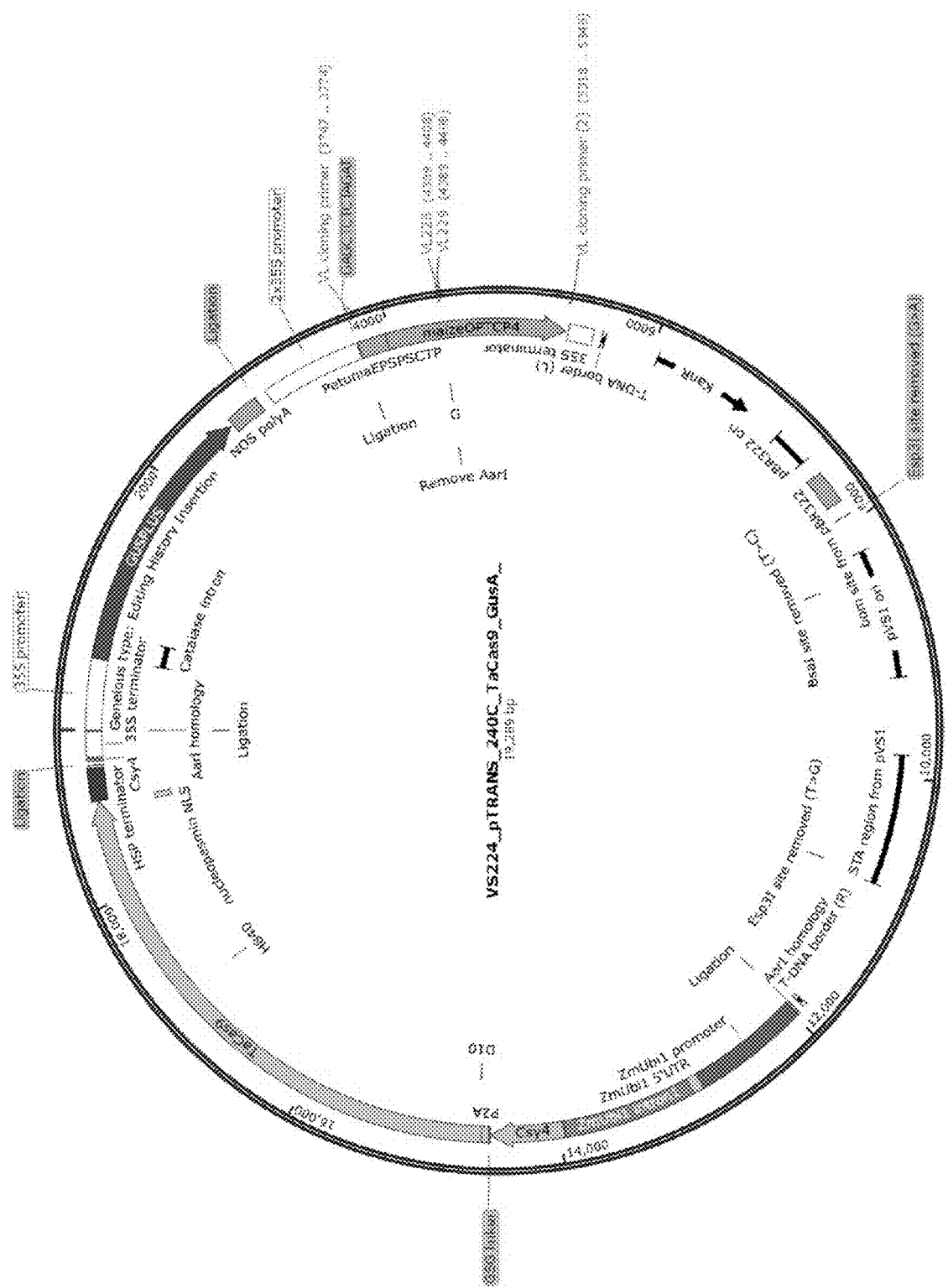
FIG. 7 shows the plasmid map of VS224, including the GUS marker and maize optimized CP4 marker, used for *Agrobacterium* mediated transformation of the embryos in FIGS. 3-6.
Figure 8:
FIG. 8 shows *Sorghum* seeds 3 days after plating on Gamborg's B5 medium.
Figure 9:
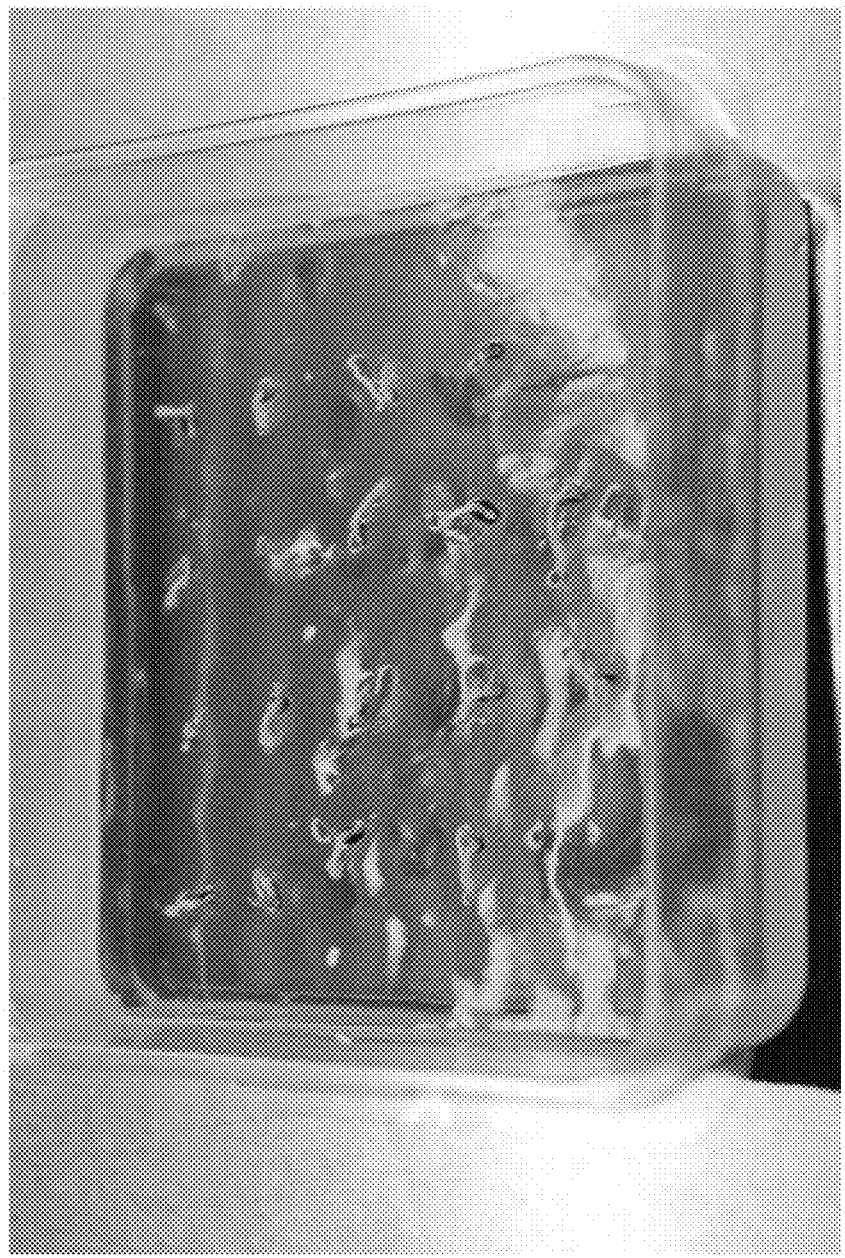
FIG. 9 shows *Sorghum* iVAEs 3 days after plating on Gamborg's B5 medium.
Figure 10:
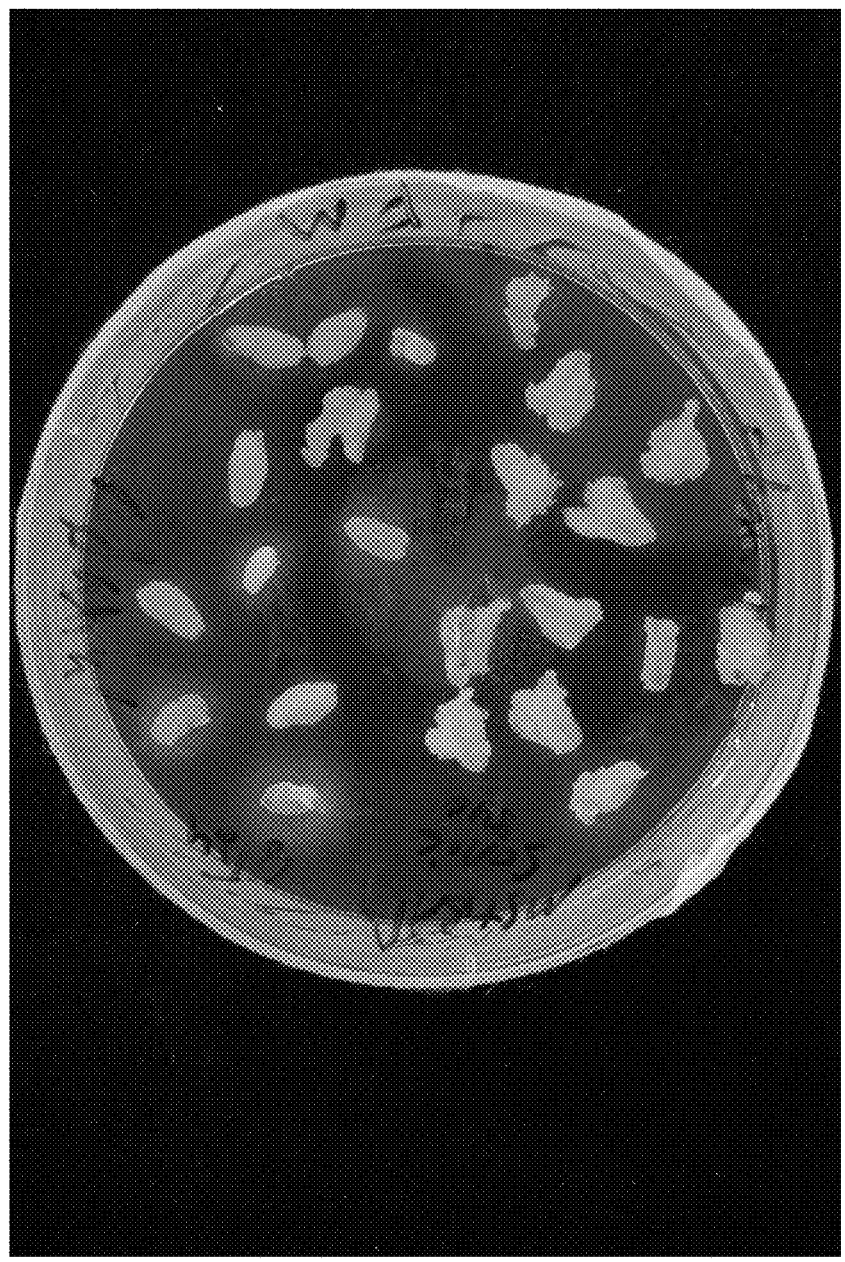
FIG. 10 shows 25 DAP maize embryos after a 10-minute ultrasonic bath, plated on MS+BAP. This figure corresponds to treatment 2a from Example 8.
Figure 11:
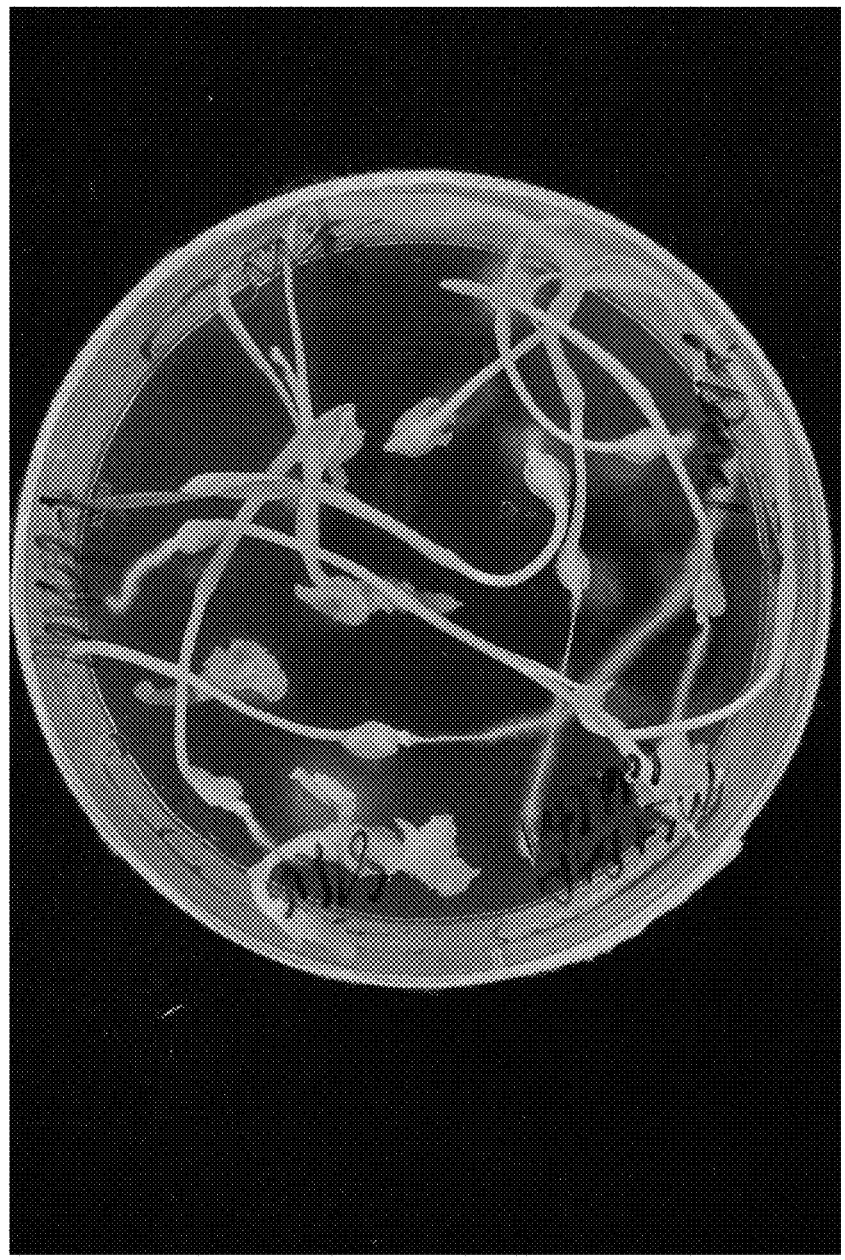
FIG. 11 shows cold control 25 DAP maize embryos plated on MS+BAP. This figure corresponds to treatment 3b from Example 8.
Figure 12:
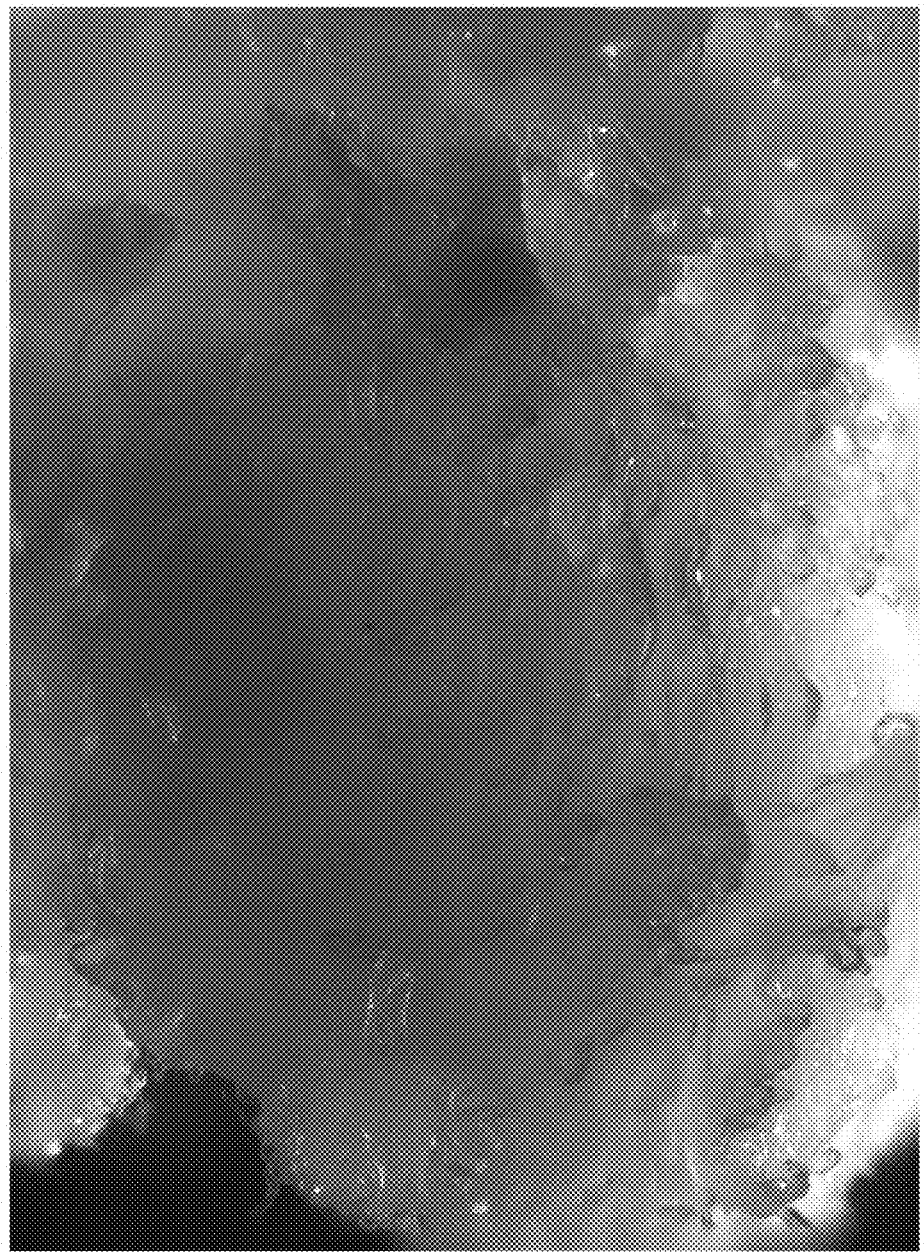
FIG. 12 shows a close up of the callus tissue after 19 days of growth.

Preliminary tests with B73 iVAEs (batch ES016) with scutella tissue removed exposed to 7277×g in 50 ml media immediately prior to inoculation indicate we can transform leaf base meristematic tissue (FIG. 6).

Multiple bud formation generally involves using medium with a relatively high cytokinin to auxin ratio, as demonstrated by regeneration studies performed by Zhong. (Zhong, H., Srinivasan, C., and Sticklen, M. B. (1992) In-vitro morphogenesis of corn (Zea mays L.). Planta (187) 483-489). This use of cytokinins is part of a more general strategy of suppressing apical dominance (suppressing germination response) in the mature corn explant. Several techniques can be tested to suppress germination, including but not limited to: (1) herbicidal compounds such as TDZ (which deactivates native cytokinin oxidases) and/or glyphosate; (2) chemical conditioning with ethanol, polyethylene glycol, potassium hydroxide, and/or any combinations of these; (3) compounds such as Paczol to inhibit GA3 synthesis; (4) compounds such as NPA to disrupt polar auxin transport; and (5) applying these techniques at the seed priming step, at the explant conditioning step, or both.

We have used glyphosate selection with internal WCIC binaries as well as hygromycin selection using pANIC binaries. (Mann, D. G. J., LaFayette, P. R., Abercrombie, L. L., King, Z. R., Mazarei, M., Halter, M. C., Poovaiah, C. R., Baxter, H., Shen, H., Dixon, R. A., Parrott, W. A., and Stewart, C. N. Jr. (2012) Gateway-compatible vectors for high-throughput gene functional analysis in switchgrass (Panicum virgatum L.) and other monocot species. Plant Biotechnology Journal (10) 226-236, Adams, W. R., Davis, B., Kucher, L., Martinell, B., Rout, J., Lowe, B.; Method and apparatus for substantially isolating plant tissues; May 10, 2011; US Patent: U.S. Pat. No. 7,939,325 B2).

An alternate approach to this multiple budding system involves the use of the morphogenic regulating Baby boom (Bbm) and wuschel2 (Wus2) genes. Expression of these genes in immature maize embryos has demonstrated increases in TF as well as an expansion of genotypes that are capable of being transformed, due to an enhancement of embryogenic tissue growth. (Lowe, Keith, et. al., (2016) Morphogenic Regulators Baby boom and Wuschel Improve Monocot Transformation. The Plant Cell (28) 1998-2015.) Activity of these genes has been observed in embryos up to 18 days after pollination (DAP), and has also been used in fully mature maize embryos. Using our current invention, we may be able to use immature embryos (including those beyond 18 DAP) that have been mechanically excised; stored; and transformed with the Bbm and Wus2 genes to induce embryogenic tissue.

Example 7

Sorghum RTX430 embryos were hand-excised and placed on 2×95 mm Whitman filters on a 100 mm Petri dish. 5 mL of mermaid extraction solution was added and the dish was placed in a shoe box with MgNO3 for drying. Dried explants were frozen for at least one week prior to regeneration. Regenerated Sorghum iVAEs (FIG. X) were compared to dry Sorghum seeds (FIG. X) each plated on Gamborg's B5 medium.

Seeds were compared to smallest Sorghum embryos tested. Sizes were assessed as follows: small—green panicles, kernel size too large for normal IE TF, approximately 3 mm; medium—green/yellow panicles, kernel size much too large for IE TF, approximately 3.5 mm; large—yellow/brown panicles, largest kernel size, likely near maturity, approximately 4 mm.

Example 8

25 DAP maize embryos were treated with 10 minute 45 kHz ultrasonic baths. These treatments seemed to inhibit germination and promote the formation of callus. 'Hot' control placed the embryos in a 35 C batch for 10 minutes, as that was the maximum temperature that the ultrasonic bath reached. 'Cold' control was at room temperature. The first experiments were performed with B73 and confirmed with maize genotypes H99 and PH207.

MS: MS salts and vitamins+Casein hydrolysate+2.5 mL/L cefotaxime. MS+BAP: MS+9 uM BAP 12 days after isolation:
Hot control
a. MS+BAP
  i. Adaxial side up—8/8 germinated.
  ii. Abaxial side up—6/8 germinated. 1/8 displays callus growth with no germination response.
  iii. Roots are generally shorter than shoots, but not always.
b. MS
  i. Adaxial side up—8/8 germinating.
  ii. Abaxial side up—7/8 germinating. 1/8 shows callus with no germination response.
  iii. Roots and shoots are both long. Callus visible in 3/16 explants.
Sonic
c. MS+BAP
  i. Aba—0/12 germinating. 12/12 show callus growth.
  ii. Ada—0/11 germinating. 3/11 show callus growth
d. MS
  i. Aba—0/9 germinating. 9/9 show callus growth.
  ii. Ada—1/11 germinating. 2/11 show callus growth.
  iii. One embryo on the adaxial treatment is oriented wrong
Cold Control
e. MS
  i. Aba—8/8 germinating. 0/8 callus.
  ii. Ada—6/8 germinating. 3/8 callus.
f. MS+BAP
  i. ABA—6/7 germinating. 1/7 callus.
  ii. Ada—8/8 germinating. 1/8 callus. Callus growth is from radicle-side of embryonic axis.

Example 9

Maize iVAEs (Immature Value-Added Explants) were prepared following the methods outlined below, and viability and glyphosate sensitivity of the dried, stored embryos were tested. These iVAEs were incubated for four days in a drying chamber with MgNO$_3$ saturated salts and then stored at s −20° C. These frozen iVAEs were later pulled from storage and used to determine process survival as well as used in an experiment to determine sensitivity to the herbicide glyphosate (Millipore Sigma Glyphosate "N-(Phosphonomethyl) glycine"; Cat #337757-5G) for future use as a selection agent for these novel explants.

20 DAP (days after pollination) B73 ears were collected from self-pollinated plants in the greenhouse. Immature embryos were extracted using the iVAE protocol; total number of embryos extracted was estimated at between 700 and 800. The extracted and cleaned embryos were placed in a drying chamber with MgNO3 saturated salts for 4 days. Plates were stored at 4° C. or −20° C. for 4 days.

Following storage, B73 embryos were rehydrated on Regeneration II medium. Embryos were rehydrated for 1 hour followed by an additional rehydration adding sterile water and collecting the embryos for the experiment, as per the protocol below ("Rehydrating dried sterile maize iVAEs")

Following rehydration, plates were set up using regeneration II medium and germination measurements and observations were taken on Days 1, 4, 18, 27, 35, 49, and 56. Embryos incubated on plates without glyphosate had shoots, which grew up to the lid of the plates. Explants on the 10 μM to 100 μM glyphosate plates present start to show contamination.

Maize embryo Viability test with tetrazolium (2,3,5-tryphenyl tetrazolium chloride (TTC)): Several embryos were placed in a 2 mL Eppendorf tube with 0.1% (w/v) of 2,3,5-tryphenyl tetrazolium chloride, a formazan dye, in water and incubated at room temperature for 1 hour, and mixed every 10 minutes. This dye is used routinely in the seed industry as a way to determine seed viability. Red or pink staining of tissues is indicative of living, metabolically active cells. The coloration is caused by the formation of an insoluble formazan in the metabolic active tissues (Cobb R D. 2,3,5-Triphenyl tetrazolium chloride as a viability indicator of seeds fumigated with methyl bromide. Proc Association Off Seed Anal Soc Commer Seed Technol. 1956; 46:62-6).

The tetrazolium chloride viability test showed that all embryos are living. More specifically, seven from eight embryos presented strong TTC staining in the embryo axis compared with the scutellum, which is an indication that the embryo axis presented as more metabolically active than the scutellum (FIG. 13). This was true even in embryos with damaged in the scutellum stained red/pink. The viability test was further confirmed by the glyphosate selection titer experiments.

In these experiments, it was determined that 93% of the 312 total B73 iVAEs survived the drying protocol. In another experiment with LH244 iVAEs of a similar physiological age that were both dried and then stored at −20° C., 95% survival of 360 iVAEs survived the storage process.

Post Storage Rehydration Method of the iVAE embryos: Dried maize embryos (iVAEs) were placed on a sterile plate of Regeneration Medium II) and incubated at room temperature for 1 hour. Afterward, sterile water was added and embryos were incubated at room temperature for an additional hour followed by gentile agitation to complete the rehydration process. Embryos were then placed on experimental media to determine survival as well as sensitivity to glyphosate. The rehydrated maize iVAEs were placed on media plates, evenly spaced, and each plate was sealed with porous tissue culture tape and incubated in growth chamber at 26° C. with 16/8 light/dark photoperiod with 60 µmol m-2 s-1. For up to 56 days of observation.

TABLE 4

Regeneration Medium II

| | 1L |
|---|---|
| MS Salts | 4.3 g |
| Sucrose | 30 g |
| Cleary's fungicide 50WP | 60.0 mg |
| pH to 5.8 with KOH | |
| Gelrite or phytagel | 3 g |
| Autoclave for 35 min | |
| Add after autoclaving: | |
| Thiamine HCL (1 mg/ml) | 100 µL |
| Pyridoxine HCL (1 mg/ml) | 500 µL |
| Nicotinic Acid (1 mg/ml) | 500 µL |
| Glycine (1 mg/ml) | 2 mL |
| Myo-inositol (1 mg/ml) | 100 µL |
| Cefotaxime (100 mg/ml) | 2 mL |

Example 10

20 DAP LH244 ears were collected from self-pollinated plants in the greenhouse. The embryos were extracted using the iVAE protocol. The extracted and cleaned embryos were placed in a drying chamber with MgNO3 saturated salts for 4 days. LH244 embryos were frozen for 4 days, or until used, at −20° C. in a hermetically closed 50 mL Falcon tube LH244 embryos were rehydrated as described in Example 9. Following rehydration, plates were set up using Regeneration II Medium. The first replicate has 30 embryos per plate, and the second only 22 per plate. The measurements are standardized to the number of surviving embryos, as measured by the number of embryos displaying coleoptile elongation. A subset of embryos was tested for viability using tetrazolium chloride (TTC).

We analyzed this experiment by counting the percent germination, looking at stress phenotype and using the viability stain tetrazolium chloride (TTC). In general, during germination, green tissue is healthy, purple tissue is stressed and producing anthocyanins, and silver or white tissue is not producing chlorophyll.

Mechanically extracted, dried and frozen iVAEs produced from 20 DAP (days after pollination) maize embryos were observed having a high average germination rate, of 93.3 and 95.9% for unfrozen and frozen embryos, respectively. iVAEs growing in the complete absence of selection agents grew vigorously and uniformly.

Tissue response to varying glyphosate concentrations: There was a reduction in embryos with green shoots and an increase in embryos with chlorotic shoots as the glyphosate concentration increased. 10 days after the start of the experiment, there was already a reduction in frequency of greening shoots on embryos plated on glyphosate with about 80% impairment on 50 µM glyphosate treatment plates. A similar effect could be achieved on 10 µM glyphosate treatment plates at 20 days, and it becomes much more obvious over time with 90% damage on 10 µM glyphosate treatment plates at 27 days.

In response to glyphosate, significant anthocyanin production was observed in treated embryos. An apparent reduction of anthocyanins synthesis occurred on higher glyphosate concentration, equal and more than 100 µM glyphosate. The anthocyanins are synthesized via a stress signals and come from a degradation of phenylalanine. It has been reported that there was a correlation between anthocyanin, phenolic compounds synthesis and PAL activity in maize seedlings (Duke and Naylor, 1974; Zaprometov and Shipilova, 1972; Duke and Hoagland, 1978; Hoagland, 1980). Duke and Hoagland (1978) reported that glyphosate, N-(phosphonomethyl)glycine induced phenyl-alanine ammonia-lyase (PAL) activity in the roots of dark-grown maize seedlings linked with loss of fresh weight, so we can conclude that the anthocyanin is caused by a stress and only impaired by higher and equal glyphosate concentration of 100 µM after 49 days.

References: Duke S O, Naylor A W. Effects of light on phenylalanine ammonia-lyase activity in dark-grown *Zea mays* (L.) seedlings. Plant Sci Lett. 1974; 2:289-93. doi: 10.1016/0304-4211(74)90086-8; Duke S O, Hoagland R E. Effects of glyphosate on metabolism of phenolic compounds I. Induction of phenylalanine ammonia-lyase activity in dark-grown maize roots. Plant Sci Lett. 1978; 11:185-90; Hoagland R E. Effects of glyphosate on metabolism of phenolic compounds: VI. Effects of glyphosine and glyphosate metabolites on phenylalanine ammonia-lyase activity, growth, and protein, chlorophyll, and anthocyanin levels in soybean (Glycine max) seedlings. Weed Sci. 1980; 28:393-400; and Zaprometov M N, Shipilova S V. Phenylalanine-ammonia lyase and synthesis of phenol compounds in maize seedlings. Sov Plant Physiol. 1972.

Example 11

Barley Mature Embryo Transformation

*Agrobacterium*-mediated transformation of monocots has generally relied on the immature embryo system where scutellar tissue of immature embryos is transformed; de-differentiated into embryogenic callus tissue using medium with relatively high auxin to cytokinin ratio; then regenerating embryos and transformed plants from this callus.(1) This system had been highly successful in monocot transformation but is severely genotype dependent in terms of germplasms capable of forming embryogenic callus (ex. Golden Promise barley). This system is also labor intensive and inefficient in terms of timing between inoculation and plants to soil.

Our strategy for transforming Barley mature monocot embryos avoids the use of callus generation and should therefore be less genotype dependent, is more rapid, and more amendable to automation. Our Barley mature monocot embryo transformation strategy involves the following steps: (i) Isolate storable mature embryo explants of Barley; (ii) Transform meristematic "leaf base" tissue; (iii) Induce multiple buds from these regions in presence of selection (with possibly a delay step); and (iv) Regenerate shoots and T0 plants from transgenic buds in presence of selection.

Transformation of leaf base tissue generally involves the use of force treatments either before or during inoculation. Use of force in terms of transfection improvement has been shown in the monocot immature embryo system and in banana.(2) Multiple bud formation generally involves using medium with a relatively high cytokinin to auxin ratio, as demonstrated by regeneration studies performed by Zhong. (3) We have used G418 selection with internal WCIC binaries as well as hygromycin selection using pANIC binaries.(4) This method does not rely on the expression of added morphogenic genes such as bbm and wus. (5)

Isolating Storable Mature Embryo Explants of Barley

Figure 14:
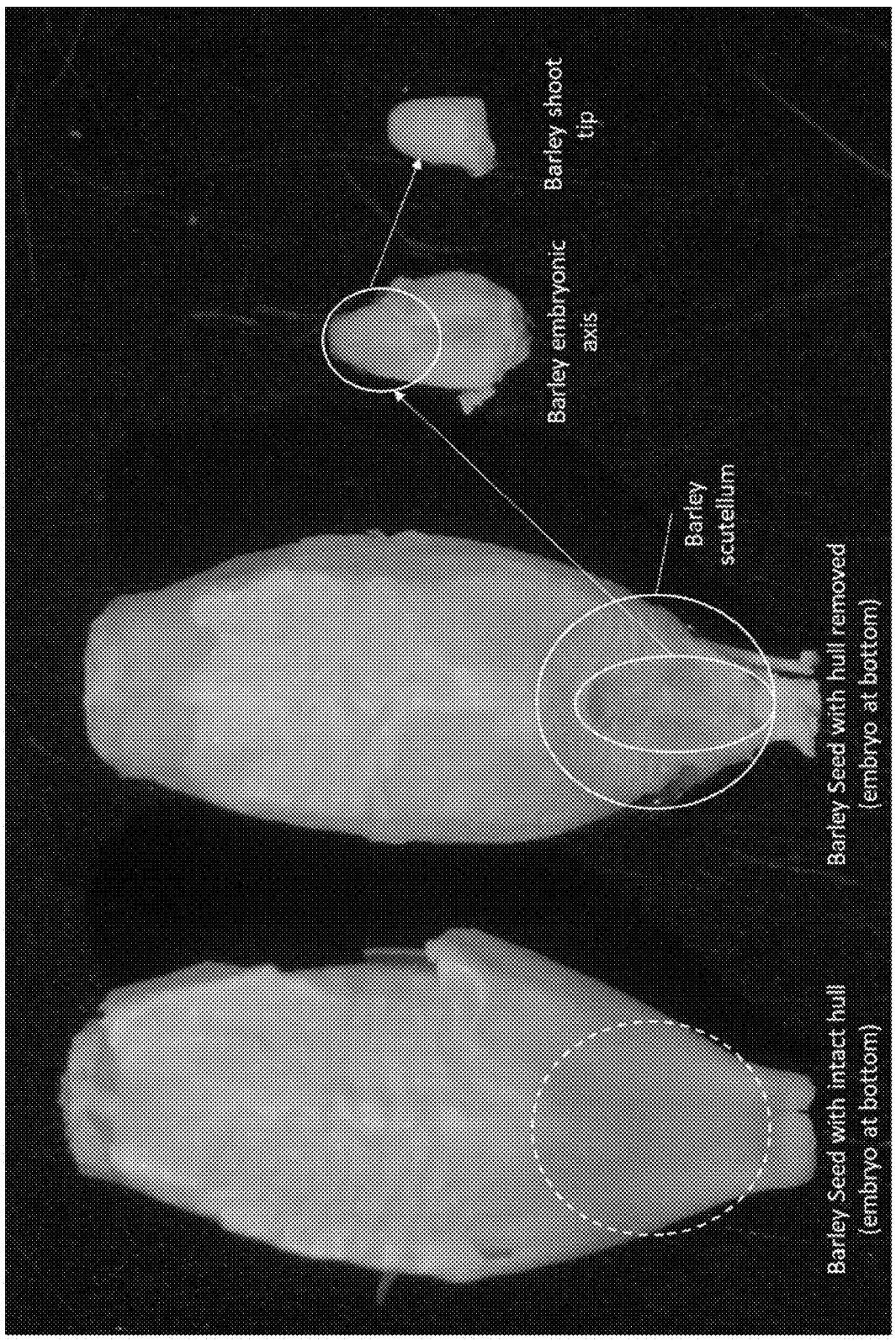
FIG. 14 shows barley seed and mature embryo explant anatomy (Gemcraft variety shown).

Barley mature embryos can be prepared by a variety of methods, by machine or by hand, and primed at different states. We have focused mainly on barley seed that has been surface sanitized in 20% Clorox for 5 minutes, then dried in laminar flow hood or Bryair seed drier for various lengths of time to vary internal moisture content. We focused on non-imbibed Barley seed as their appeared to be an inverse relation between leaf base transfection by *Agrobacterium* and seed imbibition time (described in next section) and to store explants at this relatively low moisture for 1-2 weeks before inoculation. FIG. 14 gives Barley seed and explant anatomy; the scutellum tissue is dissected away from the embryonic axis, and for shoot tips the radical portion of the embryonic axis is removed.

Figure 15:
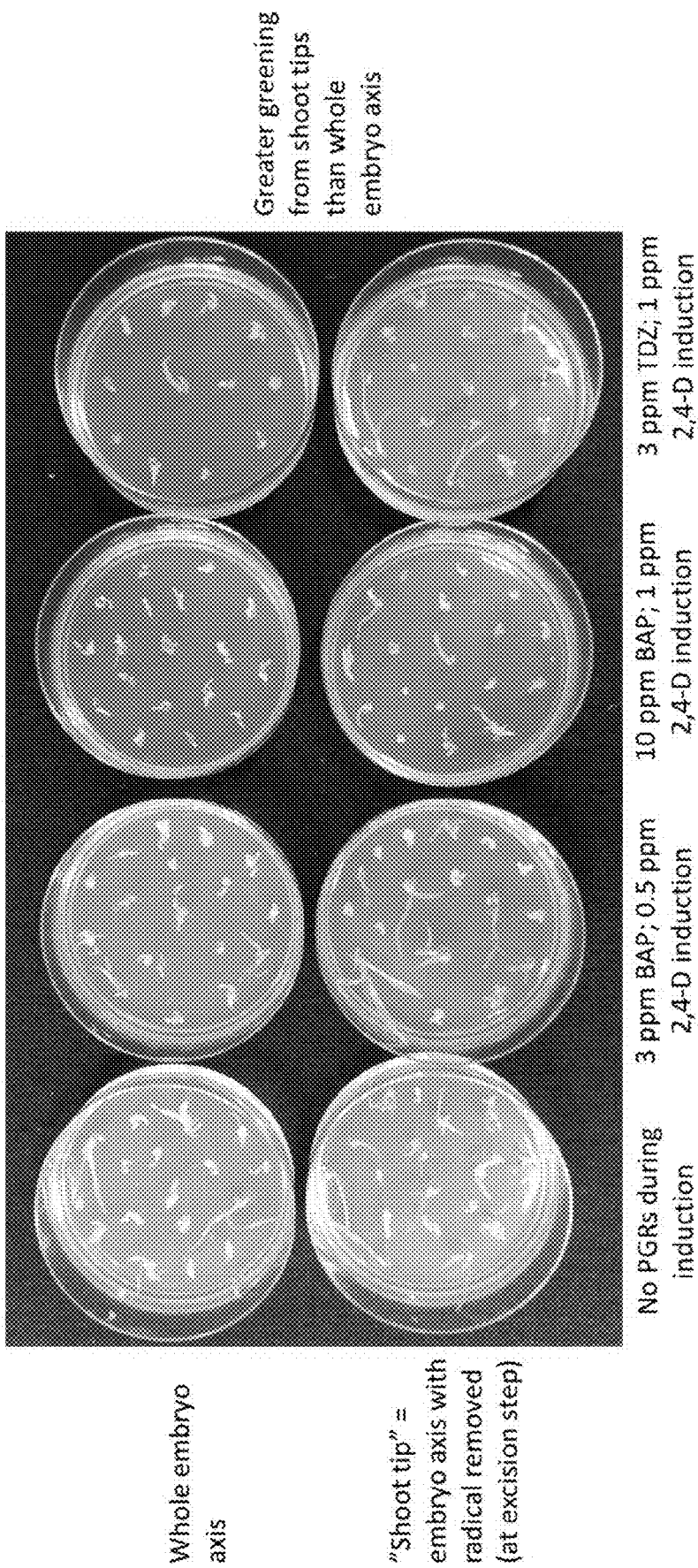
FIG. 15 shows barley whole embryo axis versus shoot tip health after co-culture and after 2 weeks on delay media with and without PGRs.
Figure 17A:
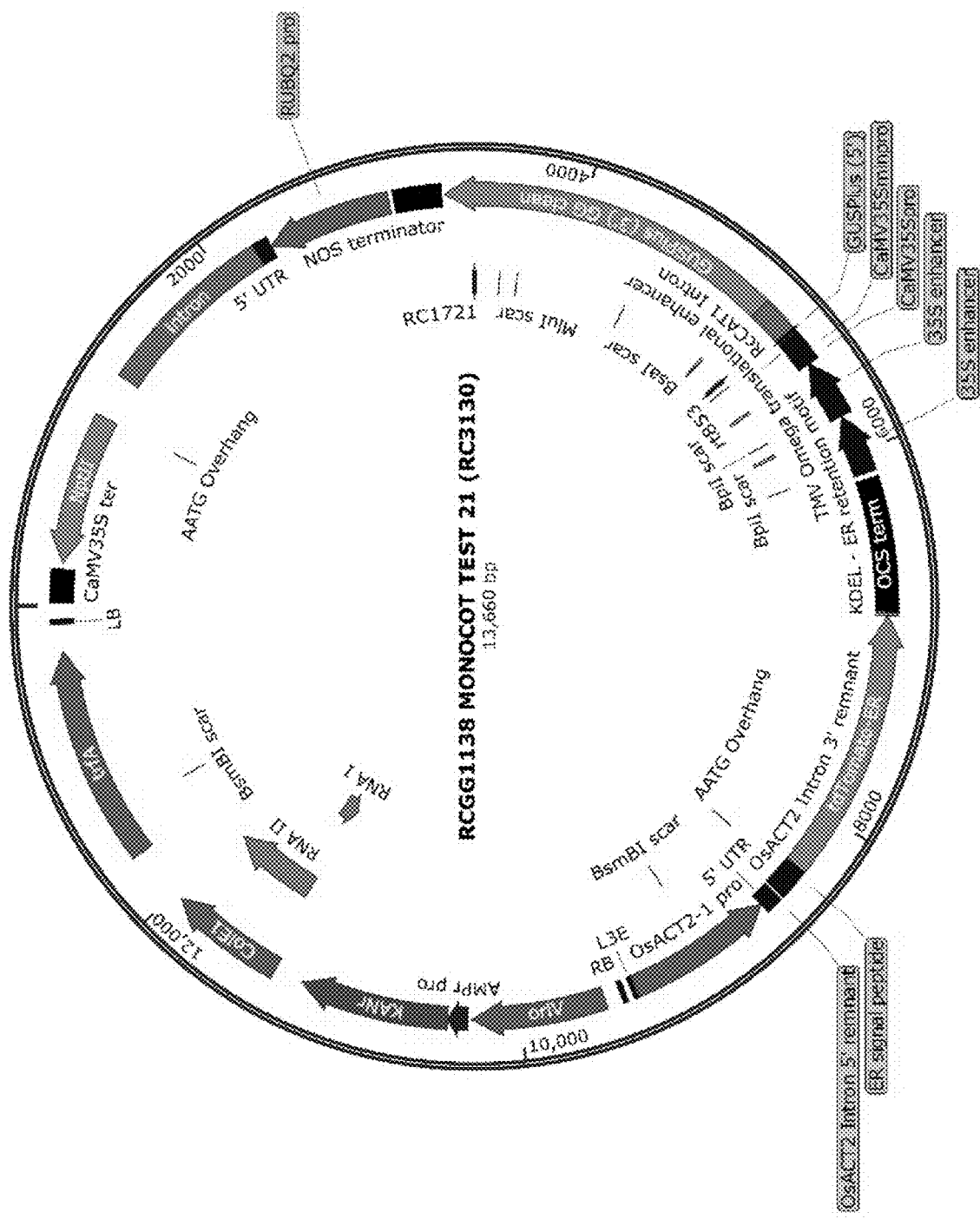
FIG. 17A shows a plasmid map for Monocot Binary 21.
Figure 17B:
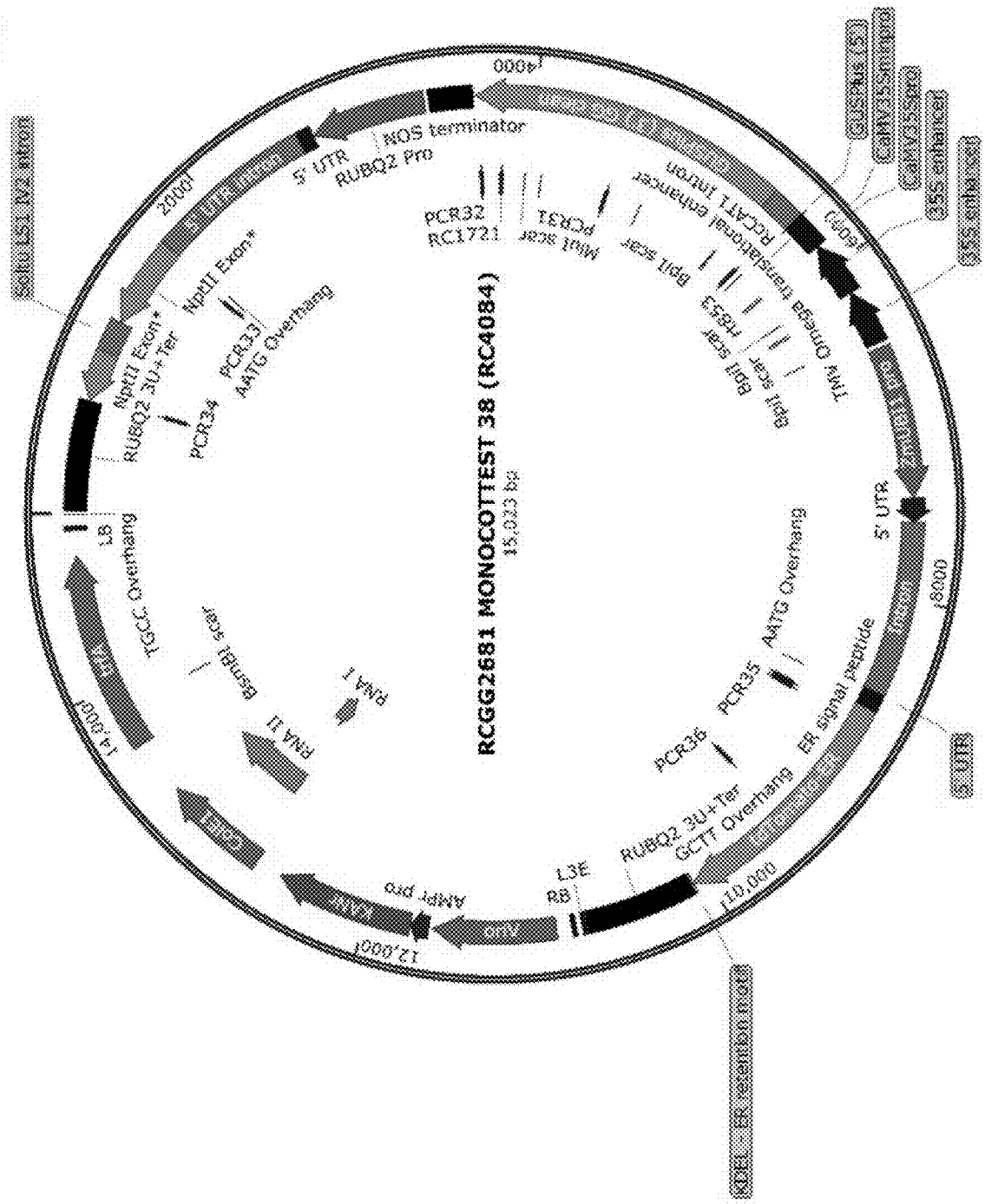
FIG. 17B shows a plasmid map for Monocot Binary 38.
Figure 18A:
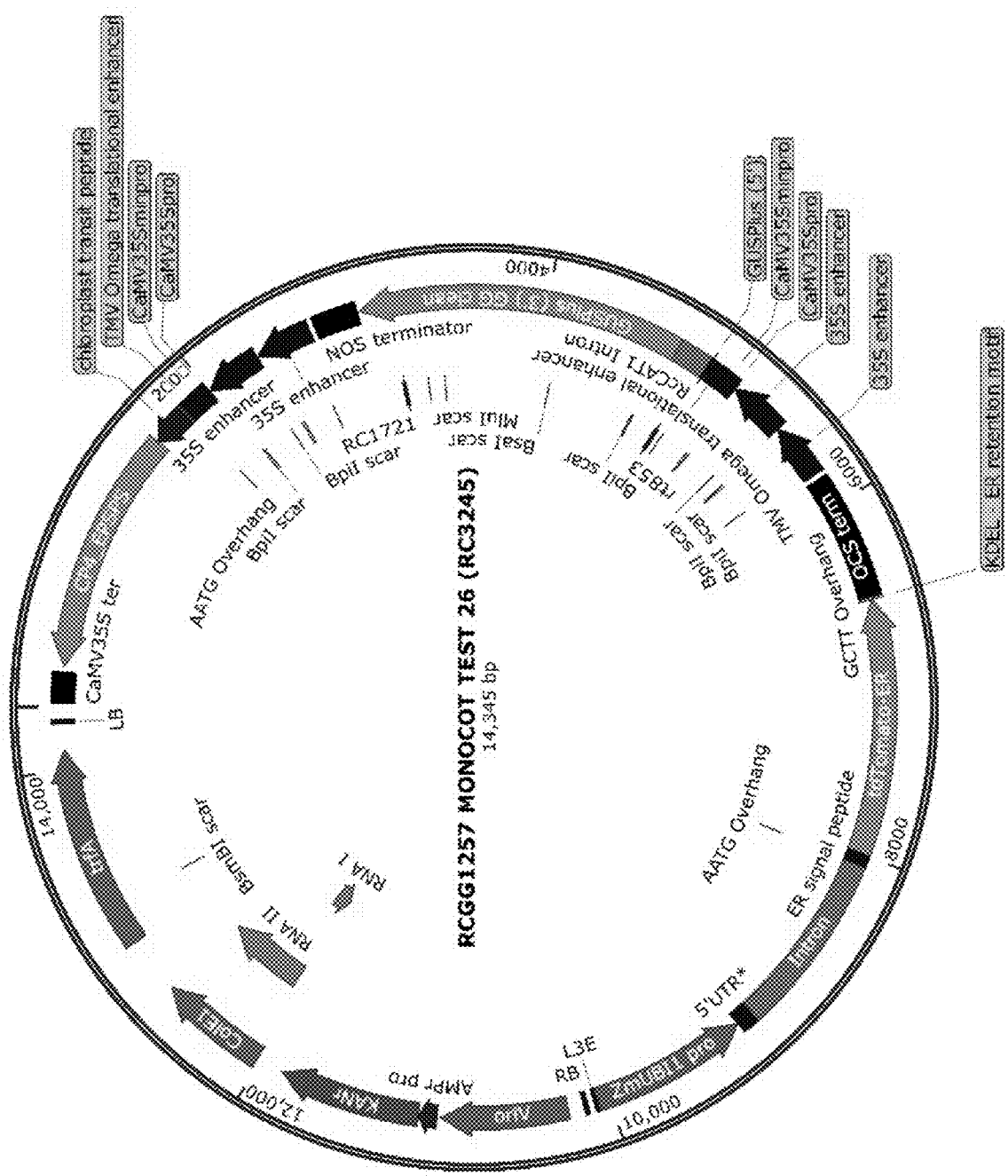
FIG. 18A shows a plasmid map for Monocot Binary 26.
Figure 18B:
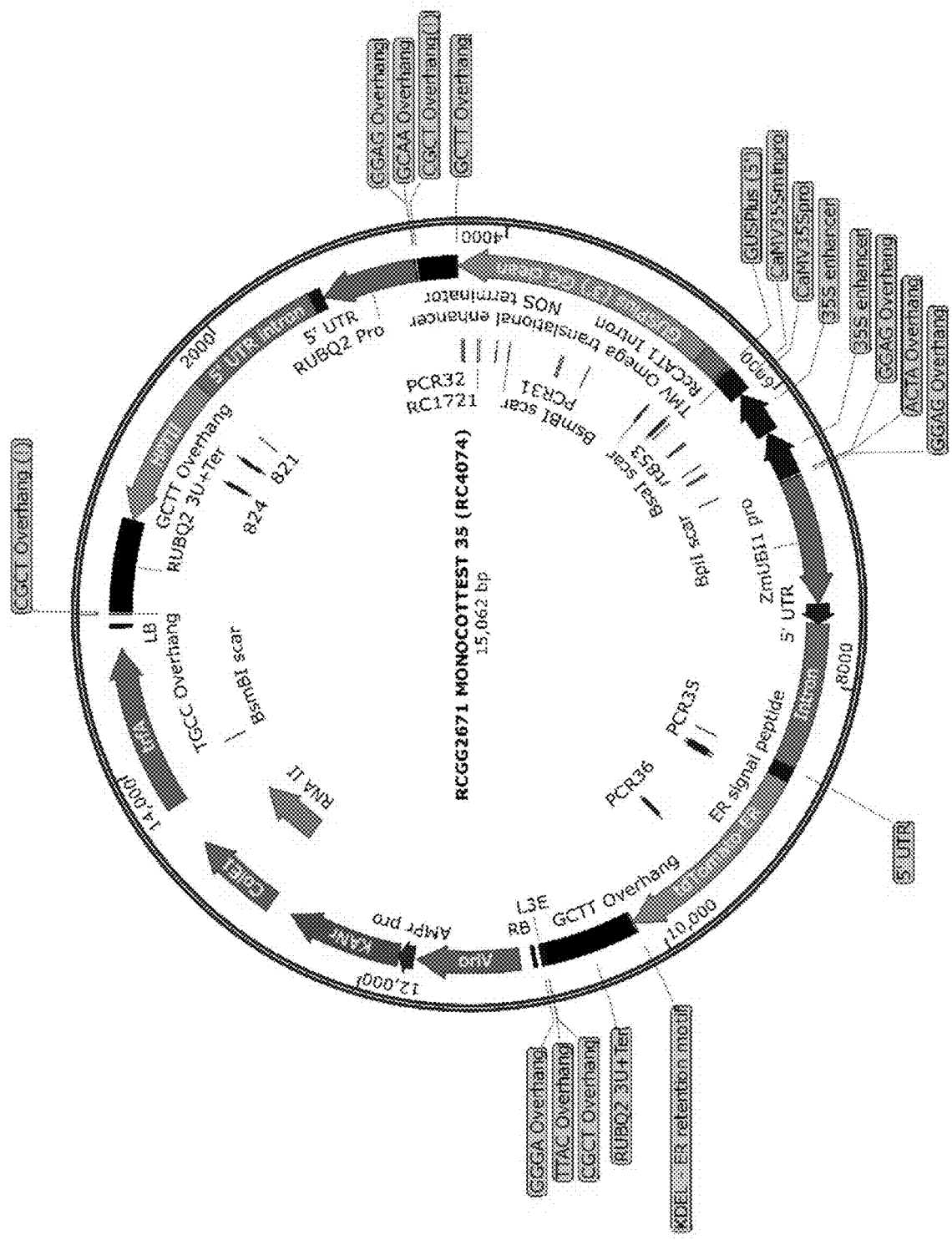
FIG. 18B shows a plasmid map for Monocot Binary 35.

Shoot tips appeared overall healthier than intact embryonic axis (FIG. 15, data summarized below); possibly due to increased nutrient uptake and/or decreased necrotic tissue with radical removal. It is also possible that the wounded surface along the shoot tip may provide attachment/access for *Agrobacterium* cells.

TABLE 5

Whole axis and shoot tip regeneration metrics

| Barley explant | 4 g/L agarose I induction; 4 g/L regeneration | 8 g/L agarose I induction; 4 g/L regeneration | 8 g/L agarose I induction; 4 g/L regeneration (30 mg/L G418 selection) |
|---|---|---|---|
| Whole axis | 21% | 8% | 17% |
| Shoot tip | x | 93% | 45% |

We also noticed a relationship between shoot tip health and initial internal moisture content, with explants derived from relatively higher moisture seed (~12-13% versus 8-10%) appearing healthier and having better regeneration after 2 weeks on delay media without PGRs (FIG. 16), so we have focused efforts on explants derived from Barley seed at 12-13% moisture. This effect may be an artifact of damage incurred during excision of seed, as we have noted seed rapidly becomes more brittle at lower moistures, and explants become more likely to shatter. Some variability in embryo extraction may be due to the genotype or seed lot used, although results are general expected to be reproducible across seed lots and genotypes.

Prior to inoculation, Barley mature embryo explants were surface sanitized using 20% PEG4000 in 70% ethanol (20 g PEG4000 dissolved in 100 ml 70% ethanol, filter sterilized) for 1 minute, then rinsed with ~500 ml sterile distilled water. Explants were then rehydrated in INO+60 mg/L Cleary's 3336 for 1 hour at room temperature. After which explants were inoculated with *Agrobacterium*.

Barley Meristematic "Leaf Base" Transformation with *Agrobacterium*

*Agrobacterium* inoculum was prepared under laminar flow hood from overnight cultures derived from 20% glycerol stocks stored at −80° C. Glycerol stocks were allowed to thaw, and stock was added to 50 ml LB with appropriate antibiotics to maintain binary/binary+helper plasmid (50 ppm kanamycin and 100 ppm gentamycin for AGL1+H strain; 50 ppm kanamycin for GV3101 and AGL1). The AGL1+H strain contains the pPHP71539 "helper" ternary plasmid that contains additional copies of the vir genes, and confers resistance to gentamycin to *Agrobacterium*.(6) Cultures were grown overnight at 28 C 200 RPM on orbital shaker (Innova 4400 incubator shaker). The next morning optical densities of cultures at 660 nm (OD660) were checked (Hach DR5000™ Spectrophotometer) under laminar flow and then centrifuged at 2619×g for 20 min (H6000A rotor on Sorvall® RC3B centrifuge). Pelleted bacteria was resuspended in WCIC INO media under laminar flow, diluted to OD660 0.3-0.6, and incubated at room temperature 150 RPM until used (VWR orbital shaker). Acetosyringone was added to inoculum at 100 uM to help induce virulence. We have obtained transgenic T0 Barley plants from the Gemcraft variety on G418 selection using AGL1+H harboring Monocot Binary 21; as well as from AGL1+H/Monocot Binary 38.

In pilot tests for transient transfection studies, GV3101 harboring VS224 or AGL1+H harboring Monocot Binary 26 were used. For pilot regeneration studies using hygromycin selection, AGL1/pANIC 6A was used. For follow-up tests using hygromycin selection, AGL1+H/Monocot Binary 35 was used.

Figure 19:
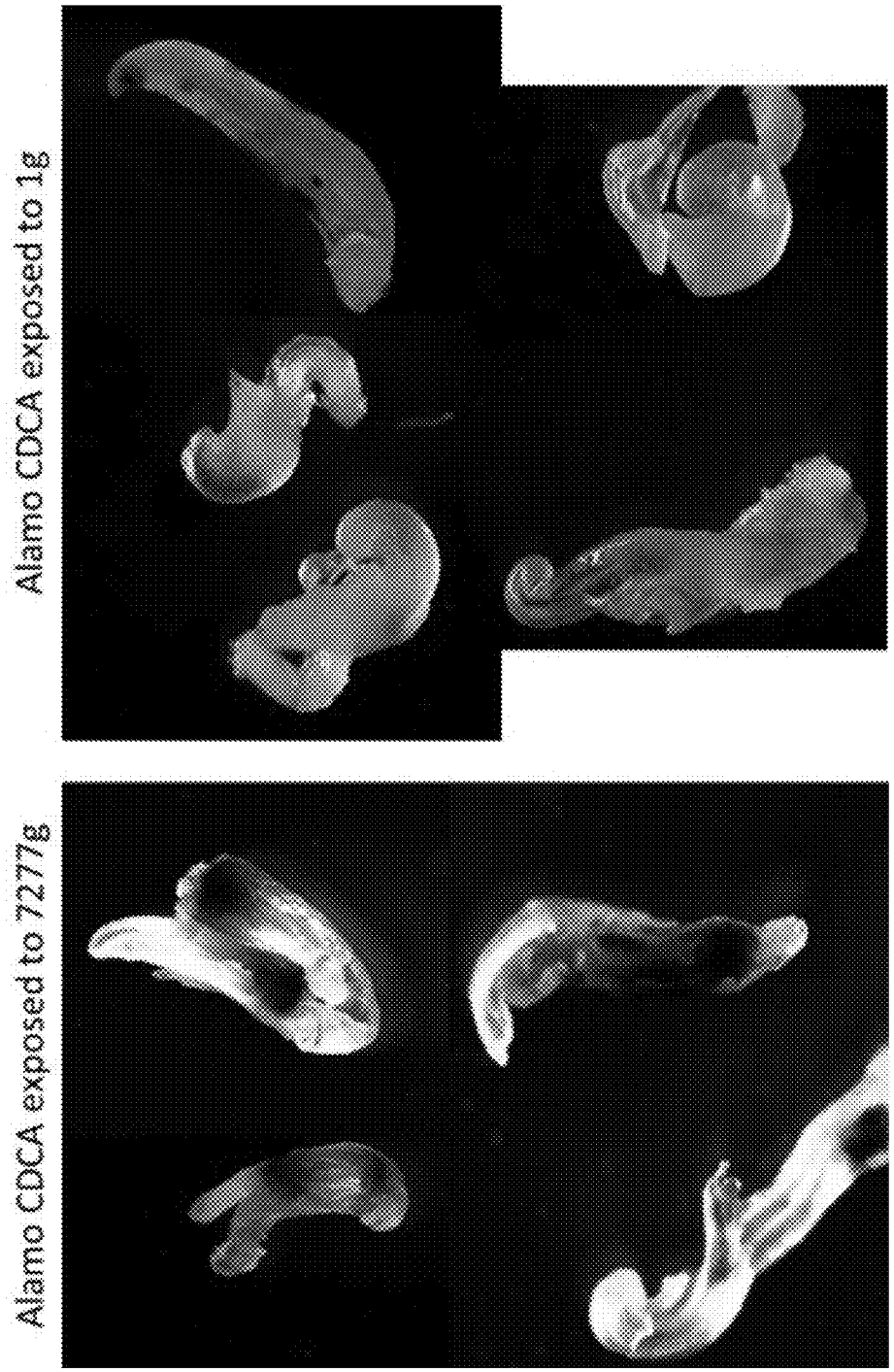
FIG. 19 shows transient GUS expression in Barley Mature Embryo explants (Alamo CDCA variety) exposed to 7277 g or 1 g during inoculation.

We initially noted an increase in Barley mature embryo explant infection with *Agrobacterium* when force was applied prior to or during the inoculation phase. We have been primarily applying force through centrifugation, and primarily at 7277 g on the Sorvall H6000A rotor (which corresponds to 5000 rpm on this rotor) with 50 ml of either INO media or *Agrobacterium* inoculum resuspended in INO. (FIG. 19) These conditions are approximately equal to ~3570 N of force, if we model uniform force field during centrifugation (it actually varies along the length of the tube), and the entire mass is at bottom of tube:

$$F=ma$$

$$F=(0.05 \text{ kg})(7277)(9.8 \text{ m/s}^2)=3570 \text{ N}$$

Figure 20:
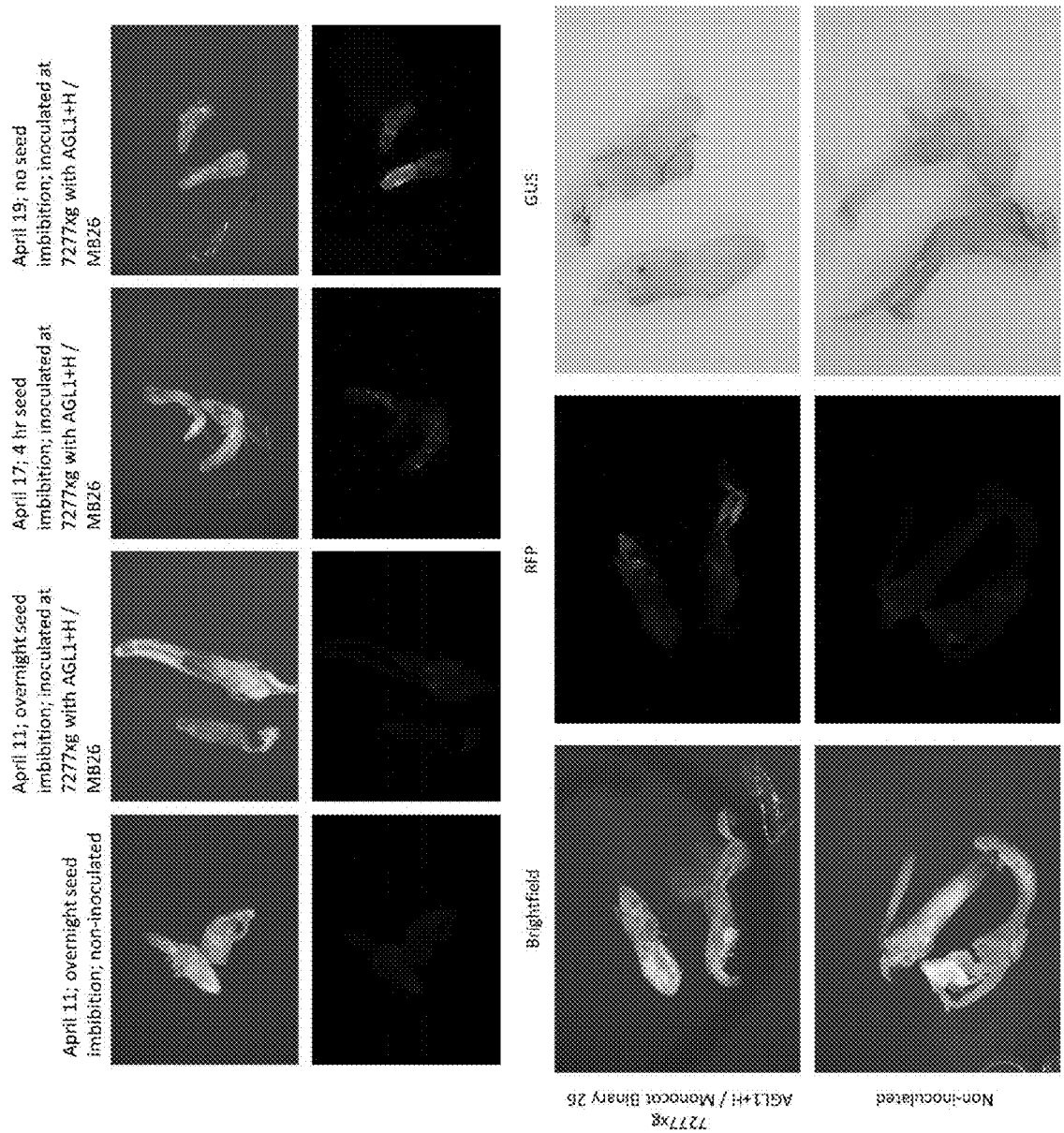
FIG. 20 shows transient RFP and GUS expression in Barley mature embryo explants (Gemcraft variety) derived from seed imbibed for varying times.
Figure 24:
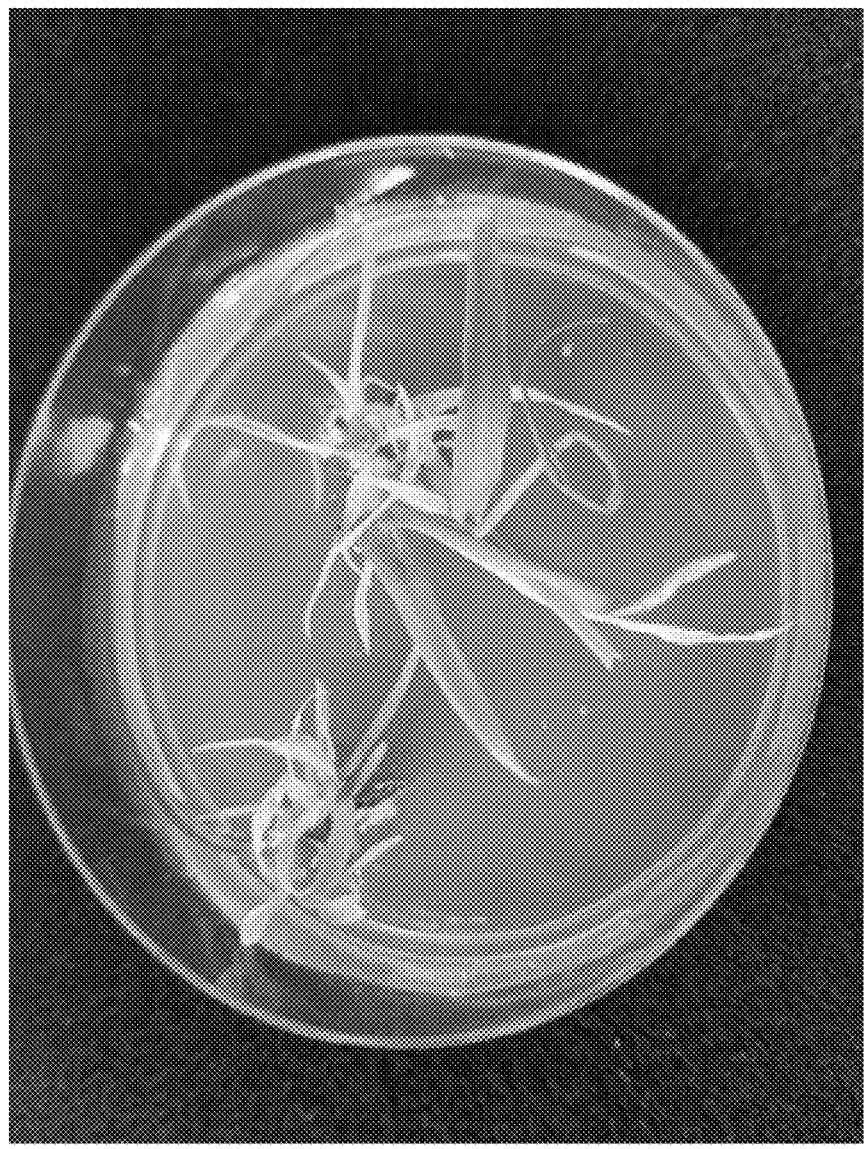
FIG. 24 shows T0 barley events WP412-1 and WP412-2 rooting on 30 mg/L G418.
Figure 25:
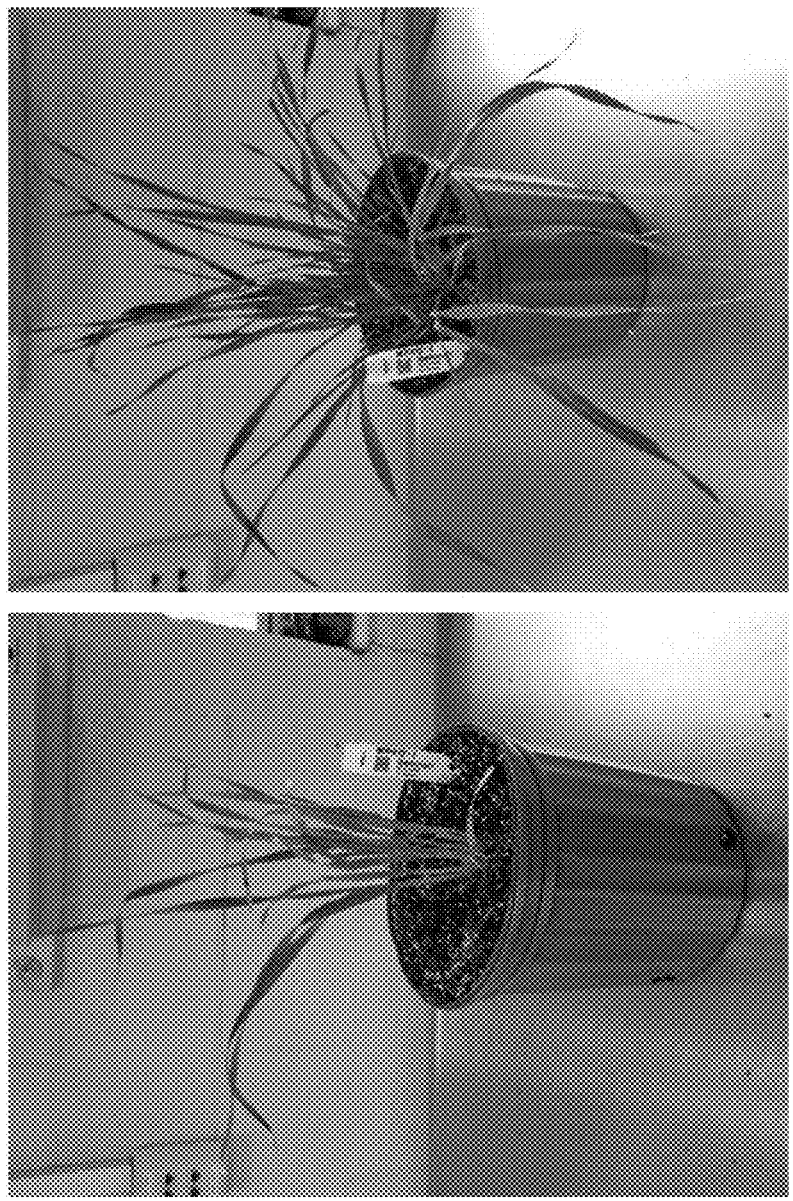
FIG. 25 shows T0 barley events WP412-1 and WP412-2 after 4 weeks in greenhouse.

As shown in FIG. 20, a general decrease in transient transfection, as measured by RFP and GUS expression, was seen of Gemcraft Barley explants exposed to 7277×g when seed were germinated overnight or for 4 hours. (FIG. 20).

After the centrifugation phase, explants are allowed to rest for approximately 30 minutes at room temperature. Explants are then co-cultured on one piece of filter paper in a Plantcon container with 2 ml INO+100 uM acetosyringone+60 mg/L Cleary's 3336 fungicide+50 mg/L nystatin+10 mg/L thiabendazole (TBZ). Explants were co-cultured for 4 days at 23 C 16/8 photoperiod.

Multiple Bud/Shoot Induction from Leaf Base of Barley

To induce multiple buds/shoots from the leaf base of Barley shoot tips post co-culture, we applied medium with a high relative amount of cytokinin to auxin (measured by either concentration or relative activity). Explants were generally on these bud induction medium for a total of 2 weeks, after which presence of multiple buds/shoots was assessed (phenotype shown in FIG. 21, with data summarized in boxplot form in FIG. 22). We found a relatively high amount of either TDZ or BAP to 2,4-D could induce multiple buds/shoots in barley shoot tips. Budding medium 2G and 2J used 3 mg/L BAP and 0.5 mg/L 2,4-D, which were found to induce multiple shooting in Barley mature embryos of the HOR7231 variety.(7) Budding medium 2I and 2L used 3 mg/L TDZ and 1 mg/L 2,4-D, which were based on results of multiple shoot induction in shoot segments derived from Barley mature explants of multiple varieties using 3 mg/L TDZ and 2 mg/L picloram.(8) The induction media was either MS or B5 based, and used either agarose 1 or phytagel as gelling agent. In some experiments, after 1 week on induction media without selection, explants were transferred to induction media with selection. During this 2-week period explants were kept at 27 C 16/8 photoperiod. It may be possible to reduce chimerism in T0 Barley plants by extending this shoot multiplication step to 4-8 weeks.(9)

TABLE 6

Monocot Basal Budding Media 2

| Ingredients and Notes | Amount to add per liter (grams) |
|---|---|
| MS Salts with Gamborg B5 Vitamins (Phytotech M404) | 4.44 |
| Maltose | 30 |
| L-Proline (Caisson Labs CAS 147-85-3) | 1 |
| Casein hydrolysate | 1 |
| Cupric Sulfate (CuSO4) (1 mg/ml) | 0.160 ml |
| MES | 2 |
| Cleary's | 0.06 |
| pH to 5.8 with 1N KOH | |
| Gelling agent | as specified |
| autoclave | |
| Add the following post-autoclave: | |
| Carbenicillin (100 mg/ml stock) | Use at 2 ml per Liter (200 mg/L) |
| Cefotaximine (100 mg/ml stock) | Use at 2 ml per Liter (200 mg/L) |
| Timetin (150 mg/ml stock) | Use at 1 ml per Liter (150 mg/L) |
| PGRs | as specified |
| Selection | as specified |

| Media G-I | Media J-M |
|---|---|
| 4 g/L Agarose I | 8 g/L Agarose I |

| Media G, J | Media H, K |
|---|---|
| 3 mg/L BAP + 0.5 mg/L 2,4-D | 10 mg/L BAP + 1 mg/L 2,4-D |

| Media I, L | Media M |
|---|---|
| 3 mg/L TDZ + 1 mg/L 2,4-D | 10 mg/L TDZ + 0.5 mg/L 2,4-D |
| Container Distribution | Deep plates 50 ml/plate |

In budding and regeneration medium 3 and 4, we increased the cupric sulfate concentration to 1.25 mg/L based on optimized results found in the Barley immature embryo transformation system with the Golden Promise variety.(10) Budding and regeneration medium 3 and 4 also replace agarose I as a gelling agent with phytagel. We tested B5 salts in budding and regeneration medium 4 alongside MS salts in budding and regeneration medium 3 as the presence of ammonium nitrate in MS salts might inhibit nitrate uptake in Barley mature embryo explants.(11)

TABLE 7

Monocot Basal Budding Media 3

| Ingredients and Notes | Amount to add per liter (grams) |
|---|---|
| MS Salts with Gamborg B5 Vitamins (Phytotech M404) | 4.44 |
| Maltose | 30 |
| L-Proline (Caisson Labs CAS 147-85-3) | 1 |
| Casein hydrolysate | 1 |

TABLE 7-continued

Monocot Basal Budding Media 3

| Cupric Sulfate (CuSO4) (1 mg/ml) | 1.25 ml |
|---|---|
| MES | 2 |
| Cleary's | 0.06 |
| pH to 5.8 with 1N KOH | |
| Phytagel | 3.50 |
| autoclave | |
| Add the following post-autoclave: | |
| Carbenicillin (100 mg/ml stock) | Use at 2 ml per Liter (200 mg/L) |
| Cefotaximine (100 mg/ml stock) | Use at 2 ml per Liter (200 mg/L) |
| Timetin (150 mg/ml stock) | Use at 1 ml per Liter (150 mg/L) |
| PGRs | see below |
| Selection | as specified |

| Media 3A | Media 3B |
|---|---|
| 2 mg/L BAP 0.5 mg/L 2,4-D | 5 mg/L BAP 0.5 mg/L 2,4-D |

| Media 3C | Media 3D |
|---|---|
| 10 mg/L BAP 0.5 mg/L 2,4-D | 2 mg/L BAP 1 mg/L 2,4-D |

| Media 3E | Media 3F |
|---|---|
| 5 mg/L BAP 1 mg/L 2,4-D | 10 mg/L BAP 1 mg/L 2,4-D |

| Media 3G | Media 3H |
|---|---|
| 2 mg/L trans-zeatin 0.5 mg/L 2,4-D | 5 mg/L trans-zeatin 0.5 mg/L 2,4-D |

| Media 3I | Media 3J |
|---|---|
| 10 mg/L trans-zeatin 0.5 mg/L 2,4-D | 2 mg/L trans-zeatin 1 mg/L 2,4-D |

| Media 3K | Media 3L |
|---|---|
| 5 mg/L trans-zeatin 1 mg/L 2,4-D | 10 mg/L trans-zeatin 1 mg/L 2,4-D |

| Media 3M | Media 3N |
|---|---|
| 2 mg/L TDZ 0.5 mg/L 2,4-D | 5 mg/L TDZ 0.5 mg/L 2,4-D |

| Media 3O | Media 3P |
|---|---|
| 10 mg/L TDZ 0.5 mg/L 2,4-D | 2 mg/L TDZ 1 mg/L 2,4-D |

| Media 3Q | Media 3R |
|---|---|
| 5 mg/L TDZ 1 mg/L 2,4-D | 10 mg/L TDZ 1 mg/L 2,4-D |
| Container Distribution | Deep plates 50 ml/plate |

TABLE 8

Monocot Basal Budding Media 4

| Ingredients and Notes | Amount to add per liter (grams) |
|---|---|
| Phytotechnology Laboratories B5 salts G398 | 3.21 |
| Maltose | 30 |
| L-Proline (Caisson Labs CAS 147-85-3) | 1 |
| Casein hydrolysate | 1 |

TABLE 8-continued

Monocot Basal Budding Media 4

| | |
|---|---|
| Cupric Sulfate (CuSO4) (1 mg/ml) | 1.25 ml |
| MES | 2 |
| Cleary's | 0.06 |
| pH to 5.8 with 1N KOH | |
| Phytagel | 3.50 |
| autoclave | |
| Add the following post-autoclave: | |
| Carbenicillin (100 mg/ml stock) | Use at 2 ml per Liter (200 mg/L) |
| Cefotaximine (100 mg/ml stock) | Use at 2 ml per Liter (200 mg/L) |
| Timetin (150 mg/ml stock) | Use at 1 ml per Liter (150 mg/L) |
| PGRs | see below |
| Selection | as specified |

| Media 4A | Media 4B |
|---|---|
| 2 mg/L BAP | 5 mg/L BAP |
| 0.5 mg/L 2,4-D | 0.5 mg/L 2,4-D |

| Media 4C | Media 4D |
|---|---|
| 10 mg/L BAP | 2 mg/L BAP |
| 0.5 mg/L 2,4-D | 1 mg/L 2,4-D |

| Media 4E | Media 4F |
|---|---|
| 5 mg/L BAP | 10 mg/L BAP |
| 1 mg/L 2,4-D | 1 mg/L 2,4-D |

| Media 4G | Media 4H |
|---|---|
| 2 mg/L trans-zeatin | 5 mg/L trans-zeatin |
| 0.5 mg/L 2,4-D | 0.5 mg/L 2,4-D |

| Media 4I | Media 4J |
|---|---|
| 10 mg/L trans-zeatin | 2 mg/L trans-zeatin |
| 0.5 mg/L 2,4-D | 1 mg/L 2,4-D |

| Media 4K | Media 4L |
|---|---|
| 5 mg/L trans-zeatin | 10 mg/L trans-zeatin |
| 1 mg/L 2,4-D | 1 mg/L 2,4-D |

| Media 4M | Media 4N |
|---|---|
| 2 mg/L TDZ | 5 mg/L TDZ |
| 0.5 mg/L 2,4-D | 0.5 mg/L 2,4-D |

| Media 4O | Media 4P |
|---|---|
| 10 mg/L TDZ | 2 mg/L TDZ |
| 0.5 mg/L 2,4-D | 1 mg/L 2,4-D |

| Media 4Q | Media 4R |
|---|---|
| 5 mg/L TDZ | 10 mg/L TDZ |
| 1 mg/L 2,4-D | 1 mg/L 2,4-D |
| Container | Deep plates |
| Distribution | 50 ml/plate |

T0 Plant Regeneration from Transgenic Buds in Presence of Selection

After the 2-week bud induction period, Barley explants were transferred to PGR-free regeneration media with selection and kept at 27 C 16/8 photoperiod. Explants are transferred every 3-4 weeks as needed to fresh regeneration media with selection to prevent *Agrobacterium* overgrowth. We obtained GUS expressing, PCR positive (tdTomato) T0 Barley plants of the Gemcraft variety from G418 selection using nptII, but obtained our first PCR+ shoot from hygromycin selection/hptII (shoot did not root) (FIG. 23).

The first two T0 plants we obtained was obtained from Gemcraft shoot tips inoculated with AGL1+H/Monocot Binary 21; with 2 week bud induction on media 2 L (MS based; 3 mg/L TDZ+1 mg/L 2,4-D; 8 g/L agarose I). The second week of bud induction explants were transferred to 2 L with 30 mg/L G418. At the end of the 2-week bud induction protocol, explants were transferred to Regeneration media 2 with 30 mg/L G418. Explants were subcultured to fresh media approximately 4 weeks later, and 3 weeks after this two shoots had rooted on G418 selection and were sent to greenhouse as WP412-1 and WP412-2. After 4 weeks in greenhouse, multiple leaf samples were taken from each plant for GUS expression and PCR analysis. Leaf DNA from was extracted using the REDExtract-N-Amp™ Plant PCR Kit (Sigma-Aldrich XNAP-1KT) following manufacturer's instructions. PCR reaction was run with the following protocol and products were run on 1.5% agarose gel in SB buffer.

Figure 26:
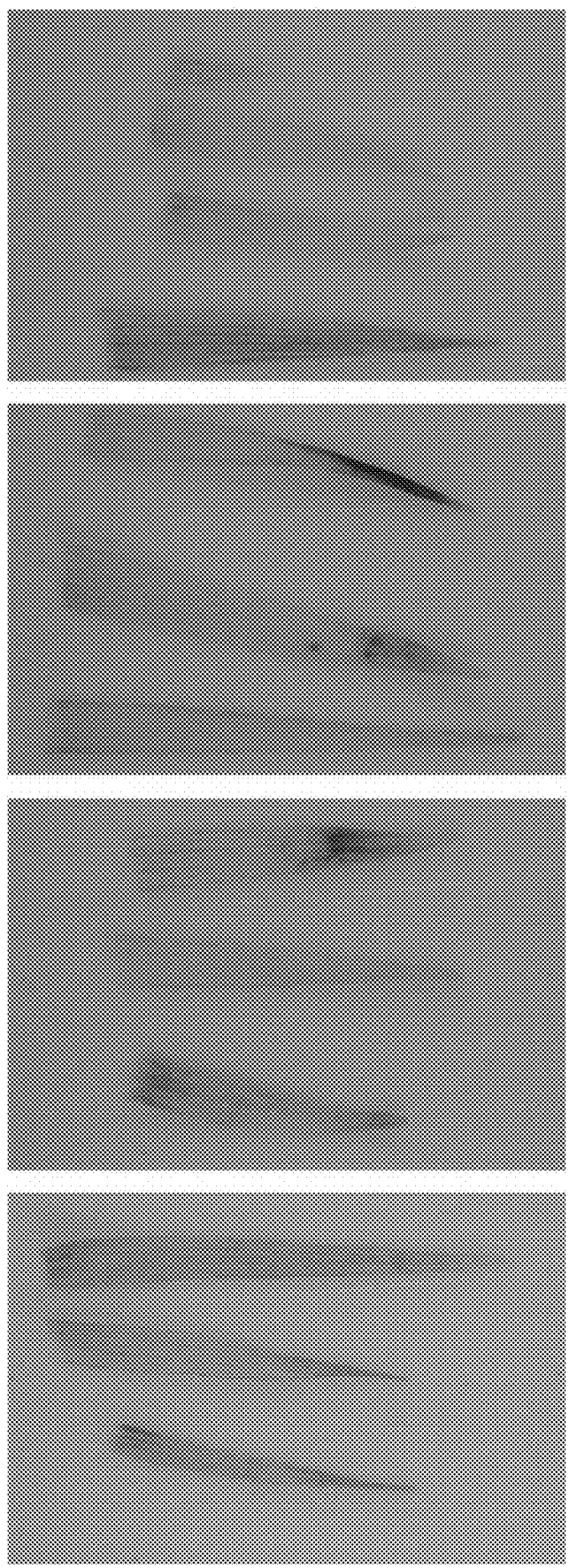
FIG. 26 shows stable GUS expression in leaves of T0 barley event WP412-1.
Figure 27:
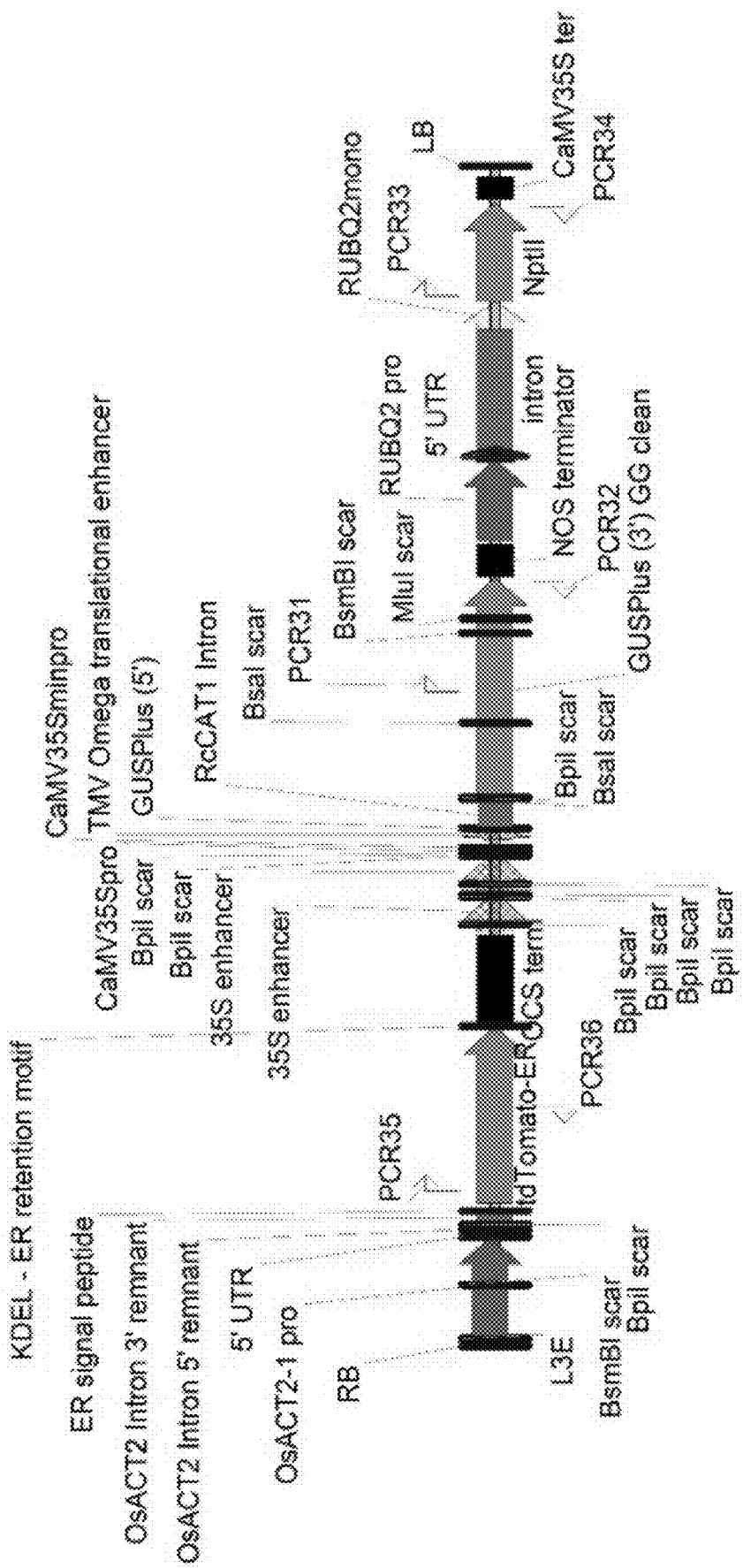
FIG. 27 shows PCR35 and PCR36 primer location on Monocot Binary 21.
Figure 28:
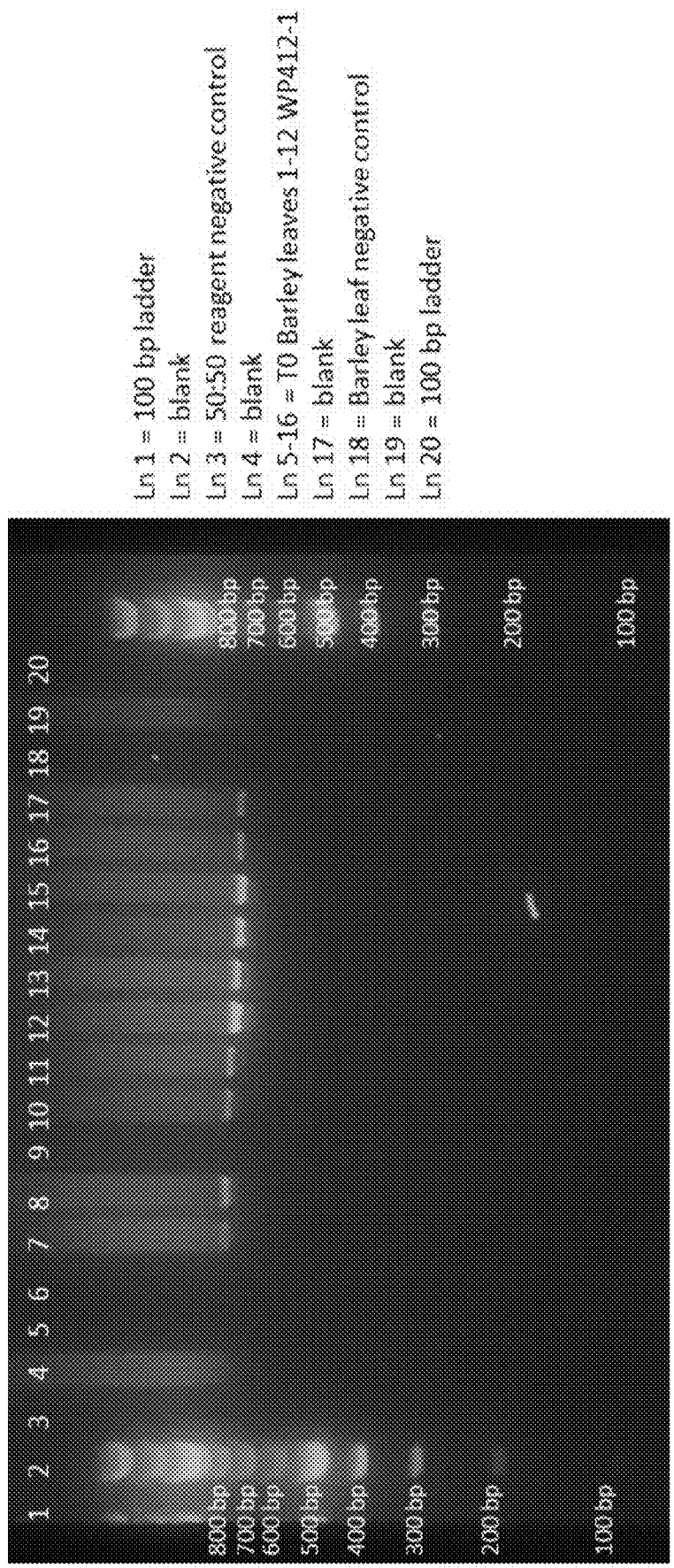
FIG. 28 shows PCR amplification of tdTomato gene in barley T0 event WP412-1.
Figure 29:
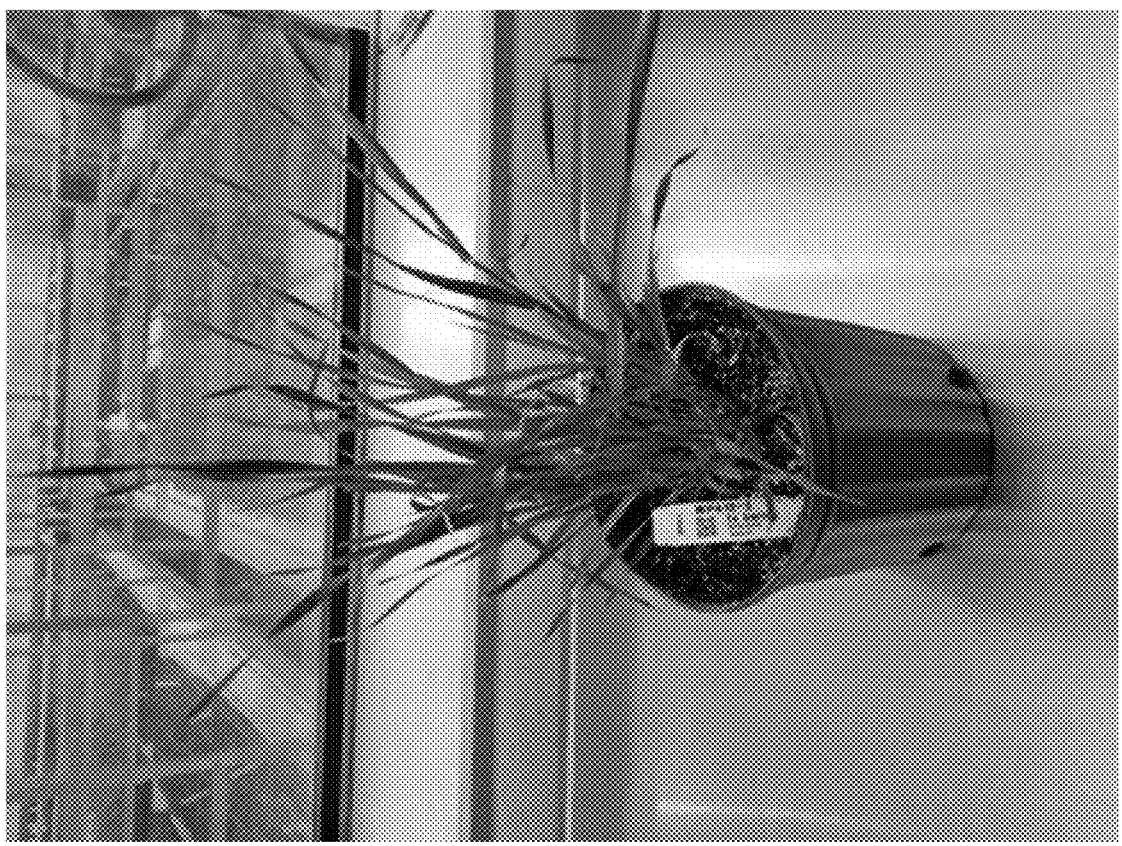
FIG. 29 shows T0 barley event WP412-3 after 4 weeks in greenhouse.
Figure 30:
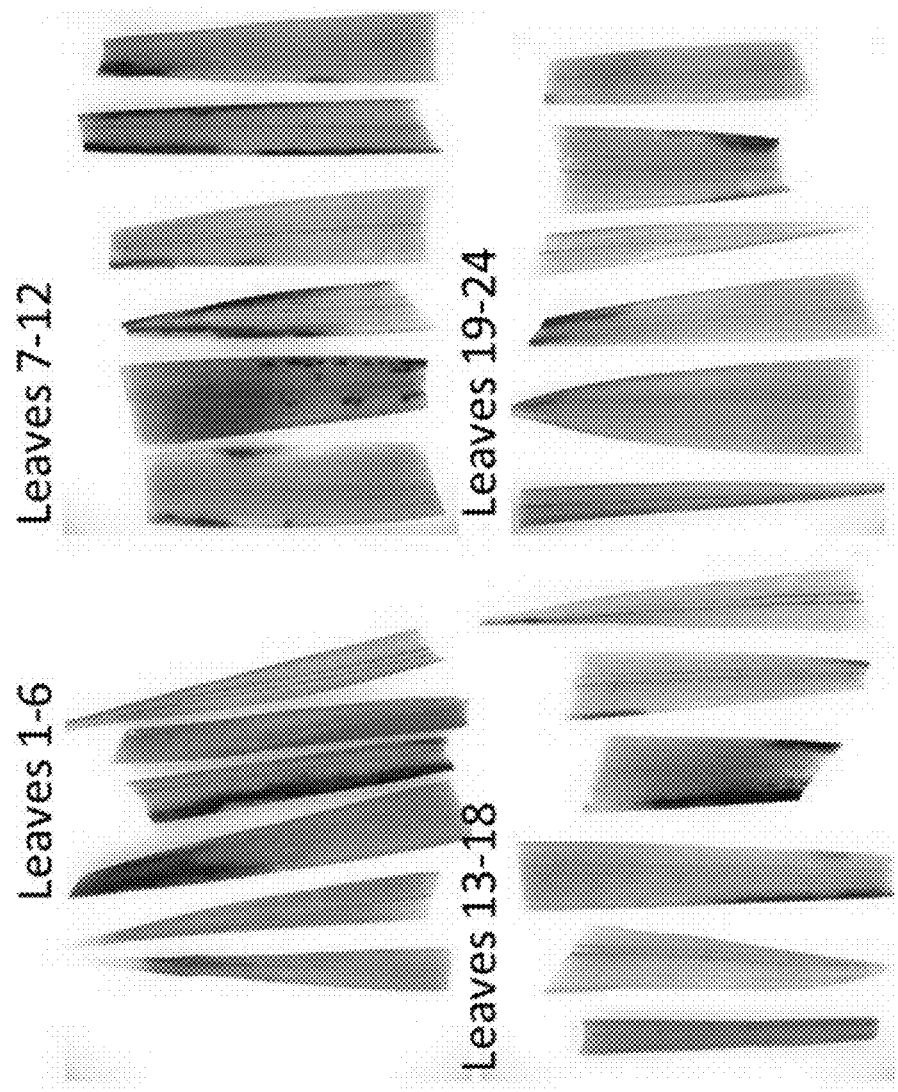
FIG. 30 shows stable GUS expression in leaves of T0 barley event WP412-3.
Figure 31:
FIG. 31 shows PCR amplification of tdTomato gene in barley T0 event WP412-3.
Figure 32:
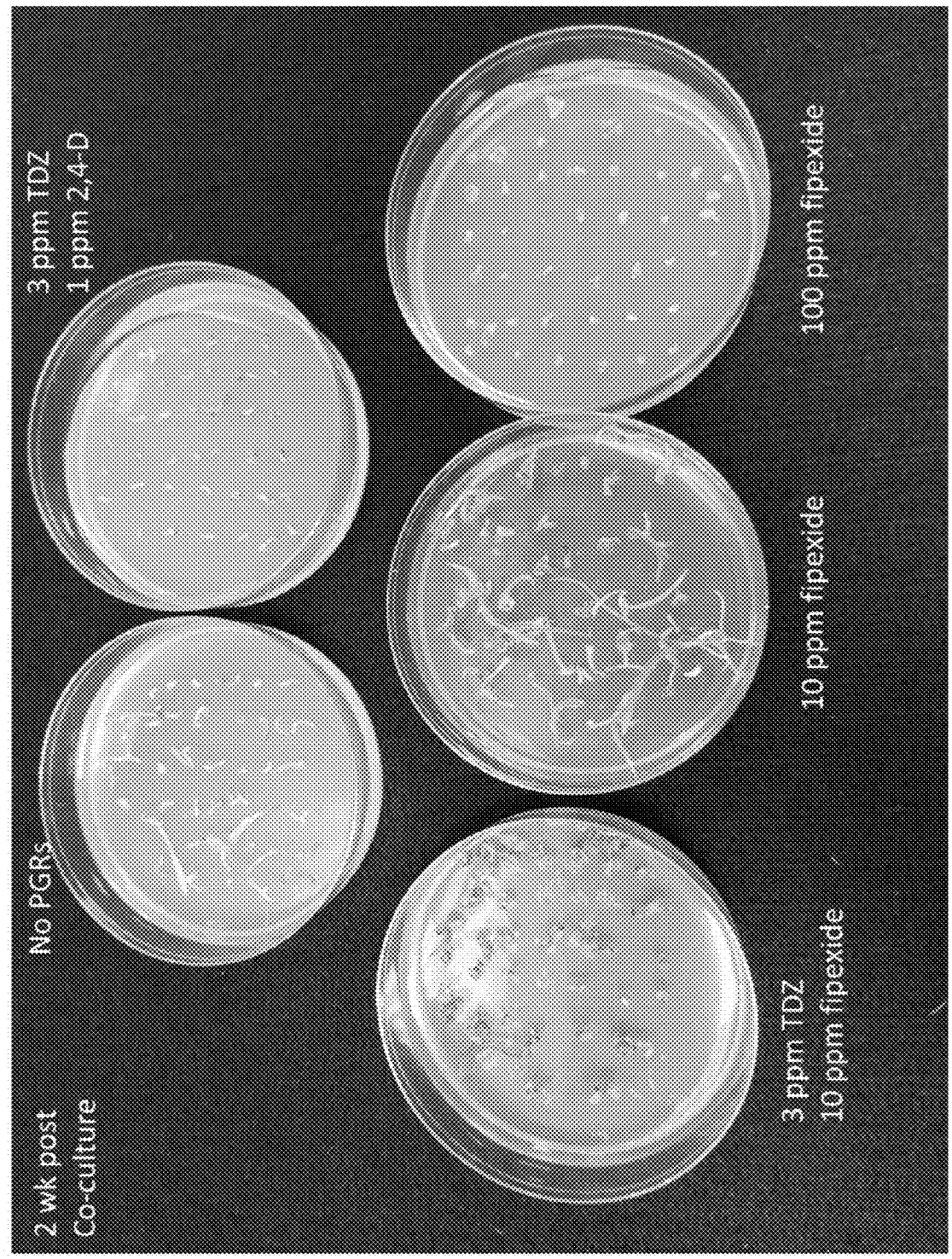
FIG. 32 shows barley explant phenotype after 2 weeks on bud induction medium replacing 2,4-D with fipexide; and with removal of TDZ and removal of PGRs.
Figure 33:
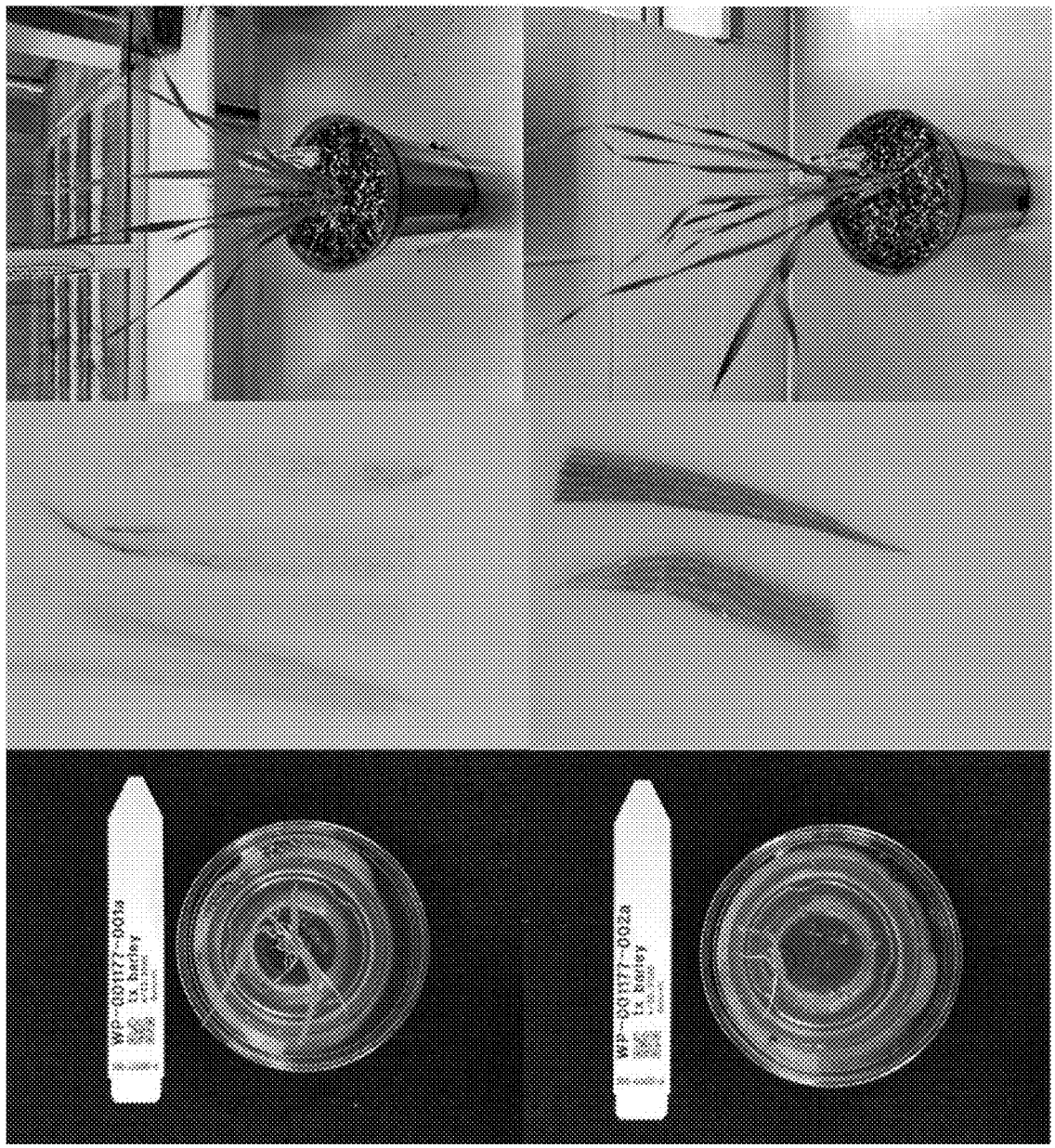
FIG. 33 shows T0 barley plants derived from mature embryo explants using hygromycin selection and expressing GUS.
Figure 34:
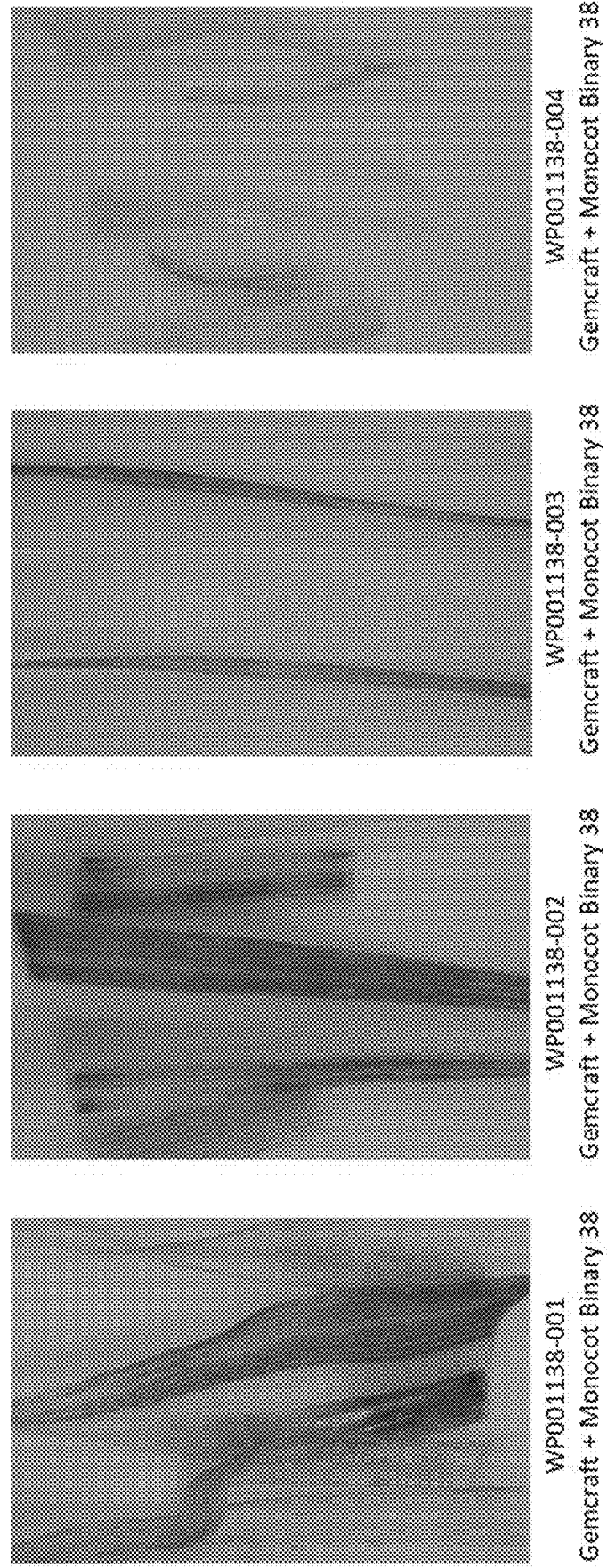
FIG. 34 shows stable GUS expression in leaves of T0 barley events WP001138-001 through -004 at handoff.
Figure 36:
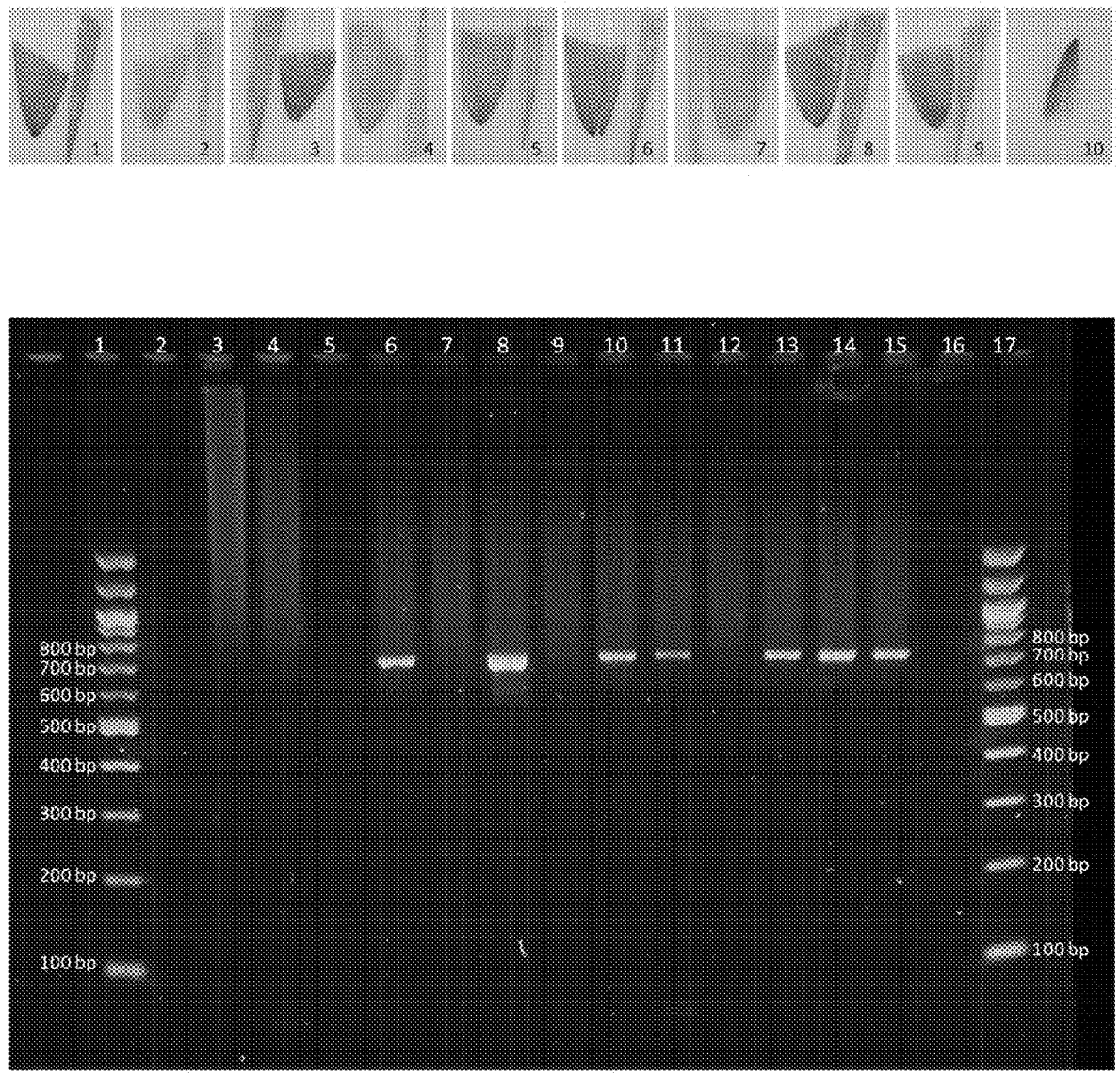
FIG. 36 shows GUS expression and tdTomato PCR in T1 leaves of Barley event WP412-1 (spike 1).
Figure 37:
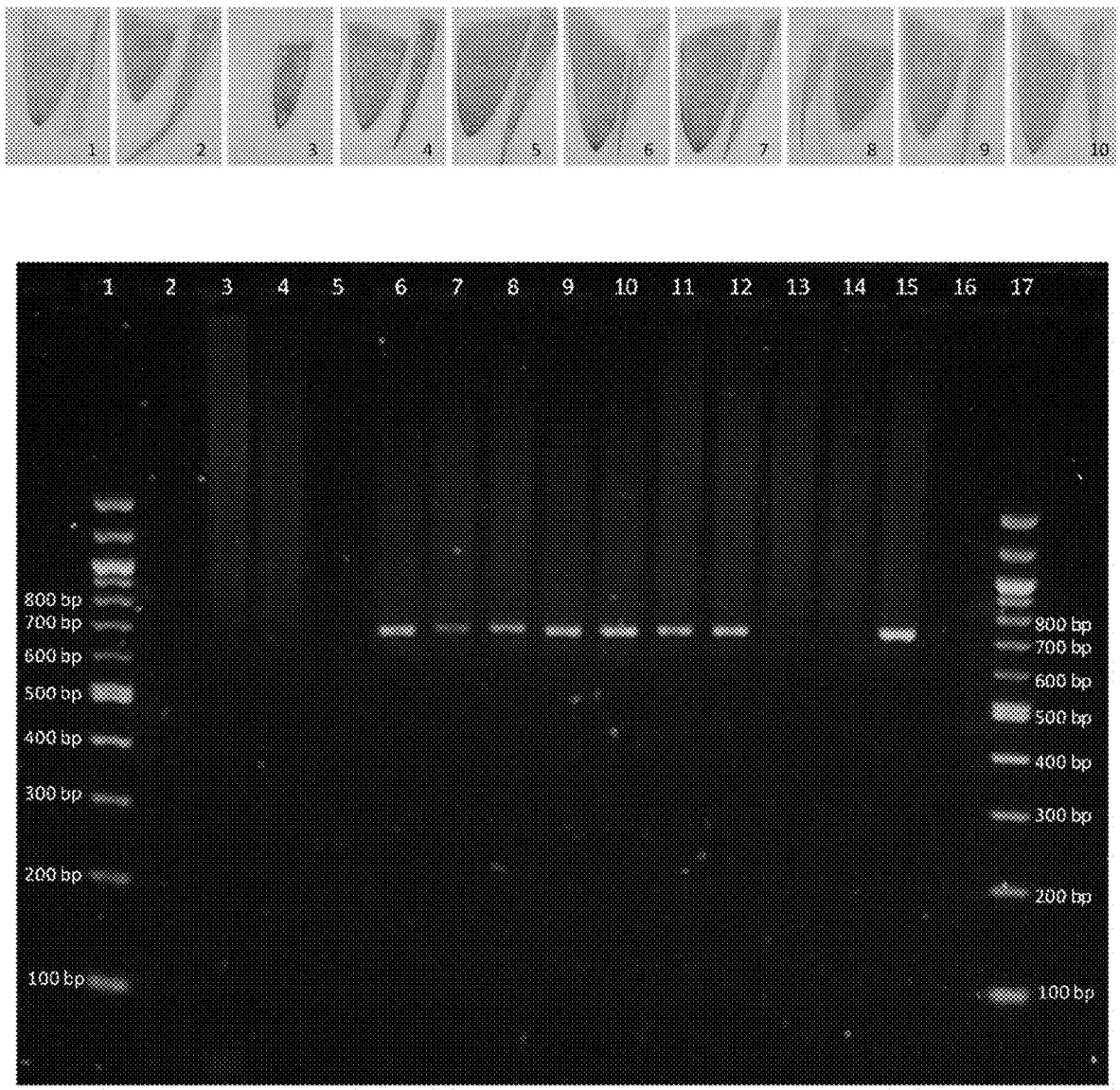
FIG. 37 shows GUS expression and tdTomato PCR in T1 leaves of Barley event WP412-3 (spike 6).

1. 3 minutes at 94 C for initial denaturation
2. 30 seconds at 94 C for denaturation
3. 30 seconds at 55 C for annealing
4. 1 minute at 72 C for primer extension
5. Cycle steps 2-4 34 more times (35 total cycles)
6. 10 minutes at 72 C for final primer extension As shown in FIG. 26, 13/13 leaves of WP412-1 are expressing GUS, and we were able to amplify an expected 701 bp fragment of tdTomato cassette (primers PCR35 and PCR36) in 10/12 leaves by PCR.

Barley event WP412-3 was generated from 10 mg/L BAP+1 mg/L 2,4-D bud induction, and at transplant had 20/24 leaves sampled positive for GUS expression, and 23/24 leaves positive for PCR of the tdTomato gene.

TABLE 9

Transformation metrics of Barley with nptII/G418 selection system in budding media screening experiments

| Binary | # Explants | First bud induction media | Second bud induction media | Regeneration media | # T0 plants | T0 plant pedigree | Putative TF |
|---|---|---|---|---|---|---|---|
| MB21 | 66 | 2L (MS, 8 g/L agarose I, 0.16 mg/L CuSO4, 3 mg/L TDZ, 1 mg/L 2,4-D) | 2L + 30 mg/L G418 | 2 (MS, 4g/L agarose I, 0.16 mg/L CuSO4) + 30 mg/L G418 | 2 | WP412-1 WP412-2 | 3.0% |
| MB21 | 66 | 2K (MS, 8 g/L agarose I, 0.16 mg/L CuSO4, 10 mg/L BAP, 1 mg/L 2,4-D) | 2K + 30 mg/L G418 | 2 (MS, 4g/L agarose I, 0.16 mg/L CuSO4) + 30 mg/L G418 | 1 | WP412-3 | 1.5% |
| MB21 | 15 | 4B (B5, 3.5 g/L phytagel, 1.25 mg/L CuSO4, 5 mg/L BAP, 0.5 mg/L 2,4-D) | none | 4 (B5, 3.5g/L phytagel, 1.25 mg/L CuSO4) + 60 mg/L G418 | 1 | WP412-4 | 6.7% |

TABLE 10

Transformation metrics of Barley with nptII/G418 selection system in follow-up experiments, where # Rooting shoots is # greening explants with shoots rooting on G418; and # T0 plants is # Rooting shoots expressing GUS

| Binary | # Explants | First bud induction media | Second bud induction media | Regeneration media | # Rooting shoots | # T0 plants | T0 plant pedigree | Putative TF |
|---|---|---|---|---|---|---|---|---|
| MB21 | 1058 | 3F (MS, 8 g/L agarose I, 0.16 mg/L $CuSO_4$, 10 mg/L BAP, 1 mg/L 2,4-D | none | 3 (MS, 3.5 g/L phytagel, 1.25 mg/L $CuSO_4$) + 60 mg/L G418 | 22 | 0 | n/a | 0.0% |
| MB21 | 849 | 3P (MS, 3.5 g/L phytagel, 1.25 mg/L $CuSO_4$, 2 mg/L TDZ, 1 mg/L 2,4-D | none | 3 (MS, 3.5 g/L phytagel, 1.25 mg/L $CuSO_4$) + 60 mg/L G418 | 23 | 0 | n/a | 0.0% |
| MB21 | 260 | 3O (MS, 3.5 g/L phytagel, 1.25 mg/L $CuSO_4$, 10 mg/L TDZ, 0.5 mg/L 2,4-D | none | 3 (MS, 3.5 g/L phytagel, 1.25 mg/L $CuSO_4$) + 60 mg/L G418 | 3 | 1 | WP001144-001 | 0.4% |
| MB21 | 260 | 4O (B5, 3.5 g/L phytagel, 1.25 mg/L $CuSO_4$, 10 mg/L TDZ, 0.5 mg/L 2,4-D | none | 4 (B5, 3.5 g/L phytagel, 1.25 mg/L $CuSO_4$) + 60 mg/L G418 | 0 | 0 | n/a | 0.0% |
| MB38 | 233 | 3P (MS, 3.5 g/L phytagel, 1.25 mg/L $CuSO_4$, 2 mg/L TDZ, 1 mg/L 2,4-D | none | 3 (MS, 3.5 g/L phytagel, 1.25 mg/L $CuSO_4$) + 60 mg/L G418 | 5 | 1 | WP001138-005 | 0.4% |
| MB38 | 200 | 3F (MS, 8 g/L agarose I, 0.16 mg/L $CuSO_4$, 10 mg/L BAP, 1 mg/L 2,4-D | none | 3 (MS, 3.5 g/L phytagel, 1.25 mg/L $CuSO_4$) + 60 mg/L G418 | 3 | 1 | WP001138-004 | 0.5% |
| MB38 | 120 | 3O (B5, 3.5 g/L phytagel, 1.25 mg/L $CuSO_4$, 10 mg/L TDZ, 0.5 mg/L 2,4-D | none | 3 (MS, 3.5 g/L phytagel, 1.25 mg/L $CuSO_4$) + 60 mg/L G418 | 3 | 3 | WP001138-006, -007, and -011 | 2.5% |
| MB38 | 160 | 4O (B5, 3.5 g/L phytagel, 1.25 mg/L $CuSO_4$, 10 mg/L TDZ, 0.5 mg/L 2,4-D | none | 4 (B5, 3.5 g/L phytagel, 1.25 mg/L $CuSO_4$) + 60 mg/L G418 | 19 | 10 | WP001138-001, -002, -003, -008, -009, -012, -013, -016, -017, and -020 | 6.3% |
| MB38 | 120 | 3O (B5, 3.5 g/L phytagel, 1.25 mg/L $CuSO_4$, 10 mg/L TDZ, 0.5 mg/L 2,4-D | none (*this treatment used a 2 min explant sanitization) | 3 (MS, 3.5 g/L phytagel, 1.25 mg/L $CuSO_4$) + 60 mg/L G418 | 7 | 5 | WP001138-010, -014, -015, 018, and -019 | 4.2% |
| MB38 | 160 | 4O (B5, 3.5 g/L phytagel, 1.25 mg/L $CuSO_4$, 10 mg/L TDZ, 0.5 mg/L 2,4-D | none (*this treatment used a 2 min explant sanitization) | 4 (B5, 3.5 g/L phytagel, 1.25 mg/L $CuSO_4$) + 60 mg/L G418 | 0 | 0 | n/a | 0.0% |
| MB21 | 1160 | 2K (MS, 8 g/L agarose I, 0.16 mg/L $CuSO_4$, 10 mg/L BAP, 1 mg/L 2,4-D | 2K + 30 mg/L G418 | 2 (MS, 4 g/L agarose I, 0.16 mg/L $CuSO_4$) + 30 mg/L G418 | 24 | 1 | WP001144-002 | 0.1% |
| MB38 | 1200 | 2K (MS, 8 g/L agarose I, 0.16 mg/L $C11SO4$, 10 mg/L BAP, 1 mg/L 2,4-D | 2K + 30 mg/L G418 | 2 (MS, 4 g/L agarose I, 0.16 mg/L $CuSO_4$) + 30 mg/L G418 | 1 | 0 | n/a | 0.0% |
| MB21 | 999 | 2L (MS, 8 g/L agarose I, 0.16 mg/L $CuSO_4$, 3 mg/L TDZ, 1 mg/L 2,4-D | 2L + 30 mg/L G418 | 2 (MS, 4 g/L agarose I, 0.16 mg/L $CuSO_4$) + 30 mg/L G418 | 9 | 7 | WP001144-003-009 | 0.7% |
| MB38 | 360 | 2L (MS, 8 g/L agarose I, 0.16 mg/L $CuSO_4$, 3 mg/L TDZ, 1 mg/L 2,4-D | 2L + 30 mg/L G418 | 2 (MS, 4 g/L agarose I, 0.16 mg/L $CuSO_4$) + 30 mg/L G418 | 2 | 2 | WP001138-021; -028 | 0.6% |
| MB38 | 360 | 2L (MS, 8 g/L agarose I, 0.16 mg/L $CuSO_4$, 3 mg/L TDZ, 1 mg/L 2,4-D | 2L + 30 mg/L G418 | 4 (B5, 3.5 g/L phytagel, 1.25 mg/L $CuSO_4$) + 60 mg/L G418 | 17 | 10 | WP001138-022, 023, -024, -025; -029, -032, -033; -037; -038, -044 | 2.8% |
| MB38 | 230 | 2M (MS, 8 g/L agarose I, 0.16 mg/L $CuSO_4$, 10 mg/L TDZ, 1 mg/L 2,4-D | none | 2 (MS, 4 g/L agarose I, 0.16 mg/L $CuSO_4$) + 60 mg/L G418 | 1 | 0 | | |
| MB38 | 240 | 2M (MS, 8 g/L agarose I, 0.16 mg/L $CuSO_4$, 10 mg/L TDZ, 1 mg/L 2,4-D | none | 4 (B5, 3.5 g/L phytagel, 1.25 mg/L $CuSO_4$) + 60 mg/L G418 | 6 | 4 | WP001138-042, -043, -046, -047 | 1.7% |

TABLE 10-continued

Transformation metrics of Barley with nptII/G418 selection system in follow-up experiments, where # Rooting shoots is # greening explants with shoots rooting on G418; and # T0 plants is # Rooting shoots expressing GUS

| Binary | # Explants | First bud induction media | Second bud induction media | Regeneration media | # Rooting shoots | # T0 plants | T0 plant pedigree | Putative TF |
|---|---|---|---|---|---|---|---|---|
| MB38 | 240 | 4O (B5, 3.5 g/L phytagel, 1.25 mg/L $CuSO_4$, 10 mg/L TDZ, 0.5 mg/L 2,4-D) | none | 2 (MS, 4 g/L agarose I, 0.16 mg/L $CuSO_4$) + 60 mg/L G418 | 1 | 1 | WP001138-40 | 0.4% |
| MB38 | 220 | 4O (B5, 3.5 g/L phytagel, 1.25 mg/L $CuSO_4$, 10 mg/L TDZ, 0.5 mg/L 2,4-D) | none | 4 (B5, 3.5 g/L phytagel, 1.25 mg/L $CuSO_4$) + 60 mg/L G418 | 3 | 2 | WP001138-036; -041 | 0.9% |

We did not recover rooted T0 events from budding medium 2G-2J; 3A-3R, or 4A, 4C-4R, but some of these medium had relatively high multiple budding/shooting response and were tested again in follow-up tests (screening tests also had relatively low initial numbers).

We also ran small scale experiments investigating the use of fipexide during the bud induction phase, based on research where it was found to both enhance callus formation and shoot regeneration.(12) After 2 weeks on bud induction media we found the multiple shooting/budding phenotype in the 3 ppm TDZ, 1 ppm 2,4-D treatment as well as the 3 ppm TDZ, 10 ppm fipexide treatment. Explants on 3 ppm TDZ, 10 ppm fipexide also looked healthier than controls on 2,4-D media. We observed germinating phenotype on the no-PGR control plate as well as the 10 ppm fipexide plate where TDZ was removed; and explant sensitivity on 100 ppm fipexide. We followed this experiment up examining removal of 2,4-D from the bud induction phase, as well as its replacement with either picloram or fipexide.

We also tested increased G418 selection levels and alternate selection systems to ascertain if we could minimize the escape ratio of #rooted shoots to #T0 plants (#rooted shoots expressing GUS). We were able to obtain T0 plants which rooted on hygromycin and expressed GUS.

TABLE 11

Transformation metrics of Barley in auxin replacement studies

| Binary | # Explants | First bud induction media | Second bud induction media | Regeneration media | # Rooting shoots | # T0 plants | T0 plant pedigree | Putative TF |
|---|---|---|---|---|---|---|---|---|
| MB38 | 64 | 2L without PGRs (MS, 8 g/L agarose I, 0.16 mg/L $CuSO_4$) | none | 4 (B5, 3.5 g/L phytagel, 1.25 mg/L $CuSO_4$) + 60 mg/L G418 | 1 | 0 | n/a | 0.0% |
| MB38 | 80 | 2L (MS, 8 g/L agarose I, 0.16 mg/L $CuSO_4$, 3 mg/L TDZ, 1 mg/L 2,4-D) | none | 4 (B5, 3.5 g/L phytagel, 1.25 mg/L $CuSO_4$) + 60 mg/L G418 | 7 | 1 | WP001138-026 | 1.3% |
| MB38 | 80 | 2L fix (MS, 8 g/L agarose I, 0.16 mg/L $CuSO_4$, 3 mg/L TDZ, 10 mg/L fipexide) | none | 4 (B5, 3.5 g/L phytagel, 1.25 mg/L $CuSO_4$) + 60 mg/L G418 | 10 | 7 | WP001138-027; -030, -031, -034, -035; -039, -045 | 8.8% |
| MB38 | 80 | 2L fix without TDZ (MS, 8 g/L agarose I, 0.16 mg/L $CuSO_4$, 10 mg/L fipexide) | none | 4 (B5, 3.5 g/L phytagel, 1.25 mg/L $CuSO_4$) + 60 mg/L G418 | 1 | 0 | n/a | 0.0% |
| MB38 | 80 | 2L 100 fix without TDZ (MS, 8 g/L agarose I, 0.16 mg/L $CuSO_4$, 100 mg/L fipexide) | none | 4 (B5, 3.5 g/L phytagel, 1.25 mg/L $CuSO_4$) + 60 mg/L G418 | 0 | 0 | n/a | 0.0% |
| MB38 | 255 | 4O (B5, 3.5 g/L phytagel, 1.25 mg/L $CuSO_4$, 10 mg/L TDZ, 0.5 mg/L 2,4-D) | none | 4 (B5, 3.5 g/L phytagel, 1.25 mg/L $CuSO_4$) + 60 mg/L G418 | 8 | 4 | WP001138-048; -049, -051, -052 | 1.6% |
| MB38 | 245 | 4O minus 2,4-D (B5, 3.5 g/L phytagel, 1.25 mg/L $CuSO_4$, 10 mg/L TDZ) | none | 4 (B5, 3.5 g/L phytagel, 1.25 mg/L $CuSO_4$) + 60 mg/L G418 | 6 | 1 | WP001138-053 | 0.4% |
| MB38 | 255 | 4O pic (B5, 3.5 g/L phytagel, 1.25 mg/L $CuSO_4$, 10 mg/L TDZ, 0.5 mg/L picloram) | none | 4 (B5, 3.5 g/L phytagel, 1.25 mg/L $CuSO_4$) + 60 mg/L G418 | 4 | 0 | | |
| MB38 | 255 | 4O fix (B5, 3.5 g/L phytagel, 1.25 mg/L $CuSO_4$, 10 mg/L TDZ, 10 mg/L fipexide) | none | 4 (B5, 3.5 g/L phytagel, 1.25 mg/L $CuSO_4$) + 60 mg/L G418 | 6 | 3 | WP001138-050, plants 1, 2 | 1.2% |

TABLE 12

Transformation metrics of Barley in selection optimization studies.

| Binary | # Explants | First bud induction media | Second bud induction media | Regeneration media | # Rooting shoots | # T0 plants | T0 plant pedigree | Putative TF |
|---|---|---|---|---|---|---|---|---|
| MB30 | 464 | 4O (B5, 3.5 g/L phytagel, 1.25 mg/L CuSO$_4$, 10 mg/L TDZ, 0.5 mg/L 2,4-D | none | 4 (B5, 3.5 g/L phytagel, 1.25 mg/L CuSO$_4$) + 5 mg/L bialaphos | 15 | 2 | WP001188-001, -002 | 0.4% |
| MB35 | 334 | 4O (B5, 3.5 g/L phytagel, 1.25 mg/L CuSO$_4$, 10 mg/L TDZ, 0.5 mg/L 2,4-D | none | 4 (B5, 3.5 g/L phytagel, 1.25 mg/L CuSO$_4$) + 20 mg/L hygromycin | 3 | 3 | WP001177-001-003, | 0.9% |
| MB38 | 271 | 4O (B5, 3.5 g/L phytagel, 1.25 mg/L CuSO$_4$, 10 mg/L TDZ, 0.5 mg/L 2,4-D | none | 4 (B5, 3.5 g/L phytagel, 1.25 mg/L CuSO$_4$) + 90 mg/L G418 | 3 | 2 | WP001138-054, -055 | 0.7% |
| MB38 | 260 | 4O (B5, 3.5 g/L phytagel, 1.25 mg/L CuSO$_4$, 10 mg/L TDZ, 0.5 mg/L 2,4-D | none | 4 (B5, 3.5 g/L phytagel, 1.25 mg/L CuSO$_4$) + 120 mg/L G418 | 3 | 2 | WP001138-056, plant 3 | 0.8% |

TABLE 13

GUS expression and tdTomato integration metrics of initial T0 Barley events

| T0 event | % leaves expressing GUS at handoff | % leaves PCR positive for tdTomato at handoff | % leaves expressing GUS at transplant | % leaves PCR positive for tdTomato at transplant |
|---|---|---|---|---|
| WP412-1 | 2/5 = 40% | not determined | 13/13 = 100% | 10/12 = 83% |
| WP412-2 | 2/7 = 29% | 1/5 = 20% | 6/24 = 25% | not determined |
| WP412-3 | 5/7 = 71% | 2/5 = 40% | 20/24 = 83% | 23/24 = 96% |

TABLE 14

GUS expression in subsequent T0 Barley events

| T0 event | % leaves expressing GUS at handoff | % leaves expressing GUS at transplant |
|---|---|---|
| WP412-4 | 1/4 = 25% | 3/24 = 13% |
| WP001138-005 | 1/4 = 25% | 10/10 = 100% |
| WP001138-004 | 3/6 = 50% | 4/10 = 40% |
| WP001138-003 | 2/8 = 25% | 7/10 = 70% |
| WP001138-001 | 6/8 = 75% | 1/10 = 10% |
| WP001138-002 | 3/4 = 75% | 7/10 = 70% |
| WP001138-006 | 2/5 = 40% | 0/10 = 0% |
| WP001138-007 | 2/5 = 40% | 10/10 = 100% |
| WP001138-008 | 2/5 = 40% | 2/10 = 20% |
| WP001138-009 | 2/8 = 25% | plant died |
| WP001138-010 | 5/6 = 83% | 1/10 = 10% |
| WP001144-001 | 2/2 = 100% | 5/10 = 50% |
| WP001138-011 | 2/8 = 25% | 8/10 = 80% |
| WP001138-012 | 3/3 = 100% | 0/10 = 0% |
| WP001138-013 | 3/4 = 75% | 10/10 = 100% |
| WP001138-016 | 1/5 = 20% | 0/10 = 0% |
| WP001138-014 | 4/4 = 100% | 8/10 = 80% |
| WP001138-015 | 1/4 = 25% | 1/10 = 10% |
| WP001144-002 | 4/6 = 67% | 7/10 = 70% |
| WP001138-017 | 3/6 = 50% (roots GUS + as well) | 9/10 = 90% |
| WP001138-018 | 2/7 = 29% | 9/10 = 90% |
| WP001138-019 | 5/6 = 83% | 4/10 = 40% |
| WP001138-020 | 6/8 = 75% | 9/10 = 90% |
| WP001144-003 | 4/5 = 80% | 8/10 = 80% |
| WP001144-004 | 4/7 = 57% | 9/10 = 90% |
| WP001144-005 | 7/10 = 70% | 10/10 = 100% |
| WP001144-006 | 3/4 = 75% | 9/10 = 90% |
| WP001138-021 | 7/11 = 64% | 8/10 = 80% |
| WP001138-022 | 5/7 = 71% | 7/10 = 70% |
| WP001138-023 | 2/5 = 40% | 10/10 = 100% |
| WP001138-024 | 4/8 = 50% | 10/10 = 100% |
| WP001138-025 | 8/8 = 100% | 10/10 = 100% |
| WP001138-026 | 1/2 = 50% | 1/10 = 10% |
| WP001138-027 | 4/8 = 50% | 2/10 = 20% |
| WP001144-007 | 7/7 = 100% | 10/10 = 100% |
| WP001144-008 | 2/6 = 33% | 4/10 = 40% |
| WP001138-028 | 1/9 = 11% | 4/10 = 40% |
| WP001138-029 | 3/5 = 60% | 10/10 = 100% |
| WP001138-030 | 5/10 = 50% | 9/10 = 90% |
| WP001138-031 | 2/6 = 33% | 1/10 = 10% |
| WP001138-032 | 3/3 = 100% | 10/10 = 100% |
| WP001138-033 | 2/9 = 22% | 2/10 = 20% |
| WP001138-034 | 1/8 = 13% | 5/10 = 50% |
| WP001138-035 | 5/10 = 50% | 8/10 = 80% |
| WP001138-036 | 5/5 = 100% | 8/10 = 80% |
| WP001138-037 | 2/8 = 25% | 9/10 = 90% |
| WP001138-038 | 1/6 = 17% | 4/10 = 40% |
| WP001138-039 | 1/6 = 17% | 2/10 = 20% |
| WP001138-040 | 1/7 = 14% | 0/10 = 0% |
| WP001138-041 | 3/5 = 60% | 6/10 = 60% |
| WP001177-001 | 3/5 = 60% | 1/10 = 10% |
| WP001144-009 | 4/7 = 57% | 3/10 = 30% |
| WP001138-042 | 8/8 = 100% | 10/10 = 100% |
| WP001138-043 | 6/9 = 67% | 10/10 = 100% |
| WP001177-002 | 2/2 = 100% | 10/10 = 100% |
| WP001138-044 | 5/5 = 100% | 10/10 = 100% |
| WP001177-003 | 2/2 = 100% | 1/10 = 10% |
| WP001138-045 | 2/3 = 67% | 6/10 = 60% |
| WP001138-046 | 2/7 = 29% | 5/10 = 50% |
| WP001138-047 | 2/6 = 33% | 8/10 = 80% |
| WP001188-001 | 2/3 = 67% | 0/10 = 0% |
| WP001188-002 | 3/4 = 75% | 10/10 = 100% |
| WP001138-048 | 4/4 = 100% | 10/10 = 100% |
| WP001138-049 | 3/5 = 60% | 10/10 = 100% |
| WP001138-050 | 5/7 = 71% | 10/10 = 100% |

TABLE 14-continued

GUS expression in subsequent T0 Barley events

| T0 event | % leaves expressing GUS at handoff | % leaves expressing GUS at transplant |
|---|---|---|
| WP001138-053 | 3/3 = 100% | |
| WP001138-051 | 3/3 = 100% | |
| WP001138-052 | 5/6 = 83% | |
| WP001138-054 | 2/5 = 40% | |
| WP001138-055 | 1/2 = 50% | |
| WP001138-056 | 4/5 = 80% | |
| Plant 1 | 4/10 = 40% | |
| Plant 2 | 3/8 = 38% | |
| Plant 3 | 2/7 = 29% | |

TABLE 15

Monocot Basal Regeneration Media 2

| Ingredients and Notes | Amount to add per liter (grams) |
|---|---|
| MS Salts with Gamborg B5 Vitamins (Phytotech M404) | 4.44 |
| Maltose | 30 |
| Cupric Sulfate (CuSO4) (1 mg/ml) | 0.160 ml |
| Cleary's | 0.06 |
| pH to 5.8 with 1N KOH | |
| Agarose I | 4.00 |
| autoclave | |
| Add the following post-autoclave: | |
| Carbenicillin (100 mg/ml stock) | Use at 2 ml per Liter (200 mg/L) |
| Cefotaximine (100 mg/ml stock) | Use at 2 ml per Liter (200 mg/L) |
| Timetin (150 mg/ml stock) | Use at 1 ml per Liter (150 mg/L) |
| Selection | as specified |
| Container | Deep plates |
| Distribution | 50 ml/plate |

TABLE 16

Monocot Basal Regeneration Media 3

| Ingredients and Notes | Amount to add per liter (grams) |
|---|---|
| MS Salts with Gamborg BS Vitamins (Phytotech M404) | 4.44 |
| Maltose | 30 |
| Cupric Sulfate (CuSO4) (1 mg/ml) | 1.25 ml |
| Cleary's | 0.06 |
| pH to 5.8 with 1N KOH | |
| Phytagel | 3.50 |
| autoclave | |
| Add the following post-autoclave: | |
| Carbenicillin (100 mg/ml stock) | Use at 2 ml per Liter (200 mg/L) |
| Cefotaximine (100 mg/ml stock) | Use at 2 ml per Liter (200 mg/L) |
| Timetin (150 mg/ml stock) | Use at 1 ml per Liter (150 mg/L) |
| Selection | as specified |
| Container | Deep plates |
| Distribution | 50 ml/plate |

TABLE 17

Monocot Basal Regeneration Media 4

| Ingredients and Notes | Amount to add per liter (grams) |
|---|---|
| Phytotechnology Laboratories B5 salts G398 | 3.21 |
| Maltose | 30 |
| Cupric Sulfate (CuSO4) (1 mg/ml) | 1.25 ml |
| Cleary's | 0.06 |
| pH to 5.8 with 1N KOH | |
| Phytagel | 3.50 |
| autoclave | |
| Add the following post-autoclave: | |
| Carbenicillin (100 mg/ml stock) | Use at 2 ml per Liter (200 mg/L) |
| Cefotaximine (100 mg/ml stock) | Use at 2 ml per Liter (200 mg/L) |
| Timetin (150 mg/ml stock) | Use at 1 ml per Liter (150 mg/L) |
| Selection | as specified |
| Container | Deep plates |
| Distribution | 50 ml/plate |

Germline Transmission in T1 Barley

Confirmation of germline transmission is critical in meristem-based transformation systems as Barley apical meristem has two cell layers, L1 and L2, and only the L2 layer gives rise to gametes.(13) We separated 10 T1 seeds from 12 spikes each for the WP412-1 and WP412-3 events and planted them to determine germline status of these events. After approximately 8 days T1 plants were sampled for GUS by incubated leaf samples at 37° C. overnight in X-gluc substrate, then clearing the leaves in 70% ethanol as previously done for T0 leaf tissue. We found both the WP412-1 and WP412-3 events, which had a relatively high percentage of leaves expressing GUS as transplants, were germline, as determined by the presence of GUS in the T1 leaf sample.

TABLE 18

Germline transmission in Barley event WP412-1 (100% leaves expressing GUS at transplant)

| Event | Spike | # T1 Seeds Planted | # T1 Plants Germinated | % Germination | # T1 Plants GUS positive | % GUS positive T1 Plants |
|---|---|---|---|---|---|---|
| WP412-1 | 1 | 10 | 10 | 100% | 7 | 70% |
| WP412-1 | 2 | 10 | 7 | 70% | 3 | 43% |
| WP412-1 | 3 | 10 | 8 | 80% | 7 | 88% |
| WP412-1 | 4 | 10 | 5 | 50% | 5 | 100% |
| WP412-1 | 5 | 10 | 5 | 50% | 4 | 80% |
| WP412-1 | 6 | 10 | 7 | 70% | 5 | 71% |
| WP412-1 | 7 | 10 | 9 | 90% | 7 | 78% |
| WP412-1 | 8 | 10 | 9 | 90% | 8 | 89% |

TABLE 18-continued

Germline transmission in Barley event WP412-1
(100% leaves expressing GUS at transplant)

| Event | Spike | # T1 Seeds Planted | # T1 Plants Germinated | % Germination | # T1 Plants GUS positive | % GUS positive T1 Plants |
|---|---|---|---|---|---|---|
| WP412-1 | 9 | 10 | 10 | 100% | 6 | 60% |
| WP412-1 | 10 | 10 | 10 | 100% | 7 | 70% |
| WP412-1 | 11 | 10 | 10 | 100% | 8 | 80% |
| WP412-1 | 12 | 10 | 8 | 80% | 6 | 75% |
| WP412-1 | 1-12 | 120 | 98 | 82% | 73 | 74% |

TABLE 19

Germline transmission in Barley event WP412-3 (83% leaves expressing GUS at transplant)

| Event | Spike | # T1 Seeds Planted | # T1 Plants Germinated | % Germination | # T1 Plants GUS positive | % GUS positive T1 Plants |
|---|---|---|---|---|---|---|
| WP412-3 | 1 | 10 | 6 | 60% | 5 | 83% |
| WP412-3 | 2 | 10 | 8 | 80% | 6 | 75% |
| WP412-3 | 3 | 10 | 7 | 70% | 5 | 71% |
| WP412-3 | 4 | 5 | 3 | 60% | 3 | 100% |
| WP412-3 | 5 | 10 | 9 | 90% | 5 | 56% |
| WP412-3 | 6 | 10 | 10 | 100% | 8 | 80% |
| WP412-3 | 7 | 10 | 9 | 90% | 7 | 78% |
| WP412-3 | 8 | 10 | 6 | 60% | 4 | 67% |
| WP412-3 | 9 | 10 | 9 | 90% | 5 | 56% |
| WP412-3 | 10 | 10 | 3 | 30% | 3 | 100% |
| WP412-3 | 11 | 10 | 5 | 50% | 5 | 100% |
| WP412-3 | 12 | 10 | 6 | 60% | 4 | 67% |
| WP412-3 | 1-12 | 115 | 81 | 70% | 60 | 74% |

We found the WP412-2 event, which had a relatively low percentage of leaves expressing GUS at transplant, was either an L1 chimera or sufficiently chimeric that we could not detect GUS at T1. The WP412-4, which also had a relatively low percentage of leaves expressing GUS at transplant, was germline but very chimeric, with only T1 seed from one spike out of 12 expressing GUS.

TABLE 20

Germline transmission in Barley event WP412-2 (25% leaves expressing GUS at transplant)

| Event | Spike | # T1 Seeds Planted | # T1 Plants Germinated | % Germination | # T1 Plants GUS positive | % GUS positive T1 Plants |
|---|---|---|---|---|---|---|
| WP412-2 | 1 | 12 | 11 | 92% | 0 | 0% |
| WP412-2 | 2 | 12 | 10 | 83% | 0 | 0% |
| WP412-2 | 3 | 12 | 11 | 92% | 0 | 0% |
| WP412-2 | 4 | 12 | 11 | 92% | 0 | 0% |
| WP412-2 | 5 | 12 | 12 | 100% | 0 | 0% |
| WP412-2 | 6 | 12 | 12 | 100% | 0 | 0% |
| WP412-2 | 7 | 12 | 11 | 92% | 0 | 0% |
| WP412-2 | 8 | 12 | 12 | 100% | 0 | 0% |
| WP412-2 | 9 | 12 | 12 | 100% | 0 | 0% |
| WP412-2 | 10 | 12 | 10 | 83% | 0 | 0% |
| WP412-2 | 11 | 12 | 9 | 75% | 0 | 0% |
| WP412-2 | 12 | 12 | 11 | 92% | 0 | 0% |
| WP412-2 | 1-12 | 144 | 132 | 92% | 0 | 0% |

TABLE 21

Germline transmission in Barley event WP412-4 (13% leaves expressing GUS at transplant)

| Event | Spike | # T1 Seeds Planted | # T1 Plants Germinated | % Germination | # T1 Plants GUS positive | % GUS positive T1 Plants |
|---|---|---|---|---|---|---|
| WP412-4 | 1 | 12 | 11 | 92% | 0 | 0% |
| WP412-4 | 2 | 12 | 10 | 83% | 0 | 0% |
| WP412-4 | 3 | 12 | 9 | 75% | 0 | 0% |
| WP412-4 | 4 | 12 | 8 | 67% | 0 | 0% |
| WP412-4 | 5 | 12 | 11 | 92% | 11 | 100% |
| WP412-4 | 6 | 12 | 11 | 92% | 0 | 0% |
| WP412-4 | 7 | 12 | 11 | 92% | 0 | 0% |
| WP412-4 | 8 | 12 | 12 | 100% | 0 | 0% |
| WP412-4 | 9 | 12 | 11 | 92% | 0 | 0% |
| WP412-4 | 10 | 12 | 8 | 67% | 0 | 0% |
| WP412-4 | 11 | 12 | 11 | 92% | 0 | 0% |
| WP412-4 | 12 | 12 | 12 | 100% | 0 | 0% |
| WP412-4 | 1-12 | 144 | 125 | 87% | 11 | 9% |

Particle-Mediated Transformation of Barley Mature Embryo Explants

Figure 38:
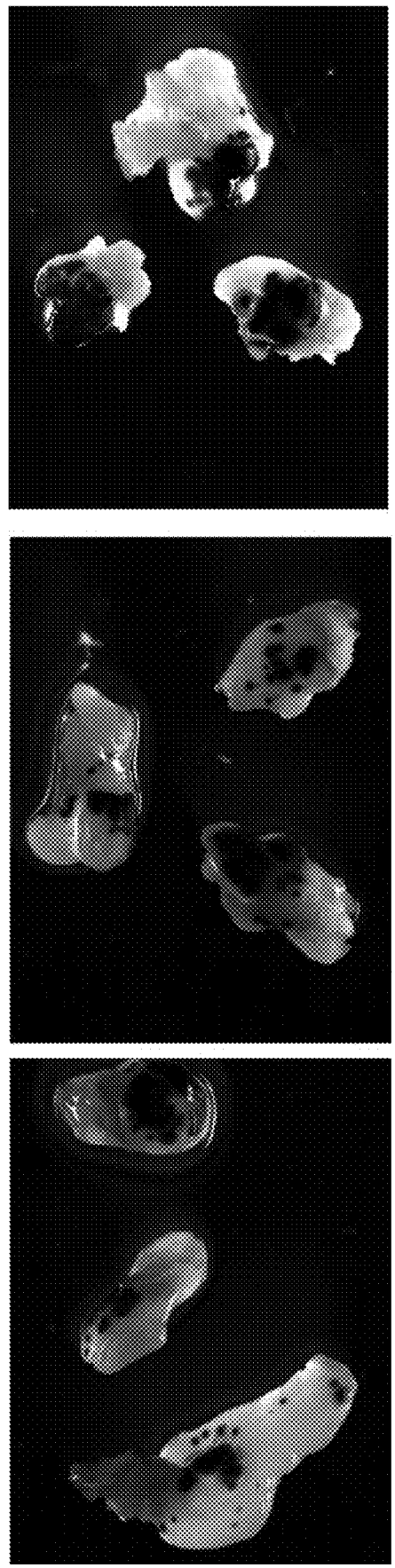
FIG. 38 shows GUS transient expression in Barley mature embryo explants bombarded with VS224 DNA on BioRad PDS-1000 at 6 cm distance, 1350 psi rupture disk.

Cultured shoot apices of maize on shoot multiplication media have been transformed by particle bombardment,(14) and it may also be possible to transform elite varieties of Barley with particle gun prior to this multiplication based on transient GUS expression (FIG. 38).

Examples in Other Monocots: Maize (*Zea mays* L.)

Figure 39:
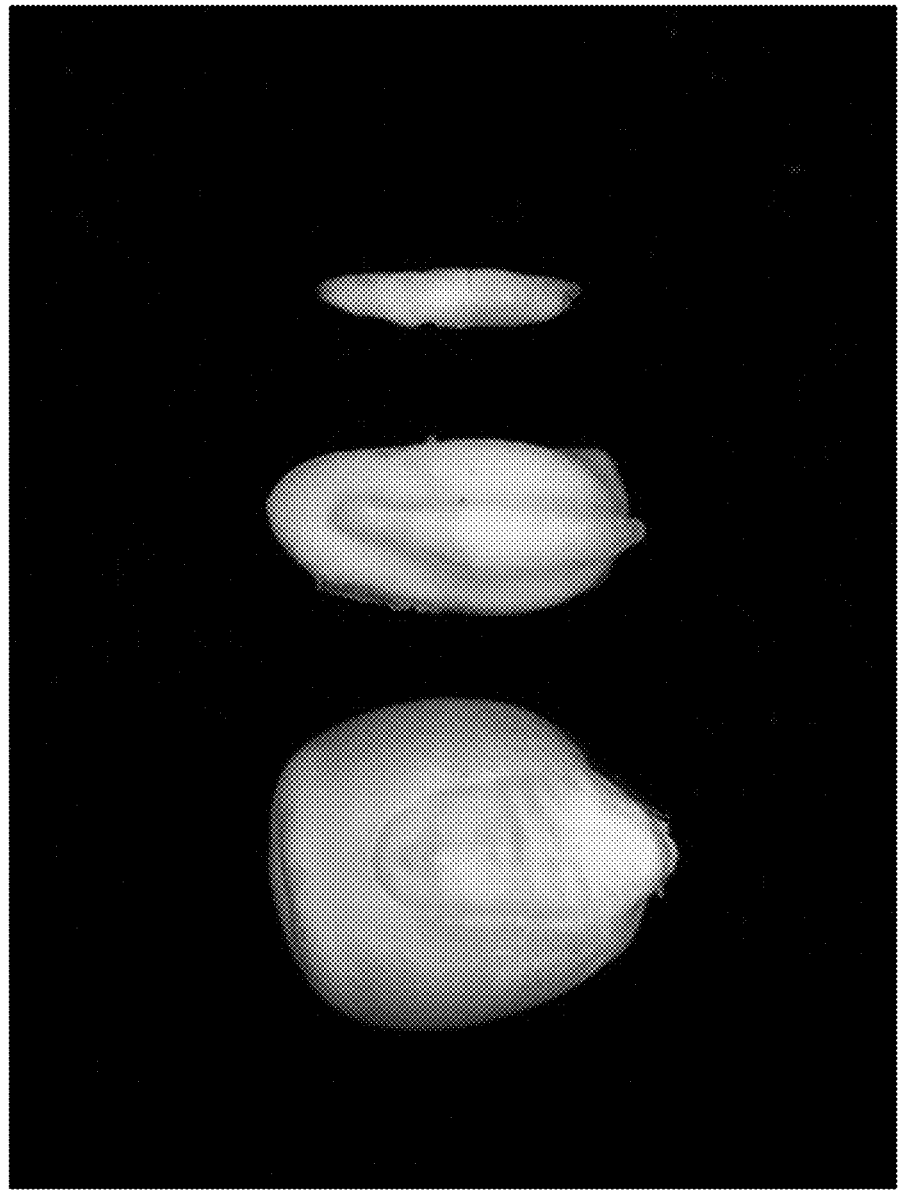
FIG. 39 shows Maize seed (left); mature maize embryo (center); and mature maize embryo axis (right).
Figure 40:
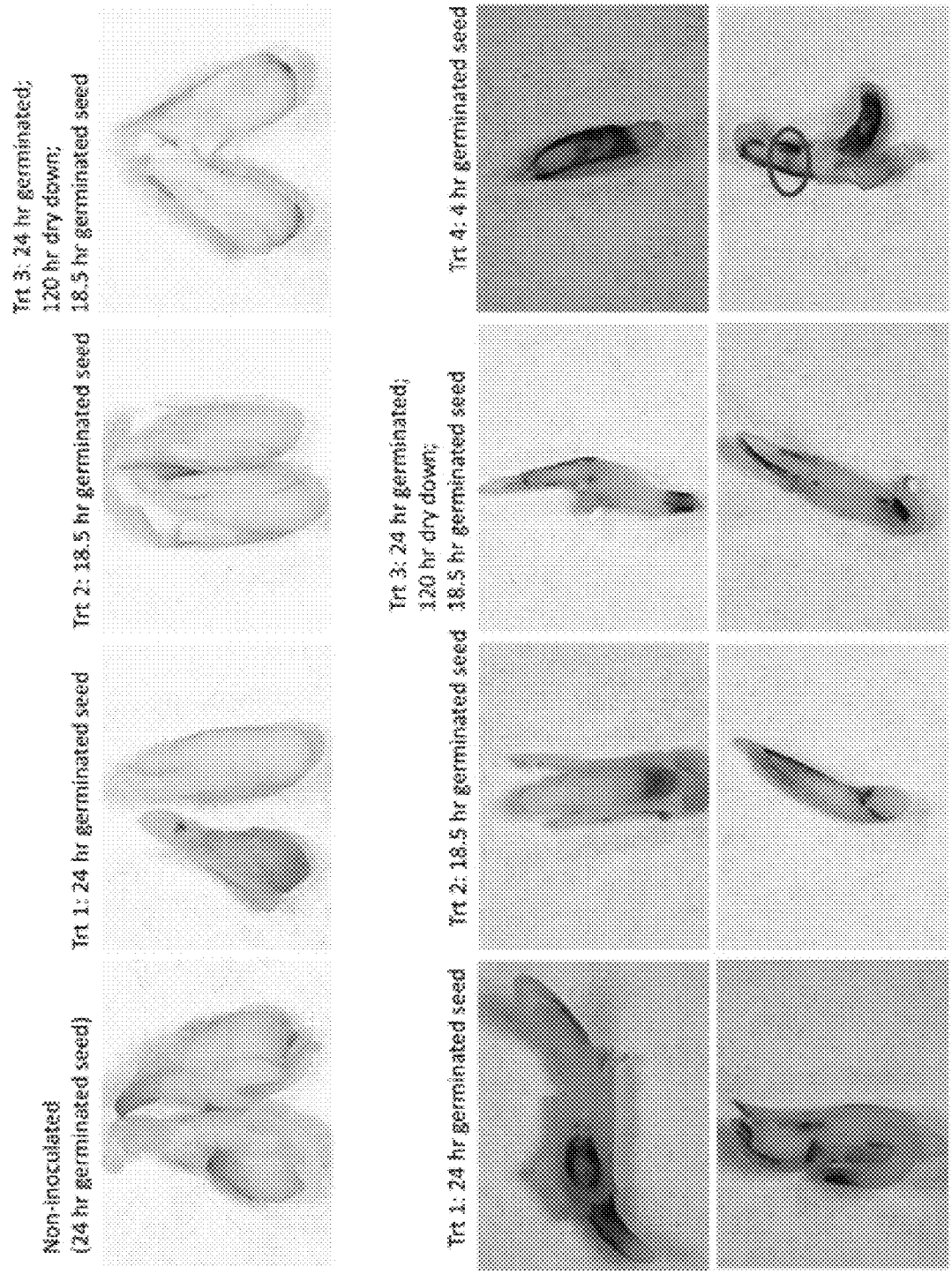
FIG. 40 shows GUS transient expression in Maize mature embryo explants (Fbll variety) through application of force and partial removal of scutellum.
Figure 41:
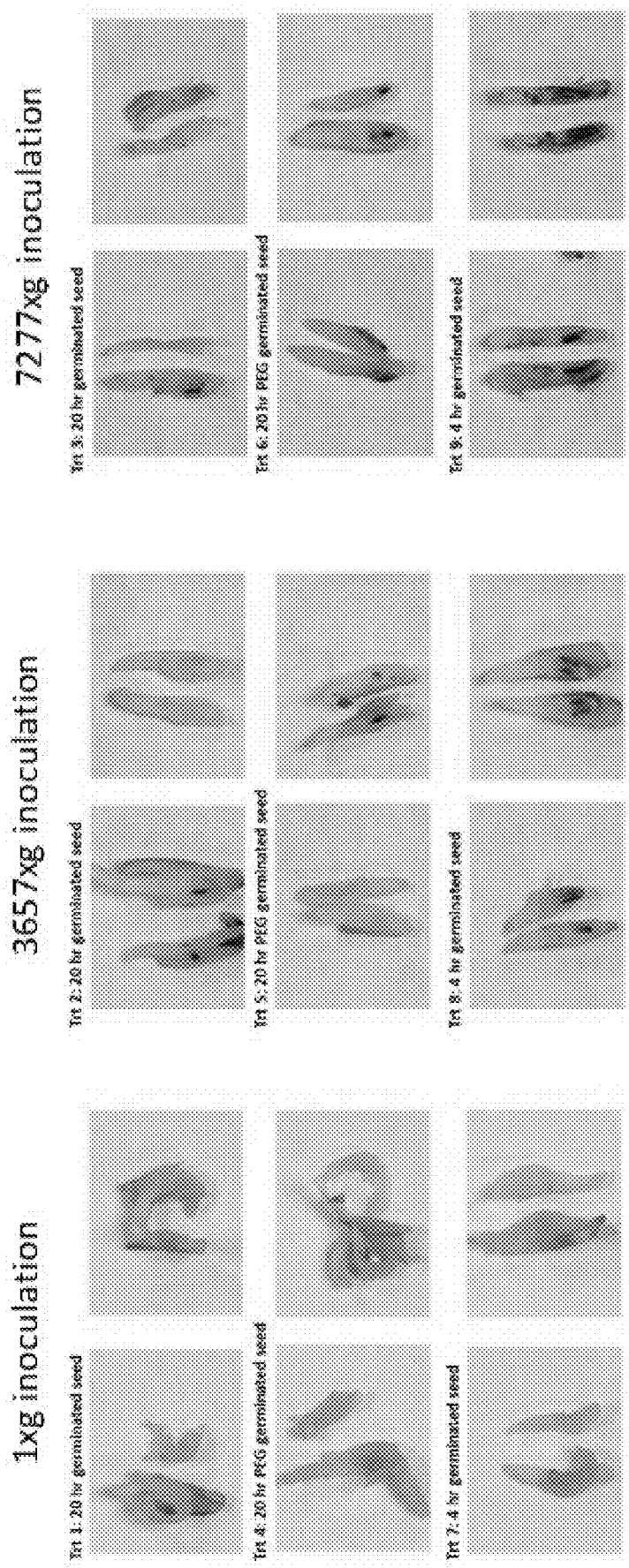
FIG. 41 shows GUS transient expression in Maize mature embryo explants (Fbll variety) through application of increasing levels of force, partial removal of scutellum, and varying germination timings.
Figure 42:
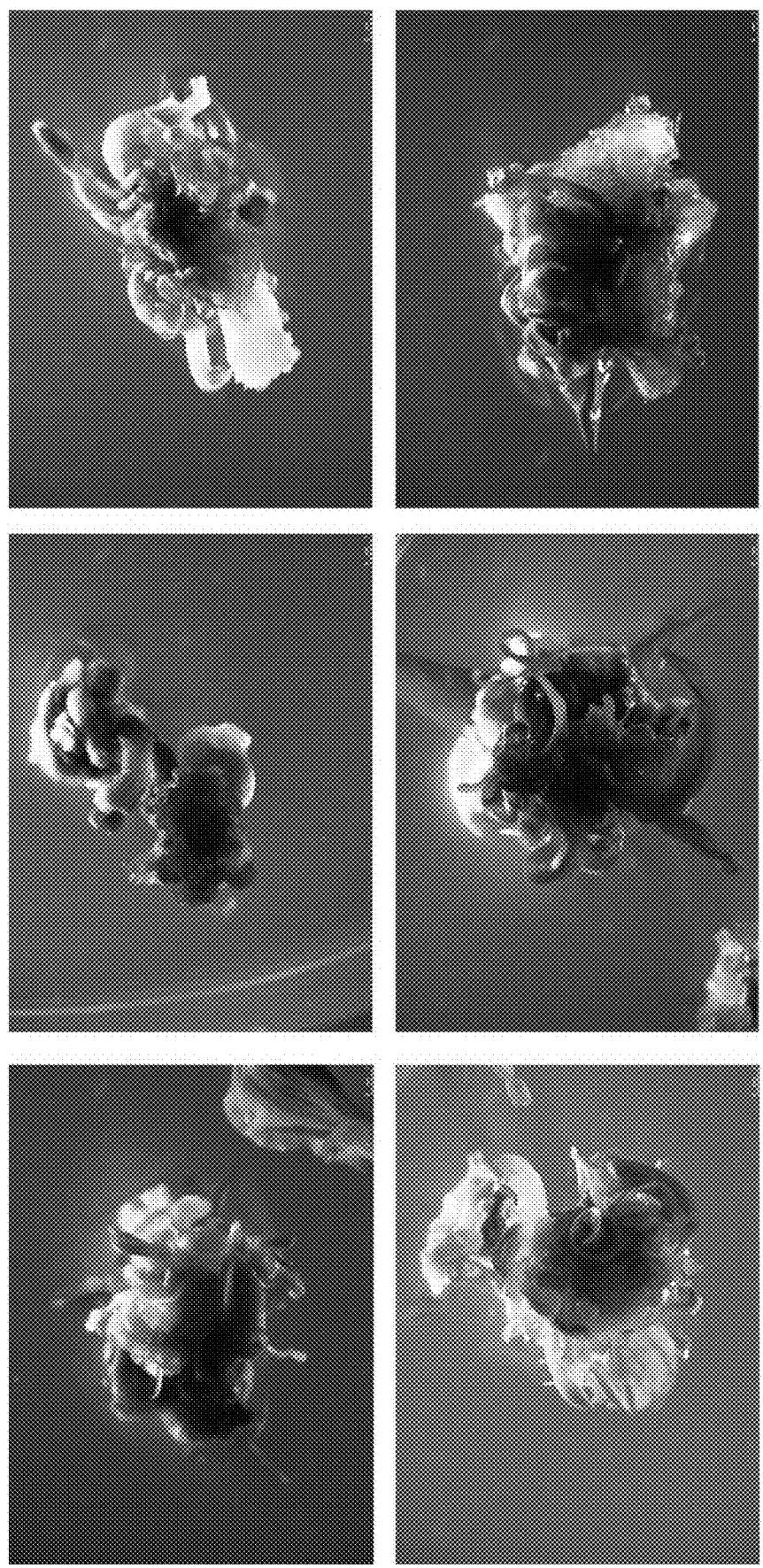
FIG. 42 shows multiple bud structures on machine excised maize mature B73 embryo axes inoculated after exposure to 7277 g; exposed to 2 ppm TDZ, 1 ppm 2,4-D for 2 weeks, then 2 ppm TDZ, 1 ppm 2,4-D, and 10 uM glyphosate for 3 weeks.
Figure 43:
FIG. 43 shows stable GUS expression in regenerated B73 maize leaves derived from hand excised embryo axes (no rooted plants recovered). Explants exposed to 7277 g; then exposed to 10 ppm BAP, 1 ppm 2,4-D for 1 week, then 2 ppm TDZ, 1 ppm 2,4-D and 10 uM glyphosate) for 2 weeks, followed by regeneration on 25 uM glyphosate (PGR-free).

It may be possible to extend our Barley mature embryo explant strategy to other monocots, such as Maize (FIG. 39). We conducted transient studies using the VS224 construct and found application of high force (either through centrifugation or pressure) as well as compromising scutellar tissue (generally through its partial removal from the embryo axis) greatly enhanced transfection of this target tissue by *Agrobacterium*. In some cases, the radical of the embryo axes is removed during excision to generate a maize shoot tip. (FIGS. 40 and 41) Using a variety of multiple bud medium, we have been able to induce budding in these maize mature meristem embryo axes. (FIG. 42) Through application of multiple bud inducing medium and application of glyphosate selection, we have been able to obtain chimeric events stably expressing GUS in greening tissue. (FIG. 43)

Examples in other monocots: Sorghum (*Sorghum bicolor* L.)

Figure 44:
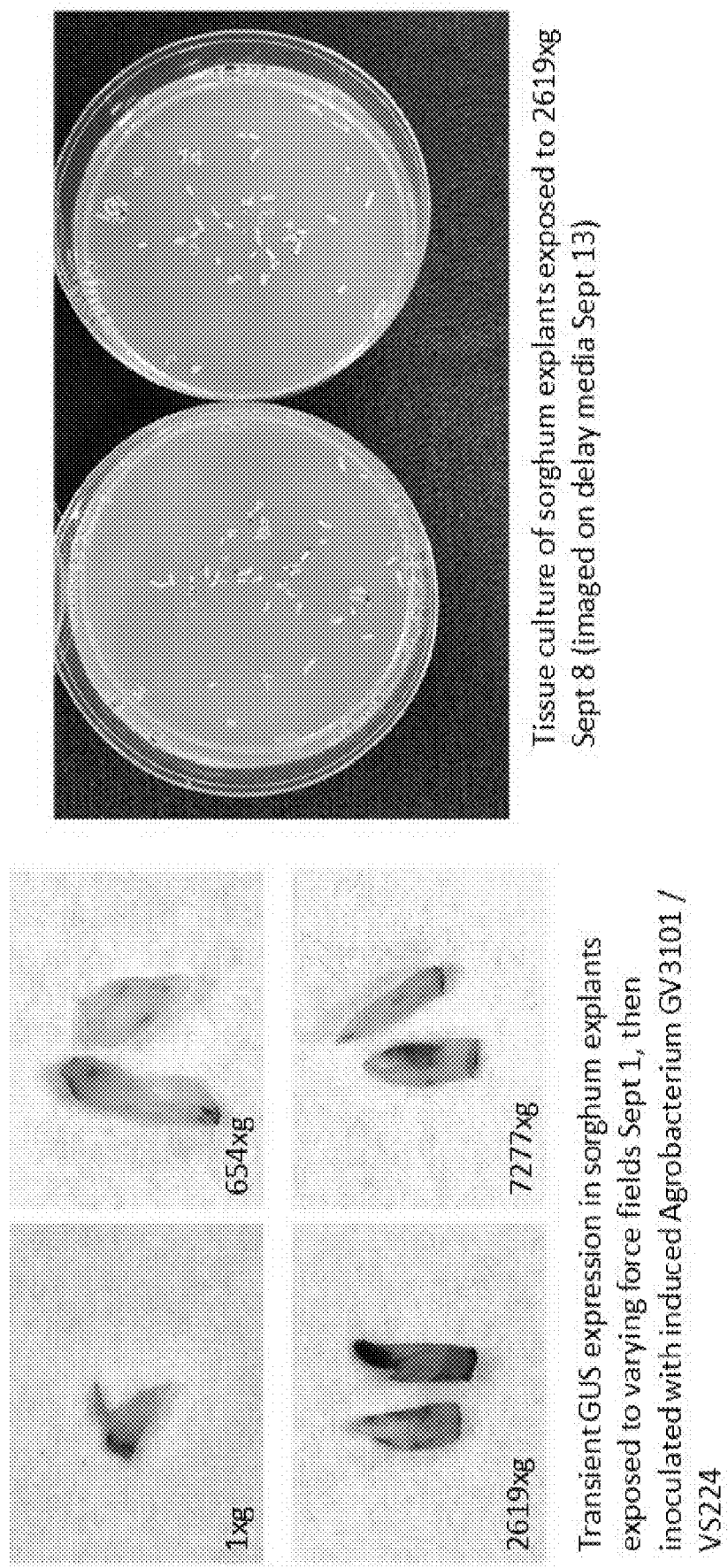
FIG. 44 shows GUS transient expression of mature *Sorghum* embryo explant (RTx430 variety) through application of increasing levels of force.
Figure 45:
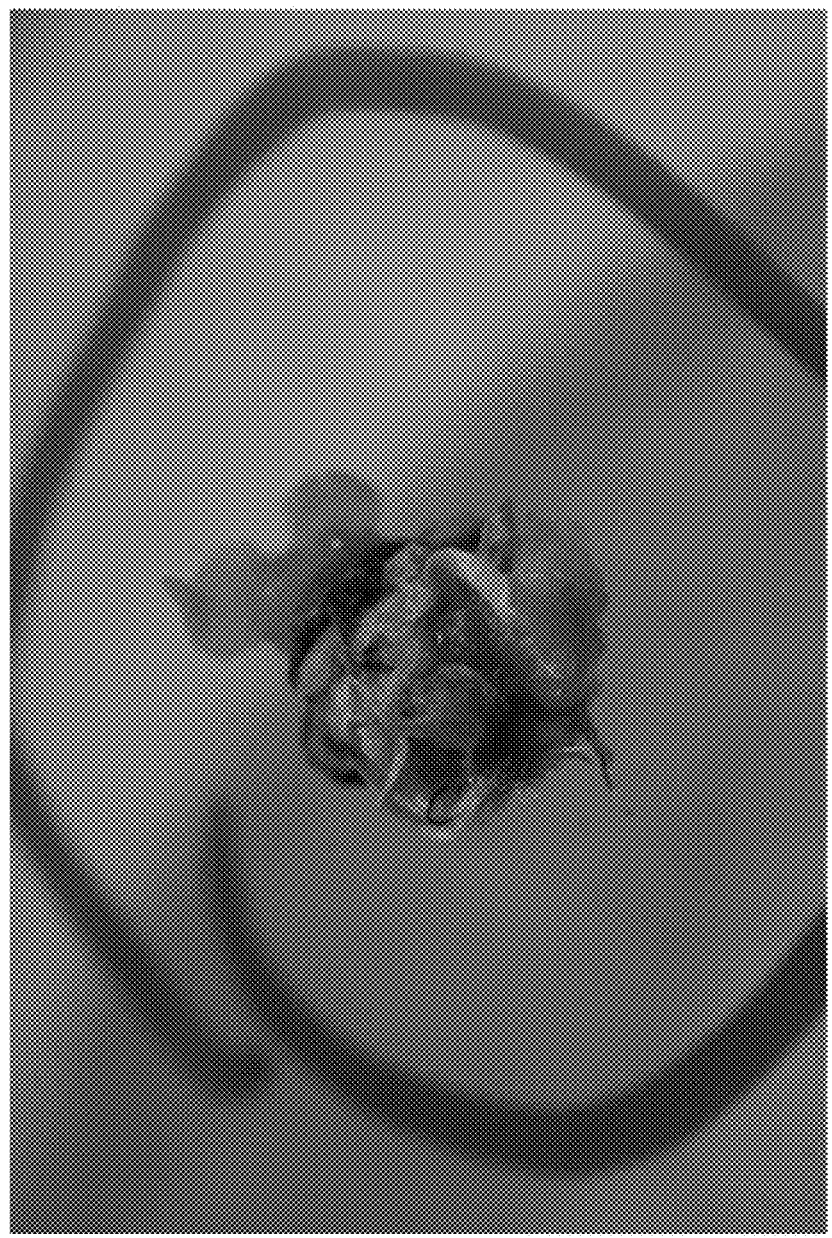
FIG. 45 shows multiple buds in *Sorghum* (RTx430 variety) derived from mature embryo explant exposed to 7277× g; then 10 ppm BAP, 1 ppm 2,4-D; then 2 ppm BAP, 1 ppm 2,4-D with 25 uM glyphosate; then to 25 uM glyphosate without PGRs.
Figure 46:
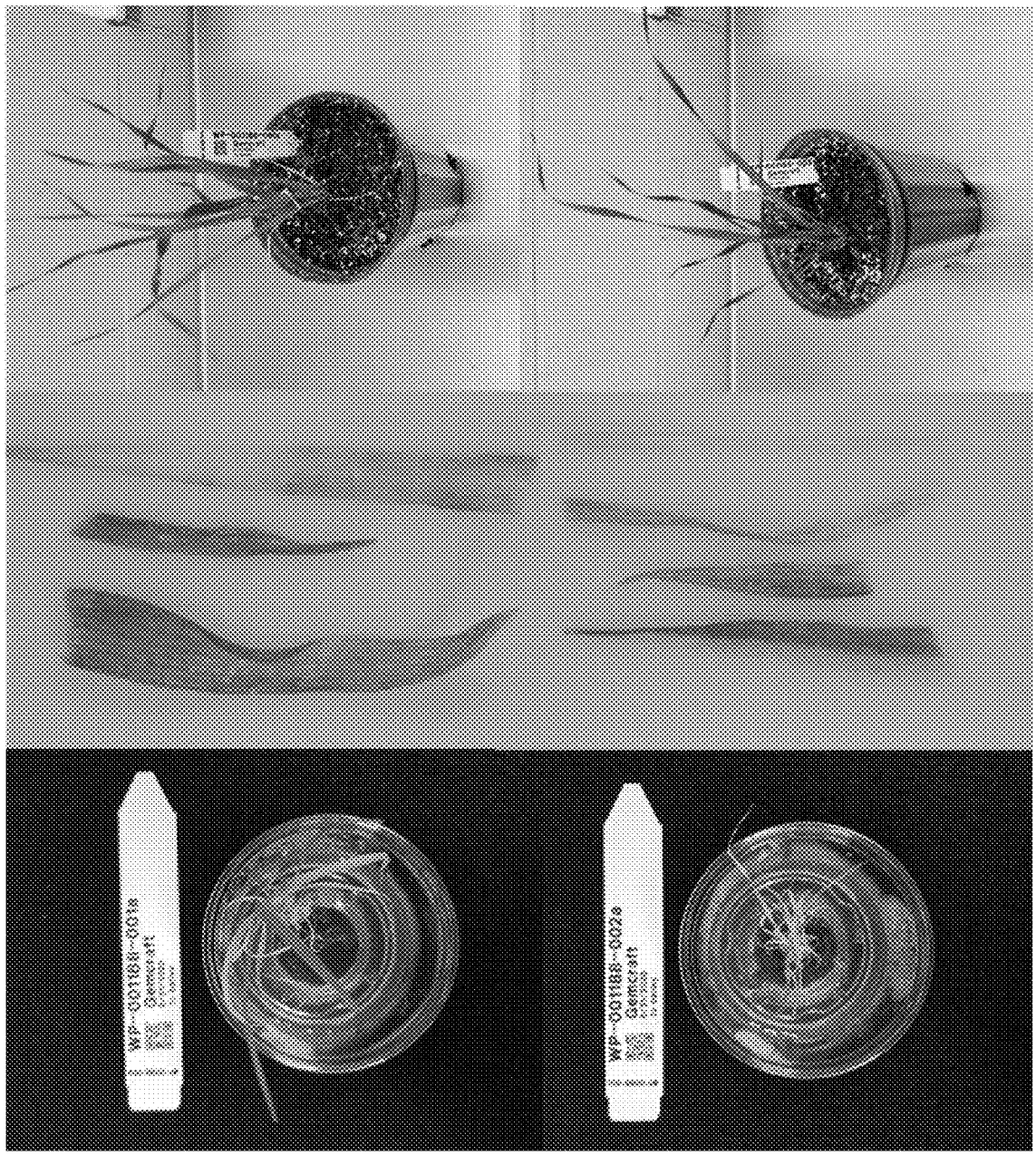
FIG. 46 shows T0 Barley plants derived from mature embryo explants using bialaphos selection and expressing GUS.
Figure 47:
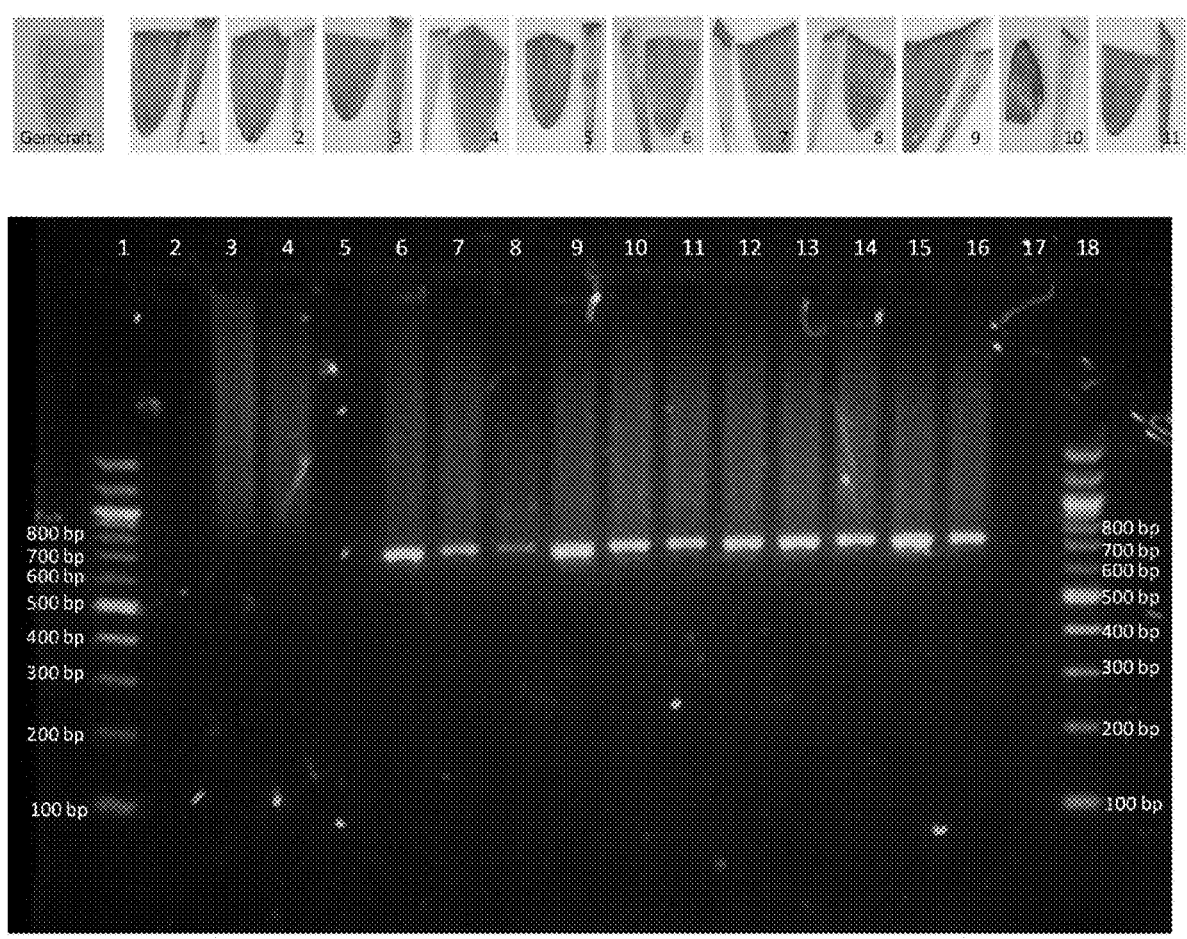
FIG. 47 shows GUS expression and tdTomato PCR in T1 leaves of Barley event WP412-4 (spike 5).

It is also possible to extend our Barley mature embryo explant strategy to other monocots, such as Sorghum (FIGS. 44 and 45).

REFERENCES

1. Ishida, Y., Saito, H., Ohta, S., Hiei, Y., Komari, T., and Kumashiro, T. (1996) High efficiency transformation of maize (*Zea mays* L.) mediated by *Agrobacterium tumefaciens*. *Nature Biotechnology* (14) 745-750.
2. Khanna, H., Becker, D., Kleidon, J., and Dale, J. (2004) Centrifugation assisted *Agrobacterium tumefaciens*-mediated transformation (CAAT) of embryogenic cell suspensions of banana (*Musa* spp. Cavendish AAA and Lady finger AAB). *Molecular Breeding* (14) 239-252.
3. Zhong, H., Srinivasan, C., and Sticklen, M. B. (1992) In-vitro morphogenesis of corn (*Zea mays* L.). *Planta* (187) 483-489.
4. Mann, D. G. J., LaFayette, P. R., Abercrombie, L. L., King, Z. R., Mazarei, M., Halter, M. C., Poovaiah, C. R., Baxter, H., Shen, H., Dixon, R. A., Parrott, W. A., and Stewart, C. N. Jr. (2012) Gateway-compatible vectors for high-throughput gene functional analysis in switchgrass (*Panicum virgatum* L.) and other monocot species. *Plant Biotechnology Journal* (10) 226-236.
5. Gordon-Kamm, B., Sardesai, N., Arling, M., Lowe, K., Hoerster, G., Betts, S., Jones, T. (2019) Using morphogenic genes to improve recovery and regeneration of transgenic plants. *Plants* (8) 38, 1-18.
6. Anand, A., Bass, S. H., Wu, E., Wang, N., McBride, K. E., Annaluru, N., Miller, M., Hua, M., Jones, T. J. (2018) An improved ternary vector system for *Agrobacterium*-mediated rapid maize transformation. *Plant Molecular Biology* (97) 187-200.
7. Rostami, H., Giri, A., Nejad, A., Moslem, A. (2013) Optimization of multiple shoot induction and plant regeneration in Indian barley (*Hordeum vulgare*) cultivars using mature embryo. *Saudi Journal of Biological Sciences* (20) 251-255.
8. Sharma, V., Hänsch, R., Mendel, R., Schulze, J. (2004) A highly efficient plant regeneration system through multiple shoot differentiation from commercial cultivars of barley (*Hordeum vulgare* L.) using meristematic shoot segments excised from germinated mature embryos. *Plant Cell Rep* (23) 9-16.
9. Sticklen, M. B., and Oraby, H. F. (2005) Shoot apical meristem: a sustainable explant for generic transformation of cereal crops. *In Vitro Cell. Dev. Biol.—Plant* (41) 187-200.
10. Bartlett, J., Alves, S., Smedley, M., Snape, J., Harwood, W. (2008) High-throughput *Agrobacterium*-mediated barley transformation. *Plant Methods* (4) 22, 1-12.
11. Kronzucker, H. J., Glass, A. D. M., Siddiqi, M. Y. (1999) Inhibition of nitrate uptake by ammonium in barley. Analysis of component fluxes. *Plant Physiol.* (120) 1: 283-292.
12. Nakano, T., Tanaka, S., Ohtani, M., Yamagami, A., Takeno, S., Hara, N., Mori, A., Nakano, A., Hirose, S., Himuro, Y., Kobayashi. M., Kushiro, T., Demura, T., Asami, T., Osada, H., and Shinozaki, K., (2018) FPX is a Novel Chemical Inducer that Promotes Callus Formation and Shoot Regeneration in Plants. *Plant Cell Physiol.* 59 (8) 1555-1567.
13. Sticklen, M. B., and Oraby, H. F. (2005) Shoot apical meristem: a sustainable explant for generic transformation of cereal crops. *In Vitro Cell. Dev. Biol.—Plant* (41) 187-200.
14. Zhong, H., Sun, B., Warkentin, D., Zhang, S., Wu, R., Wu, T., and Sticklen, M. B. (1996) The competence of maize shoot meristems for integrative transformation and inherited expression of transgenes. *Plant Physiol.* (110) 1097-1107.

Example 12

Figure 50:
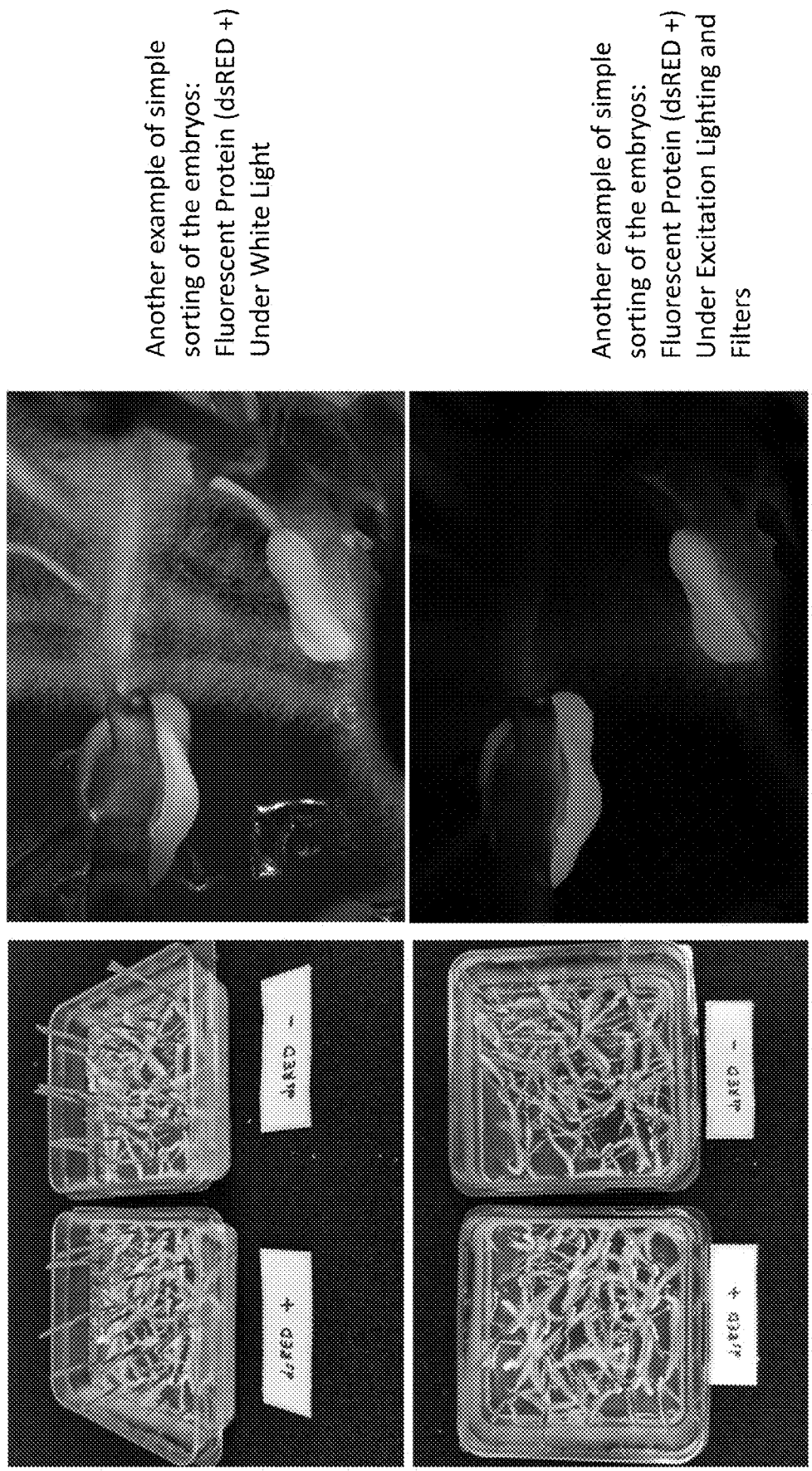
FIG. 50 shows embodiments of embryo sorting.

Optical sorting validation—This experiment was designed to demonstrate the ease of identification and sorting of embryos containing a marker. In this example, we chose a fluorescent marker, but other markers and traits could be chosen that have signatures observable under hyperspectral imaging. A segregating transgenic T0 maize ear from genotype Hi2 by B73 was harvested at 24DAP (FIG. 48). Immature embryos were extracted as described in Example 1. These ears were chosen as they would be expected to be genetically heterozygous for the trait; containing both native (non-fluorescing under appropriate conditions) and transgenic (fluorescing under appropriate conditions) traits. Non-sorted embryos were placed in sterile petri dishes and moved to a sterile tissue culture hood. Room lights were dimmed and light from LEDs specifically designed to excite the fluorescent marker were turned on. The researchers, wearing eyeglasses specifically designed to subtract interfering reflected wavelengths of light (these are called "filters" when used in optical imaging equipment), were able to quickly sort embryos that were expressing the transgenic trait from negative expressing embryos. (FIGS. 49 and 50) All the steps described can be accomplished in standard scientific optical imaging equipment.

We claim:

1. A method for preparing a dried maize explant, the method comprising the step of:
    slicing a maize embryo before drying; drying the maize embryo on moist filter paper at a temperature between about 4° C. and about 30° C. and at a relative humidity between about 20% and 60% until the maize embryo has an internal moisture content between about 2% and about 20%, wherein the maize embryo is dried over a period of at least two days in the presence of a desiccation medium comprising a saturated salt solution, whereby a dried maize explant with an internal moisture content between about 2% and about 20% is produced, whereby the dried maize explant is stored for greater than two weeks, and wherein in a population of dried maize explants at least about 65% of the dried maize explants are capable of germination after rehydration.

2. The method of claim 1, wherein the embryo is dried in the presence of desiccation medium comprising water, a tissue culture medium, or a sugar solution.

3. The method of claim 2, wherein the sugar solution comprises sucrose, trehalose or raffinose.

4. The method of claim 1, wherein the desiccation medium comprises plant growth regulators.

5. The method of claim 1, wherein the maize embryo is dried for between 2 days and about 8 days.

6. The method of claim 1, additionally comprising the step of freezing the dried explant before storing the dried explant.

7. The method of claim 1, further comprising the step of rehydrating and germinating the dried maize explant, whereby in a population of dried, rehydrated, and germinated explants at least 90% of the embryos germinate.

8. A dried maize explant generated by the method of claim 1 and having an internal moisture content between about 2% and about 20%.

9. The method of claim 1, wherein the maize embryo is obtained from a maize ear by a method comprising the steps of:
    rinsing the maize ear with ethanol;
    surface sterilizing the maize ear in a bleach solution;
    dipping the surface sterilized maize ear in a Vitamin C solution to remove residual bleach;
    removing the outer facing seed coat from kernels on the maize ear;
    removing the kernels from the maize ear;
    separating the maize embryos from cell exudate and contaminates associated with the removed kernels.

10. The method of claim 9, wherein the maize ear is covered by a husk and prior to rinsing the maize ear, the outer surface of the husk is disinfected with ethanol and removed from the maize ear.

11. The method of claim 9, wherein the maize ear is surface sterilized in a bleach solution for between about 1 minute and about 45 minutes.

12. The method of claim 9, wherein the kernels are removed from the maize ear using a field corn sheller or a popcorn sheller.

13. The method of claim 9, additionally comprising the step of grinding the removed kernels prior to separating the maize embryos from the cell exudate and contaminates.

14. The method of claim 9, wherein the maize ear is obtained from a maize plant about 15 to about 30 days after pollination and the kernels are removed from the maize ear into water prior to separation with a #6 sieve, a #8 sieve, a #10 sieve, or combinations thereof.

15. The method of claim 9, wherein the maize ear is obtained from a maize plant about 9 to about 14 days after pollination and the kernels are removed from the maize ear into a culture medium comprising sugar prior to separation with a #10 sieve, a #12 sieve, a #14 sieve, or combinations thereof.

16. A method of transforming a maize explant, the method comprising the steps of:
    rehydrating the dried maize explant produced by the method of claim 1 in a tissue culture medium;
    transforming leaf base tissue in the explant using a force treatment and *Agrobacterium*-mediated transformation or particle bombardment mediated transformation;
    inducing bud formation in the presence of a selectable marker; and
    regenerating shoots from the transgenic buds positive for the selectable marker.

17. The method of claim 16, wherein the force treatment is selected from the group consisting of centrifugation, increased pressure, sonication, vortexing, abrasion of the explant, vacuum infiltration, desiccation, nanoparticle exposure, and combinations thereof.

18. The method of claim 16, wherein the selectable marker is glyphosate, bialaphos, basta, glufosinate, hygromycin, imazapyr, or G418 (geneticin).

19. The method of claim 16, wherein bud formation is induced using a culture medium with a high cytokinin to auxin ratio.

20. The dried maize explant of claim 8, wherein the dried maize explant is frozen.

21. A population of the dried maize explants of claim 8, wherein at least 65% of the embryos germinate following rehydration of the dried maize explants.

22. A population of the frozen dried maize explants of claim 20, wherein at least 65% of the embryos germinate following thawing and rehydration of the frozen dried maize explants.

23. The method of claim 1, wherein the drying step is carried out at a temperature between about 20° C. and about 24° C. and at a relative humidity between about 50% and about 55%.

* * * * *